US012797441B2

(12) United States Patent
Liu et al.

(10) Patent No.: US 12,797,441 B2
(45) Date of Patent: Nov. 17, 2026

(54) VEGF GENE THERAPY FOR TENDON AND LIGAMENT INJURIES

(71) Applicant: Rhode Island Hospital, Providence, RI (US)

(72) Inventors: Paul Y. Liu, East Greenwich, RI (US); Xiaotian Wang, Barrington, RI (US)

(73) Assignee: Rhode Island Hospital, Providence, RI (US)

( * ) Notice: Subject to any disclaimer, the term of this patent is extended or adjusted under 35 U.S.C. 154(b) by 638 days.

(21) Appl. No.: 16/603,985

(22) PCT Filed: Apr. 13, 2018

(86) PCT No.: PCT/US2018/027495

§ 371 (c)(1),
(2) Date: Oct. 9, 2019

(87) PCT Pub. No.: WO2018/191622

PCT Pub. Date: Oct. 18, 2018

(65) Prior Publication Data

US 2020/0113972 A1 Apr. 16, 2020

Related U.S. Application Data

(60) Provisional application No. 62/485,647, filed on Apr. 14, 2017.

(51) Int. Cl.
*A61K 38/18* (2006.01)
*A61K 9/00* (2006.01)
(Continued)

(52) U.S. Cl.
CPC ........ *A61K 38/1866* (2013.01); *A61K 48/005* (2013.01); *A61P 19/04* (2018.01);
(Continued)

(58) Field of Classification Search
CPC .............. A61K 38/1866; A61K 48/005; A61K 9/0019; A61K 31/7052; A61P 19/04; C12N 15/86; C12N 2750/14143; C07K 14/52
See application file for complete search history.

(56) References Cited

U.S. PATENT DOCUMENTS 7,670,823 B1 * 3/2010 Hartley .................. C12N 15/63 435/325
2003/0215921 A1 11/2003 Coleman
(Continued)

FOREIGN PATENT DOCUMENTS

JP 2002-537790 A 11/2002
JP 2005-524710 A 8/2005
(Continued)

OTHER PUBLICATIONS

Tang JB, Wu YF, Cao Y, Chen CH, Zhou YL, Avanessian B, Shimada M, Wang XT, Liu PY. Basic FGF or VEGF gene therapy corrects insufficiency in the intrinsic healing capacity of tendons. Scientific reports. Feb. 11, 2016;6(1):1-2 (Year: 2016).*
(Continued)

*Primary Examiner* — Tracy Vivlemore
*Assistant Examiner* — Thomas R. Amick
(74) *Attorney, Agent, or Firm* — Adler Pollock & Sheehan P.C.; Michel Morency; Daniel J. Holmander

(57) ABSTRACT

Provided are compositions comprising a viral vector and a VEGF gene or a fragment thereof, and methods of using the compositions for the treatment of an injury of a fibrous connective tissue.

9 Claims, 12 Drawing Sheets

Specification includes a Sequence Listing.

(51) Int. Cl.
*A61K 48/00* (2006.01)
*A61P 19/04* (2006.01)
*C12N 15/86* (2006.01)

(52) U.S. Cl.
CPC ............ *C12N 15/86* (2013.01); *A61K 9/0019* (2013.01); *C12N 2750/14143* (2013.01)

(56) References Cited

U.S. PATENT DOCUMENTS

| | | | | |
|---|---|---|---|---|
| 2006/0140915 | A1 | 6/2006 | Schatz et al. | |
| 2007/0026044 | A1 | 2/2007 | Bunting et al. | |
| 2009/0082263 | A1 * | 3/2009 | Kaneda ................ | A01K 67/027 514/17.7 |
| 2016/0220699 | A1 * | 8/2016 | O'Heeron .............. | C12N 15/85 |
| 2016/0319303 | A1 | 11/2016 | Jimenez Cenzano et al. | |

FOREIGN PATENT DOCUMENTS

| | | | |
|---|---|---|---|
| JP | 2008523093 | A | 7/2008 |
| JP | 2015-517301 | A | 6/2015 |
| JP | 2018515102 | A | 6/2018 |
| WO | 00/52027 | A1 | 9/2000 |
| WO | 03/094617 | A2 | 11/2003 |
| WO | 2006/011600 | A1 | 2/2006 |
| WO | 2006063247 | A2 | 6/2006 |
| WO | WO2008/017023 | A2 | 2/2008 |
| WO | 2013/164793 | A2 | 11/2013 |
| WO | 2016183422 | A1 | 11/2016 |

OTHER PUBLICATIONS

GenBank Accession # AB021221.1; Jun. 3, 1999. *H. sapiens* VEGF1. Accessed on Sep. 17, 2022. (Year: 1999).*

Gray JT, Zolotukhin S. Design and construction of functional AAV vectors. InAdeno-Associated Virus 2012 (pp. 25-46). Humana Press. (Year: 2012).*

Gray GS, Fitch WM. Evolution of antibiotic resistance genes: the DNA sequence of a kanamycin resistance gene from *Staphylococcus aureus*. Molecular Biology and Evolution. Dec. 1, 1983;1(1):57-66. (Year: 1983).*

Raghunath A. Attenuation of botulinum toxin mediated blockade of exocytosis at neuromuscular junctions by viral vector mediated gene transfer into spinal motor neurons (Doctoral dissertation, Dublin City University). (Year: 2008).*

Hu C, Busuttil RW, Lipshutz GS. RH10 provides superior transgene expression in mice when compared with natural AAV serotypes for neonatal gene therapy. The journal of gene medicine. Sep. 2010;12(9):766-78. (Year: 2010).*

GenBank Accession # AF396260.1; Aug. 13, 2001. pAAV-MCS. Accessed on Sep. 17, 2022. (Year: 2001).*

Alignment of pAAV-MCS (Genbank # AF396260.1) and SEQ ID No. 11 (Year: 2022).*

Agilent AAV Helper-free system instruction manual (Year: 2024).*

Jang, Chuan-Wei, and Terry Magnuson. "A novel selection marker for efficient DNA cloning and recombineering in *E. coli.*" PloS one vol. 8,2 (2013 (Year: 2013).*

Oreff, G.L., Fenu, M., Vogl, C. et al. Species variations in tenocytes' response to inflammation require careful selection of animal models for tendon research. Sci Rep 11, 12451 (2021). (Year: 2021).*

Mao et al. (Apr. 2007) "Modulation of Digital Flexor Tendon Healing by Vascular Endothelial Growth Factor Gene Transfection in a Chicken Model", Gene Therapy, 24(4):234-240.

Tang et al, "Basic FGF or VEGF gene therapy corrects insufficiency in the intrinsic healing capacity of tendons," Scientific Report, Feb. 11, 2016 (Feb. 11, 2016), vol. 6, pp. 1-12. entire document.

"Extended European Search Report and Search Opinion for EP Application No. 18783895.8 dated Jan. 11, 2021", 6 pages.

"International Search Report and Written Opinion for PCT Application No. PCT/US2018/027495 dated Jul. 27, 2018", 10 pages.

Mehrzad , et al., "The Economic Impact of Flexor Tendon Lacerations of the Hand in the United States", Annals of Plastic Surgery, vol. 83, No. 4, Oct. 2019, pp. 419-423.

Shan , et al., "*Homo sapiens* Vascular Endothelial Growth Factor Isoform VEGF165 (VEGF) mRNA, Complete cds", GenBank: Accession No. AF486837, Apr. 3, 2002, retrieved from https://www.ncbi.nlm.nih.gov/nuccore/af486837, 2 pages.

Tang , et al., "Gene therapy strategies to improve strength and quality of flexor tendon healing", Expert Opinion on Biological Therapy, vol. 16, No. 3, 2016, pp. 291-301.

Wang , et al., "bFGF or VEGF Gene Transfer via AAV2 Vectors to the Tendon Activates Multiple Genes Critical to Tendon Growth and Regeneration: An In Vivo Study", Molecular Therapy, vol. 23, Supplement 1, Article 618, May 2015, p. S245.

Mehrzad, Raman & Liu, Paul. (2018). Developing a Gene Therapy Clinical Trial: Tips and Tricks. 10.1007/978-3-319-78957-6_8.

Umeki S. Anti-inflammatory action of gentamycin through inhibitory effect on neutrophil NADPH oxidase activity. Comp Biochem Physiol B Biochem Mol Biol. Apr. 1995;110(4):817-21. doi: 10.1016/0305-0491(94)00203-7. PMID: 7749629.

Berkay et al., "Poster 383: Incidence of Sports Related Tendon Ruptures in the United States", The Orthopaedic Journal of Sports Medicine, vol. 11, Issue 7 (suppl 3), AOSSM Annual Meeting Supplement, Jul. 2023, 4 pages.

Hu et al., "Applications of Functionally-Adapted Hydrogels in Tendon Repair", Frontiers in Bioengineering and Biotechnology, vol. 11, Feb. 2, 2023, pp. 1-21.

* cited by examiner

VEGF GENE THERAPY FOR TENDON AND LIGAMENT INJURIES

CROSS-REFERENCE TO RELATED APPLICATIONS

This application is a national stage application filed under 35 U.S.C. § 371, of International Application No. PCT/US18/27495, filed Apr. 13, 2018, and claims the benefit of and priority to U.S. Provisional Patent Application No. 62/485,647, filed Apr. 14, 2017, the entire contents of which are incorporated by reference in their entirety.

STATEMENT AS TO FEDERALLY SPONSORED RESEARCH

This invention made with U.S. Government support under GM122732 awarded by the National Institutes of Health. The Government has certain rights in the invention.

SEQUENCE LISTING

Incorporated by reference in its entirety is a computer-readable nucleotide/amino acid sequence listing submitted concurrently herewith and identified as follows: 49,152 bytes text file named "021486-634001WO_Sequence_Listing_ST25.txt" created on Apr. 11, 2018.

BACKGROUND

Tendon injuries constitute one of the most common disorders of the human body, affecting 1 in 2,000 people each year, with the tendon injuries to the hand and wrist occurring in 1 in 2,700 people each year. These tendon injuries can result from trauma, overuse, or age-related degeneration from work, daily life, and sports activities. Injuries to tendons, tendon-bone-junctions, and related tissues (such as ligaments) can occur in numerous areas of the body. People with such injuries constitute a large proportion of the patients treated in emergency rooms, inpatient surgical departments, outpatient clinics, and rehabilitation facilities. Damaged tendons heal poorly; their surgical repair frequently ends in unpredictable rupture or impaired extremity motion due to insufficient healing capacity. The treatment of damaged tendons remains a challenge in medicine because of the insufficiency of the healing capacity of the tendon itself and lack of method to increase the biological healing strength. There is thus a critical need for novel efficacious therapies for patients with tendon injuries. Provided herein are solutions to these and other problems in the art.

SUMMARY

Provided herein are compositions and methods for treating tendon injuries and other fibrous connective tissues (e.g., ligaments and fasciae) injuries.

The invention provides a method for treating an injury of a fibrous connective tissue in a subject in need thereof. In embodiments, the method includes administering to the subject a therapeutically effective amount of a polynucleotide comprising vascular endothelial growth factor (VEGF) gene or a fragment thereof. In embodiments, the polynucleotide further includes a sequence encoding a gene product for kanamycin resistance. For example, the sequence encoding a gene product for kanamycin resistance comprises the sequence of SEQ ID NO: 10. In embodiments, the polynucleotide comprises the sequence of SEQ ID NO: 11. The polynucleotide can be administered locally, e.g., directly into or onto the defect fibrous connective tissue. The polynucleotide can be administered via an injection. The polynucleotide can be formulated as a solution, a gel, a paste, a powder, or a suspension.

A fibrous connective tissue that can be treated by the methods described herein can be a ligament, a tendon, a fasciae or any combination thereof. A ligament is the fibrous connective tissue that connects bones to other bones and is also known as articular ligament, articular larua, fibrous ligament, or true ligament. A tendon or sinew is a tough band of fibrous connective tissue that usually connects muscle to bone and is capable of withstanding tension. A fascia is a band or sheet of connective tissue, primarily collagen, beneath the skin that attaches, stabilizes, encloses, and separates muscles and other internal organs. Ligaments are similar to tendons and fasciae as they are all made of connective tissue. The differences in them are in the connections that they make: ligaments connect one bone to another bone, tendons connect muscle to bone, and fasciae connect muscles to other muscles.

A "subject" is preferably a mammal. The mammal can be a human, non-human primate, mouse, rat, dog, cat, horse, or cow, but are not limited to these examples. A subject can be male or female. A subject can be one who has been previously diagnosed or identified as having injuries of ligament, tendon, and/or fasciae (e.g., tendinopathy), and optionally has already undergone, or is undergoing, a therapeutic intervention for these injuries. Alternatively, a subject can also be one who has not been previously diagnosed as having ligament, tendon, and/or fasciae injuries, but who is at risk of developing such condition, e.g. due to trauma, overuse, and/or age-related degeneration from work, daily life, or sports activities.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

A "VEGF gene" as referred to herein includes any of the recombinant or naturally-occurring forms of the gene encoding vascular endothelial growth factor (VEGF), homologs or variants thereof that maintain VEGF protein activity (e.g. within at least 50%, 80%, 90%, 95%, 96%, 97%, 98%, 99% or 100% activity compared to VEGF). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring VEGF polypeptide. In embodiments, the VEGF family comprises in mammals five members: VEGF-A, placenta growth factor (PGF), VEGF-B, VEGF-C and VEGF-D. In embodiments, VEGF gene used herein is a VEGF-A. In embodiments, VEGF gene used herein is substantially identical (e.g., 80%, 85%, 90%, 95%, 96%, 97%, 98%, 99% or 100% identical) to the nucleic acid identified by the NCBI reference number (NM_003376, NM_001025366, NM_001025367, NM_001025368, NM_001025369, NM 001025370, NM_001033756, NM_001171622, NM_001171623, NM_001171624, NM_001171625, NM_001171626, NM_001171627, NM_001171628, NM_001171629, NM_001171630, NM_001204384, NM_001204385, NM_001287044, or NM_001317010) or a variant having substantial identity thereto. In embodiments, VEGF gene used herein is substantially identical (e.g., 80%, 85%, 90%, 95%, 96%, 97%, 98%, 99% or 100% identical) to the nucleic acid sequence of SEQ ID NO: 1, 2, 3, 4, 5, 6, 7, 8, or 9. In embodiments, VEGF gene used herein is substantially identical (e.g., 80%, 85%, 90%, 95%, 96%, 97%, 98%, 99% or 100% identical) to the nucleic acid sequence of SEQ ID NO: 9.

In embodiments, the VEGF gene or a fragment thereof used in any method described herein is within a vector (e.g., a viral vector). As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

"An effective amount" or "a therapeutically effective amount" as provided herein refers to an amount effective to achieve its intended purpose. The actual amount effective for a particular application will depend, inter alia, on the condition being treated. When administered in methods to treat a disease, the pharmaceutical compositions described herein will contain an amount VEGF gene or a fragment thereof (and optionally within a viral vector) to achieve the desired result, e.g., reducing, eliminating, or slowing the progression of disease symptoms (e.g., tendon, ligament, and/or fascia injuries), or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In embodiments, the disease or condition to be treated is tendinopathy.

As used herein, "treating" or "treat" describes the management and care of a patient for the purpose of combating a disease, condition, or disorder and includes the administration of a composition described herein to alleviate the symptoms or complications of a disease, condition or disorder, or to eliminate the disease, condition or disorder. The term "treat" can also include treatment of a cell in vitro or an animal model.

As used herein, the term "alleviate" is meant to describe a process by which the severity of a sign or symptom of a disorder is decreased. Importantly, a sign or symptom can be alleviated without being eliminated. The administration of compositions or pharmaceutical compositions of the invention may or can lead to the elimination of a sign or symptom, however, elimination is not required. Effective dosages should be expected to decrease the severity of a sign or symptom. For instance, a sign or symptom of a disorder such as tendinopathy, which can occur in multiple locations, is alleviated if the severity of the tendinopathy is decreased within at least one of multiple locations.

The invention also provides a composition that includes a viral vector and a VEGF gene or a fragment thereof. In embodiments, the viral vector is an adeno-associated virus (AAV) vector. In embodiments, the viral vector is AAV type 2 (AAV2) vector. In embodiments, VEGF gene used herein is substantially identical (e.g., 80%, 85%, 90%, 95%, 96%, 97%, 98%, 99% or 100% identical) to the nucleic acid sequence of SEQ ID NO: 1, 2, 3, 4, 5, 6, 7, 8, or 9. In embodiments, VEGF gene used herein is substantially identical (e.g., 80%, 85%, 90%, 95%, 96%, 97%, 98%, 99% or 100% identical) to the nucleic acid sequence of SEQ ID NO: 9. The composition can further comprise a sequence encoding a gene product for kanamycin resistance. In embodiments, the sequence encoding a gene product for kanamycin resistance comprises the nucleic acid sequence of SEQ ID NO: 10. The composition described herein can be formulated as a solution, a gel, a paste, a powder, or a suspension. The composition described herein can be formulated for administrating directly into or onto a fibrous connective tissue. The composition described herein can be formulated for administration via an injection.

The compositions described herein can be purified. Purified compositions are at least about 60% by weight (dry weight) the compound of interest. Preferably, the preparation is at least about 75%, more preferably at least about 90%, and most preferably at least about 99% or higher by weight the compound of interest. Purity is measured by any appropriate standard method, for example, by High-performance liquid chromatography, polyacrylamide gel electrophoresis.

A "pharmaceutical composition" is a formulation containing the composition (e.g., a VEGF gene or a VEGF gene within a viral vector) described herein in a form suitable for administration to a subject. In embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed nucleic acid) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In embodiments, the active VEGF gene is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. A thorough discussion of pharmaceutically acceptable excipients is available in REMINGTON'S PHARMACEUTICAL SCIENCES (Mack Pub. Co., N.J. 1991). Pharmaceutically acceptable excipients in therapeutic compositions may contain liquids such as water, saline, glycerol and ethanol. Additionally, auxiliary substances, such as wetting or emulsifying agents, pH buffering substances, and the like, may be present in such vehicles.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A pharmaceutical composition of the invention can be administered to a subject in many of the well-known methods currently used for chemotherapeutic treatment. For example, for treatment of tendinopathy, a composition of the invention may be injected directly into tendons, injected into the blood stream or body cavities or taken orally or applied through the skin with patches. The dose chosen should be sufficient to constitute effective treatment but not so high as to cause unacceptable side effects. The state of the disease condition (e.g., tendinopathy) and the health of the patient should preferably be closely monitored during and for a reasonable period after treatment.

As used herein, "monotherapy" refers to the administration of a single active or therapeutic compound to a subject in need thereof. Preferably, monotherapy will involve administration of a therapeutically effective amount of an active composition (e.g., a VEGF gene or a VEGF gene within a viral vector or any composition described herein).

As used herein, "combination therapy" or "co-therapy" includes the administration of a composition described herein and at least a second agent as part of a specific treatment regimen intended to provide the beneficial effect from the co-action of these therapeutic agents. The beneficial effect of the combination may include, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A composition described herein may be administered in combination with a second antibiotic agent.

The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

BRIEF DESCRIPTION OF THE DRAWINGS

FIGS. 2E-21 showing the real-time PCR analysis of changes in expression of the fibronectin (FN) at weeks 6, and 8 and the laminin (LN) at weeks 1 and 2. Statistical significance is shown in the graph. * indicates the data of significant difference from those in the non-injection controls. Sample sizes at each time point in each group were 6 to 8 for gene expression analysis and 5 or 6 for western blot analysis.

FIG. 4 is a bar graph showing tendon healing strengths (data of weeks 1, 2, 3, 4, 6, and 8 shown, n=12, each group at each time point). Compared with non-injection and sham vector controls, the strengths of the AAV2-bFGF injected tendon had significant increases from week 2 and lasted up to week 8 ($p<0.01$ or $p<0.001$). In contrast, AAV2-VEGF treatment brought more robust and significant increases at week 3 ($p<0.01$) and week 4 ($p<0.001$). The strengths of the tendons injected with AAV2-VEGF were significantly greater compared with non-injection controls or sham vector injection controls at weeks 6 and 8 ($p<0.05$ or $p<0.01$). No significant difference in the strengths between the sham vector and non-treatment controls ($p>0.05$, statistical power >0.80). Compared with the strengths of non-injection controls, the percent increases in the strength were 72%, 68% and 91% for the AAV2-bFGF treated tendons at weeks 2, 3, and 4, respectively, and the increases were 82% and 210% for the AAV2-VEGF treated tendons at week 3 and 4, respectively. *indicates the data of significant difference from those in the non-injection and sham vector controls at individual time points. The bar in each group of the four bars, from left to right, represents non-injection control, AAV2 sham vector, AAV2-bFGF, and AAV2-VEGF respectively.

FIG. 6A is an AAV2-bFGF treated tendon; FIG. 6B is an AAV2-VEGF treated tendon; FIG. 6C is a non-injection control tendon, and FIG. 6D is an uninjured tendon. Morphologically, the cellularity and collagen formation in AAV2-bFGF or AAV2-VEGF treated tendon (FIGS. 6A, 6B) are greater than those in the non-treatment control (FIG. 6C) or uninjured tendon (FIG. 6D). This is at the beginning of the tendon remodeling (week 6), so cellularity in the tendon still much more robust in these healing tendons. The sections stained with immunohistochemistry were used for the observation (×400, magnification). Section shown in (FIGS. 6A, 6C, 6D) was stained with mouse anti-rat bFGF antibody (05-118, Millipore Corp., Billerica, Mass.) and that shown in 6B was stained with mouse anti-human VEGF (Santa Cruz, Dallas, Texas).

FIG. 7 is the map of AAV vector plasmid pAAV2-KanR-VEGF used herein.

DETAILED DESCRIPTION

Figure 1A:
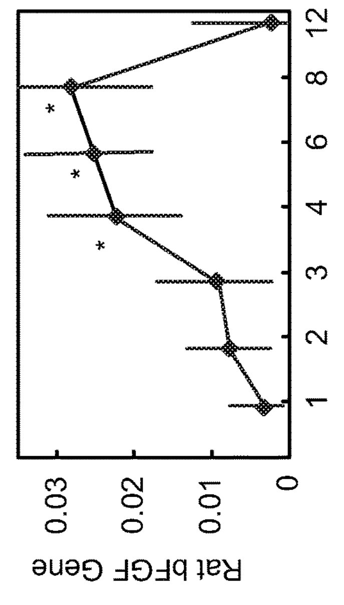
FIG. 1A is a line graph showing transgene expression in AAV2-bFGF injected tendons. Transgene (rat bFGF) expression in AAV2-bFGF injected tendon increased from weeks 1 to 3, peaked from weeks 4 to 8, dropped drastically after week 8, and was very low at week 12. *indicates the data significantly greater than that at other time-points ($p<0.05$ or $p<0.01$).

Tendon injuries constitute one of the most common traumas to the human body, with tendon injuries to the hand and wrist occurring in over 100,000 people annually in this country alone. Serious tendon lacerations result in millions of lost days from work each year. With >100,000 injuries per year, at least 3 months out of work/patient, and a re-rupture rate (with subsequent second operation) around 10-20%, the estimated cost of tendon injuries of the hand in the U.S. is >$1.2 billion annually. In fact, injuries in tendons are ranked first in the order of most expensive injury types and significant permanent disability from incomplete rehabilitation is all too often the final result. These tendon injuries can result from trauma, overuse, or age-related degeneration from work, daily life, and sports activities. Since physical exercise is frequently a major part of many professions daily schedule such as the Navy, Army, Military, professional athletes etc., they tend to suffer a higher incidence of tendon injuries than most others and are in high demand of proper healing. Damaged tendons heal poorly; their surgical repair frequently ends in unpredictable rupture or impaired extremity motion due to stiffness or adhesions. Tendons, particularly those covered by an intrasynovial sheath, have very limited vascular supply, lack cellularity, and have low growth factor activity. Early active motion is important to recovery of tendon function, but it increases risk of rupture. The treatment of damaged tendons remains a major challenge in medicine because of the insufficiency of the healing capacity and lack of methods to increase the healing strength. Thus, improving the healing environment of the surgically repaired tendon is a key component for these injuries and may reduce the postoperative rupture rate and allow for less adhesion formation.

Over the past decade, we have demonstrated delivery of growth factor genes such as vascular endothelial growth factor (VEGF) into tendons may enhance healing strength, reduce adhesion formation and rupture rate. Wild-type adeno-associated virus (AAV) is a nonpathogenic, widespread defective human parvovirus, which does not cause any human diseases. Because of its safety and efficiency, AAV has been used as a promising vector in clinical trials. In our preclinical studies, we have demonstrated that AAV2-VEGF (AAV serotype 2 vectors encoding human VEGF 165) local injection to injured tendon significantly increased tendon strength without increasing adhesion formation in a chicken flexor tendon healing model. Moreover, the transgene expression dissipated after healing was complete. These findings strongly suggest that AAV2-VEGF gene transfer may provide a solution to the insufficiencies of the tendon intrinsic healing capacity and offer an effective therapeutic possibility for patients with tendon disunion. Thus, our clinical trial may result in decrease of the rupture rate of repaired tendon; faster return to employment and most importantly, optimal recovery of function of the hand that will mitigate this huge economic impact.

Provided herein are compositions including a VEGF gene or a fragment thereof in an improved vector plasmid (e.g., AAV) with a genomic insert expressing resistance to kanamycin (KanR) that does not interfere with ampicillin resistance. Ampicillin resistance is used in most AAV vector plasmids, as a way of screening for plasmids encoding the VEGF. However, the use of ampicillin is not strictly in compliance with FDA's guideline/desire of not to use a construct where even a theoretical possibility of introducing ampicillin resistance.

The plasmid antibiotic selection is the most-commonly used technique in the screening and production of plasmids. In exemplary embodiments, the constructs including VEGF and KanR were introduced into bacterium *E. coli*. The bacterial cells were then cultured in kanamycin containing growth medium. Thus, only cells that contained the plasmids with kanamycin resistance gene were able to survive and grow. The grown cell colonies were harvested for further analysis to confirm the correct cloning without any mutation of inserts.

In embodiments, a kanamycin resistance gene includes the following nucleic acid sequence:

```
                                   (SEQ ID NO: 10)
GTTACA TTGCACAAGA TAAAAATATA TCATCATGAA CAATAAAA

CT GTCTGCTTAC ATAAACAGTA ATACAAGGGG TGTTATGAGC

CATATTCAAC GGGAAACGTC GAGGCCGCGA TTAAATTCCA

ACATGGATGC TGATTTATAT GGGTATAAAT GGGCTCGCGA

TAATGTCGGG CAATCAGGTG CGACAATCTA TCGCTTGTAT

GGGAAGCCCG ATGCGCCAGA GTTGTTTCTG AAACATGGCA

AAGGTAGCGT TGCCAATGAT GTTACAGATG AGATGGTCAG

ACTAAACTGG CTGACGGAAT TTATGCCTCT TCCGACCATC
```

-continued

```
AAGCATTTTA TCCGTACTCC TGATGATGCA TGGTTACTCA
CCACTGCGAT CCCCGGAAAA ACAGCATTCC AGGTATTAGA
AGAATATCCT GATTCAGGTG AAAATATTGT TGATGCGCTG
GCAGTGTCCC TGCGCCGGTT GCATTCGATT CCTGTTTGTA
ATTGTCCTTT TAACAGCGAT CGCGTATTTC GTCTCGCTCA
GGCGCAATCA CGAATGAATA ACGGTTTGGT TGATGCGAGT
GATTTTGATG ACGAGCGTAA TGGCTGGCCT GTTGAACAAG
TCTGGAAAGA AATGCATAAA CTTTTGCCAT TCTCACCGGA
TTCAGTCGTC ACTCATGGTG ATTTCTCACT TGATAACCTT
```

-continued

```
ATTTTTGACG AGGGGAAATT AATAGGTTGT ATTGATGTTG
GACGAGTCGG AATCGCAGAC CGATACCAGG ATCTTGCCAT
CCTATGGAAC TGCCTCGGTG AGTTTTCTCC TTCATTACAG
AAACGGCTTT TTCAAAAATA TGGTATTGAT AATCCTGATA
TGAATAAATT GCAGTTTCAT TTGATGCTCG ATGAGTTTTT CTAA
```

Also provided herein are compositions including a VEGF gene or a fragment thereof within a viral vector. In embodiments, the viral vector is an AAV vector. In embodiments, the viral vector is an AAV2 vector.

In embodiments, a VEGF gene used in any composition and method described herein is a VEGF-A isoform a having the following nucleic acid sequence:

(SEQ ID NO: 1)

```
   1 tcgcggaggc ttggggcagc cgggtagctc ggaggtcgtg gcgctggggg ctagcaccag
  61 cgctctgtcg ggaggcgcag cggttaggtg gaccggtcag cggactcacc ggccagggcg
 121 ctcggtgctg gaatttgata ttcattgatc cgggttttat ccctcttctt ttttcttaaa
 181 catttttttt taaaactgta ttgtttctcg ttttaattta tttttgcttg ccattcccca
 241 cttgaatcgg gccgacggct tggggagatt gctctacttc cccaaatcac tgtggatttt
 301 ggaaaccagc agaaagagga aagaggtagc aagagctcca gagagaagtc gaggaagaga
 361 gagacggggt cagagagagc gcgcgggcgt gcgagcagcg aaagcgacag gggcaaagtg
 421 agtgacctgc ttttgggggt gaccgccgga gcgcggcgtg agccctcccc cttgggatcc
 481 cgcagctgac cagtcgcgct gacggacaga cagacagaca ccgcccccag ccccagctac
 541 cacctcctcc ccggccggcg gcggacagtg gacgcggcgg cgagccgcgg gcaggggccg
 601 gagcccgcgc ccggaggcgg ggtggagggg gtcggggctc gcggcgtcgc actgaaactt
 661 ttcgtccaac ttctgggctg ttctcgcttc ggaggagccg tggtccgcgc gggggaagcc
 721 gagccgagcg gagccgcgag aagtgctagc tcgggccggg aggagccgca gccggaggag
 781 ggggaggagg aagaagagaa ggaagaggag agggggccgc agtggcgact cggcgctcgg
 841 aagccgggct catggacggg tgaggcggcg gtgtgcgcag acagtgctcc agccgcgcgc
 901 gctccccagg ccctggcccg ggcctcgggc cggggaggaa gagtagctcg ccgaggcgcc
 961 gaggagagcg ggccgcccca cagcccgagc cggagaggga gcgcgagccg cgccggcccc
1021 ggtcgggcct ccgaaaccat gaactttctg ctgtcttggg tgcattggag ccttgccttg
1081 ctgctctacc tccaccatgc caagtggtcc caggctgcac ccatggcaga aggaggaggg
1141 cagaatcatc acgaagtggt gaagttcatg gatgtctatc agcgcagcta ctgccatcca
1201 atcgagaccc tggtggacat cttccaggag taccctgatg agatcgagta catcttcaag
1261 ccatcctgtg tgcccctgat gcgatgcggg ggctgctgca atgacgaggg cctggagtgt
1321 gtgcccactg aggagtccaa catcaccatg cagattatgc ggatcaaacc tcaccaaggc
1381 cagcacatag gagagatgag cttcctacag cacaacaaat gtgaatgcag accaaagaaa
1441 gatagagcaa gacaagaaaa aaaatcagtt cgaggaaagg gaaaggggca aaaacgaaag
1501 cgcaagaaat cccggtataa gtcctggagc gtgtacgttg gtgcccgctg ctgtctaatg
1561 ccctggagcc tccctggccc ccatccctgt gggccttgct cagagcggag aaagcatttg
1621 tttgtacaag atccgcagac gtgtaaatgt tcctgcaaaa acacagactc gcgttgcaag
1681 gcgaggcagc ttgagttaaa cgaacgtact tgcagatgtg acaagccgag gcggtgagcc
```

-continued

```
1741 gggcaggagg aaggagcctc cctcagggtt tcgggaacca gatctctcac caggaaagac
1801 tgatacagaa cgatcgatac agaaaccacg ctgccgccac cacaccatca ccatcgacag
1861 aacagtcctt aatccagaaa cctgaaatga aggaagagga gactctgcgc agagcacttt
1921 gggtccggag ggcgagactc cggcggaagc attcccgggc gggtgaccca gcacggtccc
1981 tcttggaatt ggattcgcca ttttattttt cttgctgcta aatcaccgag cccggaagat
2041 tagagagttt tatttctggg attcctgtag acacacccac ccacatacat acatttatat
2101 atatatatat tatatatata taaaaataaa tatctctatt ttatatatat aaaatatata
2161 tattcttttt ttaaattaac agtgctaatg ttattggtgt cttcactgga tgtatttgac
2221 tgctgtggac ttgagttggg aggggaatgt tcccactcag atcctgacag ggaagaggag
2281 gagatgagag actctggcat gatctttttt ttgtcccact tggtggggcc agggtcctct
2341 cccctgccca ggaatgtgca aggccagggc atgggggcaa atatgaccca gttttgggaa
2401 caccgacaaa cccagccctg gcgctgagcc tctctacccc aggtcagacg gacagaaaga
2461 cagatcacag gtacagggat gaggacaccg gctctgacca ggagtttggg gagcttcagg
2521 acattgctgt gctttgggga ttccctccac atgctgcacg cgcatctcgc cccccagggggc
2581 actgcctgga agattcagga gcctgggcgg ccttcgctta ctctcacctg cttctgagtt
2641 gcccaggaga ccactggcag atgtcccggc gaagagaaga gacacattgt tggaagaagc
2701 agcccatgac agctcccctt cctgggactc gccctcatcc tcttcctgct ccccttcctg
2761 gggtgcagcc taaaaggacc tatgtcctca caccattgaa accactagtt ctgtcccccc
2821 aggagacctg gttgtgtgtg tgtgagtggt tgaccttcct ccatcccctg gtccttccct
2881 tcccttcccg aggcacagag agacagggca ggatccacgt gcccattgtg gaggcagaga
2941 aaagagaaag tgttttatat acggtactta tttaatatcc ctttttaatt agaaattaaa
3001 acagttaatt taattaaaga gtagggtttt ttttcagtat tcttggttaa tatttaattt
3061 caactattta tgagatgtat cttttgctct ctcttgctct cttatttgta ccggtttttg
3121 tatataaaat tcatgtttcc aatctctctc tccctgatcg gtgacagtca ctagcttatc
3181 ttgaacagat atttaatttt gctaacactc agctctgccc tccccgatcc cctggctccc
3241 cagcacacat tcctttgaaa taaggtttca atatacatct acatactata tatatatttg
3301 gcaacttgta tttgtgtgta tatatatata tatatgttta tgtatatatg tgattctgat
3361 aaaatagaca ttgctattct gtttttttata tataaaaaca aaacaagaaa aaatagagaa
3421 ttctacatac taaatctctc tcctttttta attttaatat ttgttatcat ttatttattg
3481 gtgctactgt ttatccgtaa taattgtggg gaaaagatat taacatcacg tctttgtctc
3541 tagtgcagtt tttcgagata ttccgtagta catatttatt tttaaacaac gacaaagaaa
3601 tacagatata tcttaaaaaa aaaaaagcat tttgtattaa agaatttaat tctgatctca
3661 aaaaaaaaaa aaaaaaa
```

In embodiments, a VEGF gene used in any composition and method described herein is a VEGF-A isoform b having the following nucleic acid sequence:

```
                                                    (SEQ ID NO: 2)
   1 tcgcggaggc ttggggcagc cgggtagctc ggaggtcgtg gcgctggggg ctagcaccag
  61 cgctctgtcg ggaggcgcag cggttaggtg gaccggtcag cggactcacc ggccagggcg
 121 ctcggtgctg gaatttgata ttcattgatc cgggttttat ccctcttctt ttttcttaaa
 181 catttttttt taaaactgta ttgtttctcg ttttaattta tttttgcttg ccattcccca
```

-continued

```
 241 cttgaatcgg gccgacggct tggggagatt gctctacttc cccaaatcac tgtggatttt
 301 ggaaaccagc agaaagagga aagaggtagc aagagctcca gagagaagtc gaggaagaga
 361 gagacggggt cagagagagc gcgcgggcgt gcgagcagcg aaagcgacag gggcaaagtg
 421 agtgacctgc ttttgggggt gaccgccgga gcgcggcgtg agccctcccc cttgggatcc
 481 cgcagctgac cagtcgcgct gacggacaga cagacagaca ccgcccccag ccccagctac
 541 cacctcctcc ccggccggcg gcggacagtg gacgcggcgg cgagccgcgg gcaggggccg
 601 gagcccgcgc ccggaggcgg ggtggagggg gtcggggctc gcggcgtcgc actgaaactt
 661 ttcgtccaac ttctgggctg ttctcgcttc ggaggagccg tggtccgcgc gggggaagcc
 721 gagccgagcg gagccgcgag aagtgctagc tcgggccggg aggagccgca gccggaggag
 781 ggggaggagg aagaagagaa ggaagaggag agggggccgc agtggcgact cggcgctcgg
 841 aagccgggct catggacggg tgaggcggcg gtgtgcgcag acagtgctcc agccgcgcgc
 901 gctccccagg ccctggcccg ggcctcgggc cggggaggaa gagtagctcg ccgaggcgcc
 961 gaggagagcg ggccgcccca cagcccgagc cggagaggga gcgcgagccg cgccggcccc
1021 ggtcgggcct ccgaaaccat gaactttctg ctgtcttggg tgcattggag ccttgccttg
1081 ctgctctacc tccaccatgc caagtggtcc caggctgcac ccatggcaga aggaggaggg
1141 cagaatcatc acgaagtggt gaagttcatg gatgtctatc agcgcagcta ctgccatcca
1201 atcgagaccc tggtggacat cttccaggag taccctgatg agatcgagta catcttcaag
1261 ccatcctgtg tgcccctgat gcgatgcggg ggctgctgca atgacgaggg cctggagtgt
1321 gtgcccactg aggagtccaa catcaccatg cagattatgc ggatcaaacc tcaccaaggc
1381 cagcacatag gagagatgag cttcctacag cacaacaaat gtgaatgcag accaaagaaa
1441 gatagagcaa gacaagaaaa aaaatcagtt cgaggaaagg gaaaggggca aaaacgaaag
1501 cgcaagaaat cccggtataa gtcctggagc gttccctgtg ggccttgctc agagcggaga
1561 aagcatttgt ttgtacaaga tccgcagacg tgtaaatgtt cctgcaaaaa cacagactcg
1621 cgttgcaagg cgaggcagct tgagttaaac gaacgtactt gcagatgtga caagccgagg
1681 cggtgagccg ggcaggagga aggagcctcc ctcagggttt cgggaaccag atctctcacc
1741 aggaaagact gatacagaac gatcgataca gaaaccacgc tgccgccacc acaccatcac
1801 catcgacaga acagtcctta atccagaaac ctgaaatgaa ggaagaggag actctgcgca
1861 gagcactttg ggtccggagg gcgagactcc ggcggaagca ttcccgggcg ggtgacccag
1921 cacggtccct cttggaattg gattcgccat tttatttttc ttgctgctaa atcaccgagc
1981 ccggaagatt agagagtttt atttctggga ttcctgtaga cacacccacc cacatacata
2041 catttatata tatatatatt atatatatat aaaaataaat atctctattt tatatatata
2101 aaatatatat attctttttt taaattaaca gtgctaatgt tattggtgtc ttcactggat
2161 gtatttgact gctgtggact tgagttggga ggggaatgtt cccactcaga tcctgacagg
2221 gaagaggagg agatgagaga ctctggcatg atcttttttt tgtcccactt ggtggggcca
2281 gggtcctctc ccctgcccag gaatgtgcaa ggccagggca tgggggcaaa tatgacccag
2341 ttttgggaac accgacaaac ccagccctgg cgctgagcct ctctacccca ggtcagacgg
2401 acagaaagac agatcacagg tacagggatg aggacaccgg ctctgaccag gagtttgggg
2461 agcttcagga cattgctgtg ctttggggat tccctccaca tgctgcacgc gcatctcgcc
2521 cccaggggca ctgcctggaa gattcaggag cctgggcggc cttcgcttac tctcacctgc
2581 ttctgagttg cccaggagac cactggcaga tgtcccggcg aagagaagag acacattgtt
```

-continued

```
2641 ggaagaagca gcccatgaca gctccccttc ctgggactcg ccctcatcct cttcctgctc
2701 cccttcctgg ggtgcagcct aaaaggacct atgtcctcac accattgaaa ccactagttc
2761 tgtcccccca ggagacctgg ttgtgtgtgt gtgagtggtt gaccttcctc catcccctgg
2821 tccttccctt cccttcccga ggcacagaga gacagggcag gatccacgtg cccattgtgg
2881 aggcagagaa aagagaaagt gttttatata cggtacttat ttaatatccc tttttaatta
2941 gaaattaaaa cagttaattt aattaaagag tagggttttt tttcagtatt cttggttaat
3001 atttaatttc aactatttat gagatgtatc ttttgctctc tcttgctctc ttatttgtac
3061 cggtttttgt atataaaatt catgtttcca atctctctct ccctgatcgg tgacagtcac
3121 tagcttatct tgaacagata tttaattttg ctaacactca gctctgccct ccccgatccc
3181 ctggctcccc agcacacatt cctttgaaat aaggtttcaa tatacatcta catactatat
3241 atatatttgg caacttgtat ttgtgtgtat atatatatat atatgtttat gtatatatgt
3301 gattctgata aaatagacat tgctattctg tttttatat gtaaaaacaa aacaagaaaa
3361 aatagagaat tctacatact aaatctctct cctttttttaa ttttaatatt tgttatcatt
3421 tatttattgg tgctactgtt tatccgtaat aattgtgggg aaaagatatt aacatcacgt
3481 ctttgtctct agtgcagttt ttcgagatat tccgtagtac atatttattt ttaaacaacg
3541 acaaagaaat acagatatat cttaaaaaaa aaaaagcatt ttgtattaaa gaatttaatt
3601 ctgatctcaa aaaaaaaaaa aaaaaa
```

In embodiments, a VEGF gene used in any composition and method described herein is a VEGF-A isoform c having the following nucleic acid sequence:

```
                                                           (SEQ ID NO: 3)
   1 tcgcggaggc ttggggcagc cgggtagctc ggaggtcgtg gcgctggggg ctagcaccag
  61 cgctctgtcg ggaggcgcag cggttaggtg gaccggtcag cggactcacc ggccagggcg
 121 ctcggtgctg gaatttgata ttcattgatc cgggttttat ccctcttctt ttttcttaaa
 181 catttttttt taaaactgta ttgtttctcg ttttaattta tttttgcttg ccattcccca
 241 cttgaatcgg gccgacggct tggggagatt gctctacttc cccaaatcac tgtggatttt
 301 ggaaaccagc agaaagagga aagaggtagc aagagctcca gagagaagtc gaggaagaga
 361 gagacggggt cagagagagc gcgcgggcgt gcgagcagcg aaagcgacag gggcaaagtg
 421 agtgacctgc ttttgggggt gaccgccgga gcgcggcgtg agccctcccc cttgggatcc
 481 cgcagctgac cagtcgcgct gacggacaga cagacagaca ccgcccccag ccccagctac
 541 cacctcctcc ccggccggcg gcggacagtg gacgcggcgg cgagccgcgg gcaggggccg
 601 gagcccgcgc ccggaggcgg ggtggagggg gtcggggctc gcggcgtcgc actgaaactt
 661 ttcgtccaac ttctgggctg ttctcgcttc ggaggagccg tggtccgcgc gggggaagcc
 721 gagccgagcg gagccgcgag aagtgctagc tcgggccggg aggagccgca gccggaggag
 781 ggggaggagg aagaagagaa ggaagaggag agggggccgc agtggcgact cggcgctcgg
 841 aagccgggct catggacggg tgaggcggcg gtgtgcgcag acagtgctcc agccgcgcgc
 901 gctccccagg ccctggcccg ggcctcgggc cggggaggaa gagtagctcg ccgaggcgcc
 961 gaggagagcg ggccgcccca cagcccgagc cggagaggga gcgcgagccg cgccggcccc
1021 ggtcgggcct ccgaaaccat gaactttctg ctgtcttggg tgcattggag ccttgccttg
1081 ctgctctacc tccaccatgc caagtggtcc caggctgcac ccatggcaga aggaggaggg
1141 cagaatcatc acgaagtggt gaagttcatg gatgtctatc agcgcagcta ctgccatcca
```

-continued

```
1201 atcgagaccc tggtggacat cttccaggag taccctgatg agatcgagta catcttcaag
1261 ccatcctgtg tgcccctgat gcgatgcggg ggctgctgca atgacgaggg cctggagtgt
1321 gtgcccactg aggagtccaa catcaccatg cagattatgc ggatcaaacc tcaccaaggc
1381 cagcacatag gagagatgag cttcctacag cacaacaaat gtgaatgcag accaaagaaa
1441 gatagagcaa gacaagaaaa aaaatcagtt cgaggaaagg gaaaggggca aaaacgaaag
1501 cgcaagaaat cccgtccctg tgggccttgc tcagagcgga gaaagcattt gtttgtacaa
1561 gatccgcaga cgtgtaaatg ttcctgcaaa aacacagact cgcgttgcaa ggcgaggcag
1621 cttgagttaa acgaacgtac ttgcagatgt gacaagccga ggcggtgagc cgggcaggag
1681 gaaggagcct ccctcagggt ttcgggaacc agatctctca ccaggaaaga ctgatacaga
1741 acgatcgata cagaaaccac gctgccgcca ccacaccatc accatcgaca gaacagtcct
1801 taatccagaa acctgaaatg aaggaagagg agactctgcg cagagcactt tgggtccgga
1861 gggcgagact ccggcggaag cattcccggg cgggtgaccc agcacggtcc ctcttggaat
1921 tggattcgcc attttatttt tcttgctgct aaatcaccga gcccggaaga ttagagagtt
1981 ttatttctgg gattcctgta gacacaccca cccacataca tacatttata tatatatata
2041 ttatatatat ataaaaataa atatctctat tttatatata taaaatatat atattctttt
2101 tttaaattaa cagtgctaat gttattggtg tcttcactgg atgtatttga ctgctgtgga
2161 cttgagttgg gaggggaatg ttcccactca gatcctgaca gggaagagga ggagatgaga
2221 gactctggca tgatcttttt tttgtcccac ttggtggggc cagggtcctc tcccctgccc
2281 aggaatgtgc aaggccaggg catgggggca aatatgaccc agttttggga acaccgacaa
2341 acccagccct ggcgctgagc ctctctaccc caggtcagac ggacagaaag acagatcaca
2401 ggtacaggga tgaggacacc ggctctgacc aggagtttgg ggagcttcag gacattgctg
2461 tgctttgggg attccctcca catgctgcac gcgcatctcg cccccagggg cactgcctgg
2521 aagattcagg agcctgggcg gccttcgctt actctcacct gcttctgagt tgcccaggag
2581 accactggca gatgtcccgg cgaagagaag agacacattg ttggaagaag cagcccatga
2641 cagctcccct tcctgggact cgccctcatc ctcttcctgc tccccttcct ggggtgcagc
2701 ctaaaaggac ctatgtcctc acaccattga aaccactagt tctgtccccc caggagacct
2761 ggttgtgtgt gtgtgagtgg ttgaccttcc tccatcccct ggtccttccc ttcccttccc
2821 gaggcacaga gagacagggc aggatccacg tgcccattgt ggaggcagag aaaagagaaa
2881 gtgttttata tacggtactt atttaatatc cctttttaat tagaaattaa aacagttaat
2941 ttaattaaag agtagggttt tttttcagta ttcttggtta atatttaatt tcaactattt
3001 atgagatgta tcttttgctc tctcttgctc tcttatttgt accggttttt gtatataaaa
3061 ttcatgtttc caatctctct ctccctgatc ggtgacagtc actagcttat cttgaacaga
3121 tatttaattt tgctaacact cagctctgcc ctccccgatc ccctggctcc ccagcacaca
3181 ttcctttgaa ataaggtttc aatatacatc tacatactat atatatattt ggcaacttgt
3241 atttgtgtgt atatatatat atatatgttt atgtatatat gtgattctga taaaatagac
3301 attgctattc tgttttttat atgtaaaaac aaaacaagaa aaaatagaga attctacata
3361 ctaaatctct ctcctttttt aattttaata tttgttatca tttatttatt ggtgctactg
3421 tttatccgta ataattgtgg ggaaaagata ttaacatcac gtctttgtct ctagtgcagt
```

-continued

```
3481 ttttcgagat attccgtagt acatatttat ttttaaacaa cgacaaagaa atacagatat
3541 atcttaaaaa aaaaaaagca ttttgtatta aagaatttaa ttctgatctc aaaaaaaaaa
3601 aaaaaaaa
```

In embodiments, a VEGF gene used in any composition and method described herein is a VEGF-A isoform d having the following nucleic acid sequence:

```
                                                        (SEQ ID NO: 4)
   1 tcgcggaggc ttggggcagc cgggtagctc ggaggtcgtg gcgctggggg ctagcaccag
  61 cgctctgtcg ggaggcgcag cggttaggtg gaccggtcag cggactcacc ggccagggcg
 121 ctcggtgctg gaatttgata ttcattgatc cgggttttat ccctcttctt ttttcttaaa
 181 cattttttt taaaactgta ttgtttctcg ttttaattta tttttgcttg ccattcccca
 241 cttgaatcgg gccgacggct tggggagatt gctctacttc cccaaatcac tgtggatttt
 301 ggaaaccagc agaaagagga aagaggtagc aagagctcca gagagaagtc gaggaagaga
 361 gagacggggt cagagagagc gcgcgggcgt gcgagcagcg aaagcgacag gggcaaagtg
 421 agtgacctgc ttttgggggt gaccgccgga gcgcggcgtg agccctcccc cttgggatcc
 481 cgcagctgac cagtcgcgct gacggacaga cagacagaca ccgcccccag ccccagctac
 541 cacctcctcc ccggccggcg gcggacagtg gacgcggcgg cgagccgcgg gcaggggccg
 601 gagcccgcgc ccggaggcgg ggtggagggg gtcggggctc gcggcgtcgc actgaaactt
 661 ttcgtccaac ttctgggctg ttctcgcttc ggaggagccg tggtccgcgc gggggaagcc
 721 gagccgagcg gagccgcgag aagtgctagc tcgggccggg aggagccgca gccggaggag
 781 ggggaggagg aagaagagaa ggaagaggag agggggccgc agtggcgact cggcgctcgg
 841 aagccgggct catggacggg tgaggcggcg gtgtgcgcag acagtgctcc agccgcgcgc
 901 gctccccagg ccctggcccg ggcctcgggc cggggaggaa gagtagctcg ccgaggcgcc
 961 gaggagagcg ggccgcccca cagcccgagc cggagaggga gcgcgagccg cgccggcccc
1021 ggtcgggcct ccgaaaccat gaactttctg ctgtcttggg tgcattggag ccttgccttg
1081 ctgctctacc tccaccatgc caagtggtcc caggctgcac ccatggcaga aggaggaggg
1141 cagaatcatc acgaagtggt gaagttcatg gatgtctatc agcgcagcta ctgccatcca
1201 atcgagaccc tggtggacat cttccaggag taccctgatg agatcgagta catcttcaag
1261 ccatcctgtg tgcccctgat gcgatgcggg ggctgctgca atgacgaggg cctggagtgt
1321 gtgcccactg aggagtccaa catcaccatg cagattatgc ggatcaaacc tcaccaaggc
1381 cagcacatag gagagatgag cttcctacag cacaacaaat gtgaatgcag accaaagaaa
1441 gatagagcaa gacaagaaaa tccctgtggg ccttgctcag agcggagaaa gcatttgttt
1501 gtacaagatc cgcagacgtg taaatgttcc tgcaaaaaca cagactcgcg ttgcaaggcg
1561 aggcagcttg agttaaacga acgtacttgc agatgtgaca agccgaggcg gtgagccggg
1621 caggaggaag gagcctccct cagggtttcg ggaaccagat ctctcaccag gaaagactga
1681 tacagaacga tcgatacaga aaccacgctg ccgccaccac accatcacca tcgacagaac
1741 agtccttaat ccagaaacct gaaatgaagg aagaggagac tctgcgcaga gcactttggg
1801 tccggagggc gagactccgg cggaagcatt cccgggcggg tgacccagca cggtccctct
1861 tggaattgga ttcgccattt tatttttctt gctgctaaat caccgagccc ggaagattag
1921 agagttttat ttctgggatt cctgtagaca cacccaccca catacataca tttatatata
```

-continued

```
1981 tatatattat atatatataa aaataaatat ctctatttta tatatataaa atatatatat

2041 tctttttttta aattaacagt gctaatgtta ttggtgtctt cactggatgt atttgactgc

2101 tgtggacttg agttgggagg ggaatgttcc cactcagatc ctgacaggga agaggaggag

2161 atgagagact ctggcatgat cttttttttg tcccacttgg tggggccagg gtcctctccc

2221 ctgcccagga atgtgcaagg ccagggcatg ggggcaaata tgacccagtt ttgggaacac

2281 cgacaaaccc agccctggcg ctgagcctct ctaccccagg tcagacggac agaaagacag

2341 atcacaggta cagggatgag gacaccggct ctgaccagga gtttggggag cttcaggaca

2401 ttgctgtgct ttggggattc cctccacatg ctgcacgcgc atctcgcccc caggggcact

2461 gcctggaaga ttcaggagcc tgggcggcct tcgcttactc tcacctgctt ctgagttgcc

2521 caggagacca ctggcagatg tcccggcgaa gagaagagac acattgttgg aagaagcagc

2581 ccatgacagc tccccttcct gggactcgcc ctcatcctct tcctgctccc cttcctgggg

2641 tgcagcctaa aaggacctat gtcctcacac cattgaaacc actagttctg tccccccagg

2701 agacctggtt gtgtgtgtgt gagtggttga ccttcctcca tcccctggtc cttcccttcc

2761 cttcccgagg cacagagaga cagggcagga tccacgtgcc cattgtggag gcagagaaaa

2821 gagaaagtgt tttatatacg gtacttattt aatatccctt tttaattaga aattaaaaca

2881 gttaatttaa ttaaagagta gggttttttt tcagtattct tggttaatat ttaatttcaa

2941 ctatttatga gatgtatctt ttgctctctc ttgctctctt atttgtaccg gtttttgtat

3001 ataaaattca tgtttccaat ctctctctcc ctgatcggtg acagtcacta gcttatcttg

3061 aacagatatt taattttgct aacactcagc tctgccctcc ccgatcccct ggctccccag

3121 cacacattcc tttgaaataa ggtttcaata tacatctaca tactatatat atatttggca

3181 acttgtattt gtgtgtatat atatatatat atgtttatgt atatatgtga ttctgataaa

3241 atagacattg ctattctgtt ttttatatgt aaaaacaaaa caagaaaaaa tagagaattc

3301 tacatactaa atctctctcc ttttttaatt ttaatatttg ttatcattta tttattggtg

3361 ctactgttta tccgtaataa ttgtggggaa aagatattaa catcacgtct ttgtctctag

3421 tgcagttttt cgagatattc cgtagtacat atttattttt aaacaacgac aaagaaatac

3481 agatatatct taaaaaaaaa aaagcatttt gtattaaaga atttaattct gatctcaaaa

3541 aaaaaaaaaa aaaa
```

In embodiments, a VEGF gene used in any composition and method described herein is a VEGF-A isoform e having the following nucleic acid sequence:

```
                                              (SEQ ID NO: 5)
  1 tcgcggaggc ttggggcagc cgggtagctc ggaggtcgtg gcgctggggg ctagcaccag

 61 cgctctgtcg ggaggcgcag cggttaggtg gaccggtcag cggactcacc ggccagggcg

121 ctcggtgctg gaatttgata ttcattgatc cgggttttat ccctcttctt ttttcttaaa

181 cattttttttt taaaactgta ttgtttctcg ttttaattta tttttgcttg ccattcccca

241 cttgaatcgg gccgacggct tggggagatt gctctacttc cccaaatcac tgtggatttt

301 ggaaaccagc agaaagagga aagaggtagc aagagctcca gagagaagtc gaggaagaga

361 gagacggggt cagagagagc gcgcgggcgt gcgagcagcg aaagcgacag gggcaaagtg

421 agtgacctgc ttttgggggt gaccgccgga gcgcggcgtg agccctcccc cttgggatcc

481 cgcagctgac cagtcgcgct gacggacaga cagacagaca ccgcccccag ccccagctac

541 cacctcctcc ccggccggcg gcggacagtg gacgcggcgg cgagccgcgg gcaggggccg
```

-continued

```
 601 gagcccgcgc ccggaggcgg ggtggagggg gtcggggctc gcggcgtcgc actgaaactt
 661 ttcgtccaac ttctgggctg ttctcgcttc ggaggagccg tggtccgcgc gggggaagcc
 721 gagccgagcg gagccgcgag aagtgctagc tcgggccggg aggagccgca gccggaggag
 781 ggggaggagg aagaagagaa ggaagaggag agggggccgc agtggcgact cggcgctcgg
 841 aagccgggct catggacggg tgaggcggcg gtgtgcgcag acagtgctcc agccgcgcgc
 901 gctccccagg ccctggcccg ggcctcgggc cggggaggaa gagtagctcg ccgaggcgcc
 961 gaggagagcg ggccgcccca cagcccgagc cggagaggga gcgcgagccg cgccggcccc
1021 ggtcgggcct ccgaaaccat gaactttctg ctgtcttggg tgcattggag ccttgccttg
1081 ctgctctacc tccaccatgc caagtggtcc caggctgcac ccatggcaga aggaggaggg
1141 cagaatcatc acgaagtggt gaagttcatg gatgtctatc agcgcagcta ctgccatcca
1201 atcgagaccc tggtggacat cttccaggag taccctgatg agatcgagta catcttcaag
1261 ccatcctgtg tgcccctgat gcgatgcggg ggctgctgca atgacgaggg cctggagtgt
1321 gtgcccactg aggagtccaa catcaccatg cagattatgc ggatcaaacc tcaccaaggc
1381 cagcacatag gagagatgag cttcctacag cacaacaaat gtgaatgcag accaaagaaa
1441 gatagagcaa gacaagaaaa tccctgtggg ccttgctcag agcggagaaa gcatttgttt
1501 gtacaagatc cgcagacgtg taaatgttcc tgcaaaaaca cagactcgcg ttgcaagatg
1561 tgacaagccg aggcggtgag ccgggcagga ggaaggagcc tccctcaggg tttcgggaac
1621 cagatctctc accaggaaag actgatacag aacgatcgat acagaaacca cgctgccgcc
1681 accacaccat caccatcgac agaacagtcc ttaatccaga aacctgaaat gaaggaagag
1741 gagactctgc gcagagcact ttgggtccgg agggcgagac tccggcggaa gcattcccgg
1801 gcgggtgacc cagcacggtc cctcttggaa ttggattcgc cattttattt ttcttgctgc
1861 taaatcaccg agcccggaag attagagagt tttatttctg ggattcctgt agacacaccc
1921 acccacatac atacatttat atatatatat attatatata tataaaaata aatatctcta
1981 ttttatatat ataaaatata tatattcttt ttttaaatta acagtgctaa tgttattggt
2041 gtcttcactg gatgtatttg actgctgtgg acttgagttg ggaggggaat gttcccactc
2101 agatcctgac agggaagagg aggagatgag agactctggc atgatctttt ttttgtccca
2161 cttggtgggg ccagggtcct ctcccctgcc caggaatgtg caaggccagg gcatgggggc
2221 aaatatgacc cagttttggg aacaccgaca aacccagccc tggcgctgag cctctctacc
2281 ccaggtcaga cggacagaaa gacagatcac aggtacaggg atgaggacac cggctctgac
2341 caggagtttg gggagcttca ggacattgct gtgctttggg gattccctcc acatgctgca
2401 cgcgcatctc gcccccaggg gcactgcctg gaagattcag gagcctgggc ggccttcgct
2461 tactctcacc tgcttctgag ttgcccagga gaccactggc agatgtcccg gcgaagagaa
2521 gagacacatt gttggaagaa gcagcccatg acagctcccc ttcctgggac tcgccctcat
2581 cctcttcctg ctccccttcc tggggtgcag cctaaaagga cctatgtcct cacaccattg
2641 aaaccactag ttctgtcccc ccaggagacc tggttgtgtg tgtgtgagtg gttgaccttc
2701 ctccatcccc tggtccttcc cttcccttcc cgaggcacag agagacaggg caggatccac
2761 gtgcccattg tggaggcaga gaaaagagaa agtgttttat atacggtact tatttaatat
2821 ccctttttaa ttagaaatta aaacagttaa tttaattaaa gagtagggtt tttttcagt
2881 attcttggtt aatatttaat ttcaactatt tatgagatgt atcttttgct ctctcttgct
2941 ctcttatttg taccggtttt tgtatataaa attcatgttt ccaatctctc tctccctgat
```

-continued

```
3001 cggtgacagt cactagctta tcttgaacag atatttaatt ttgctaacac tcagctctgc
3061 cctccccgat cccctggctc cccagcacac attcctttga aataaggttt caatatacat
3121 ctacatacta tatatatatt tggcaacttg tatttgtgtg tatatatata tatatatgtt
3181 tatgtatata tgtgattctg ataaaataga cattgctatt ctgtttttta tatgtaaaaa
3241 caaaacaaga aaaaatagag aattctacat actaaatctc tctccttttt taattttaat
3301 atttgttatc atttatttat tggtgctact gtttatccgt aataattgtg gggaaaagat
3361 attaacatca cgtctttgtc tctagtgcag tttttcgaga tattccgtag tacatattta
3421 tttttaaaca acgacaaaga aatacagata tatcttaaaa aaaaaaaagc attttgtatt
3481 aaagaattta attctgatct caaaaaaaaa aaaaaaaaa
```

In embodiments, a VEGF gene used in any composition and method described herein is a VEGF-A isoform f having the following nucleic acid sequence:

```
                                                               (SEQ ID NO: 6)
   1 tcgcggaggc ttggggcagc cgggtagctc ggaggtcgtg gcgctggggg ctagcaccag
  61 cgctctgtcg ggaggcgcag cggttaggtg gaccggtcag cggactcacc ggccagggcg
 121 ctcggtgctg gaatttgata ttcattgatc cgggttttat ccctcttctt ttttcttaaa
 181 catttttttt taaaactgta ttgtttctcg ttttaattta tttttgcttg ccattcccca
 241 cttgaatcgg gccgacggct tggggagatt gctctacttc cccaaatcac tgtggatttt
 301 ggaaaccagc agaaagagga aagaggtagc aagagctcca gagagaagtc gaggaagaga
 361 gagacggggt cagagagagc gcgcgggcgt gcgagcagcg aaagcgacag gggcaaagtg
 421 agtgacctgc ttttgggggt gaccgccgga gcgcggcgtg agccctcccc cttgggatcc
 481 cgcagctgac cagtcgcgct gacggacaga cagacagaca ccgcccccag ccccagctac
 541 cacctcctcc ccggccggcg gcggacagtg gacgcggcgg cgagccgcgg gcaggggccg
 601 gagcccgcgc ccggaggcgg ggtggagggg gtcggggctc gcggcgtcgc actgaaactt
 661 ttcgtccaac ttctgggctg ttctcgcttc ggaggagccg tggtccgcgc gggggaagcc
 721 gagccgagcg gagccgcgag aagtgctagc tcgggccggg aggagccgca gccggaggag
 781 ggggaggagg aagaagagaa ggaagaggag agggggccgc agtggcgact cggcgctcgg
 841 aagccgggct catggacggg tgaggcggcg gtgtgcgcag acagtgctcc agccgcgcgc
 901 gctccccagg ccctggcccg ggcctcgggc cggggaggaa gagtagctcg ccgaggcgcc
 961 gaggagagcg ggccgcccca cagcccgagc cggagaggga gcgcgagccg cgccggcccc
1021 ggtcgggcct ccgaaaccat gaactttctg ctgtcttggg tgcattggag ccttgccttg
1081 ctgctctacc tccaccatgc caagtggtcc caggctgcac ccatggcaga aggaggaggg
1141 cagaatcatc acgaagtggt gaagttcatg gatgtctatc agcgcagcta ctgccatcca
1201 atcgagaccc tggtggacat cttccaggag taccctgatg agatcgagta catcttcaag
1261 ccatcctgtg tgcccctgat gcgatgcggg ggctgctgca atgacgaggg cctggagtgt
1321 gtgcccactg aggagtccaa catcaccatg cagattatgc ggatcaaacc tcaccaaggc
1381 cagcacatag gagagatgag cttcctacag cacaacaaat gtgaatgcag accaaagaaa
1441 gatagagcaa gacaagaaaa atgtgacaag ccgaggcggt gagccgggca ggaggaagga
1501 gcctccctca gggtttcggg aaccagatct ctcaccagga aagactgata cagaacgatc
1561 gatacagaaa ccacgctgcc gccaccacac catcaccatc gacagaacag tccttaatcc
1621 agaaacctga aatgaaggaa gaggagactc tgcgcagagc actttgggtc cggagggcga
```

-continued 1681 gactccggcg gaagcattcc cgggcgggtg acccagcacg gtccctcttg gaattggatt 1741 cgccatttta tttttcttgc tgctaaatca ccgagcccgg aagattagag agttttattt 1801 ctgggattcc tgtagacaca cccacccaca tacatacatt tatatatata tatattatat 1861 atatataaaa ataaatatct ctattttata tatataaaat atatatattc tttttttaaa 1921 ttaacagtgc taatgttatt ggtgtcttca ctggatgtat ttgactgctg tggacttgag 1981 ttgggagggg aatgttccca ctcagatcct gacagggaag aggaggagat gagagactct 2041 ggcatgatct ttttttgtc ccacttggtg gggccagggt cctctcccct gcccaggaat 2101 gtgcaaggcc agggcatggg ggcaaatatg acccagtttt gggaacaccg acaaacccag 2161 ccctggcgct gagcctctct accccaggtc agacggacag aaagacagat cacaggtaca 2221 gggatgagga caccggctct gaccaggagt ttggggagct tcaggacatt gctgtgcttt 2281 ggggattccc tccacatgct gcacgcgcat ctcgccccca ggggcactgc ctggaagatt 2341 caggagcctg ggcggccttc gcttactctc acctgcttct gagttgccca ggagaccact 2401 ggcagatgtc ccggcgaaga gaagagacac attgttggaa gaagcagccc atgacagctc 2461 cccttcctgg gactcgccct catcctcttc ctgctcccct tcctggggtg cagcctaaaa 2521 ggacctatgt cctcacacca ttgaaaccac tagttctgtc cccccaggag acctggttgt 2581 gtgtgtgtga gtggttgacc ttcctccatc ccctggtcct tcccttccct tcccgaggca 2641 cagagagaca gggcaggatc cacgtgccca ttgtggaggc agagaaaaga gaaagtgttt 2701 tatatacggt acttatttaa tatccctttt taattagaaa ttaaaacagt taatttaatt 2761 aaagagtagg gtttttttc agtattcttg gttaatattt aatttcaact atttatgaga 2821 tgtatctttt gctctctctt gctctcttat ttgtaccggt ttttgtatat aaaattcatg 2881 tttccaatct ctctctccct gatcggtgac agtcactagc ttatcttgaa cagatattta 2941 attttgctaa cactcagctc tgccctcccc gatcccctgg ctccccagca cacattcctt 3001 tgaaataagg tttcaatata catctacata ctatatatat atttggcaac ttgtatttgt 3061 gtgtatatat atatatatat gtttatgtat atatgtgatt ctgataaaat agacattgct 3121 attctgtttt ttatatgtaa aaacaaaaca agaaaaaata gagaattcta catactaaat 3181 ctctctcctt ttttaatttt aatatttgtt atcatttatt tattggtgct actgtttatc 3241 cgtaataatt gtggggaaaa gatattaaca tcacgtcttt gtctctagtg cagtttttcg 3301 agatattccg tagtacatat ttatttttaa acaacgacaa agaaatacag atatatctta 3361 aaaaaaaaaa agcattttgt attaaagaat ttaattctga tctcaaaaaa aaaaaaaaaa 3421 aa In embodiments, a VEGF gene used in any composition and method described herein is a VEGF-A isoform g having the following nucleic acid sequence:

(SEQ ID NO: 7)

1 tcgcggaggc ttggggcagc cgggtagctc ggaggtcgtg gcgctggggg ctagcaccag 61 cgctctgtcg ggaggcgcag cggttaggtg gaccggtcag cggactcacc ggccagggcg 121 ctcggtgctg gaatttgata ttcattgatc cgggttttat ccctcttctt ttttcttaaa 181 cattttttt taaaactgta ttgtttctcg ttttaattta tttttgcttg ccattcccca 241 cttgaatcgg gccgacggct tggggagatt gctctacttc cccaaatcac tgtggatttt 301 ggaaaccagc agaaagagga aagaggtagc aagagctcca gagagaagtc gaggaagaga -continued

```
361 gagacggggt cagagagagc gcgcgggcgt gcgagcagcg aaagcgacag gggcaaagtg
421 agtgacctgc ttttgggggt gaccgccgga gcgcggcgtg agccctcccc cttgggatcc
481 cgcagctgac cagtcgcgct gacggacaga cagacagaca ccgcccccag ccccagctac
541 cacctcctcc ccggccggcg gcggacagtg gacgcggcgg cgagccgcgg gcaggggccg
601 gagcccgcgc ccggaggcgg ggtggagggg gtcggggctc gcggcgtcgc actgaaactt
661 ttcgtccaac ttctgggctg ttctcgcttc ggaggagccg tggtccgcgc gggggaagcc
721 gagccgagcg gagccgcgag aagtgctagc tcgggccggg aggagccgca gccggaggag
781 ggggaggagg aagaagagaa ggaagaggag agggggccgc agtggcgact cggcgctcgg
841 aagccgggct catggacggg tgaggcggcg gtgtgcgcag acagtgctcc agccgcgcgc
901 gctccccagg ccctggcccg ggcctcgggc cggggaggaa gagtagctcg ccgaggcgcc
961 gaggagagcg ggccgcccca cagcccgagc cggagaggga gcgcgagccg cgccggcccc
1021 ggtcgggcct ccgaaaccat gaactttctg ctgtcttggg tgcattggag ccttgccttg
1081 ctgctctacc tccaccatgc caagtigtcc caggctgcac ccatggcaga aggaggaggg
1141 cagaatcatc acgaagtggt gaagttcatg gatgtctatc agcgcagcta ctgccatcca
1201 atcgagaccc tggtggacat cttccaggag taccctgatg agatcgagta catcttcaag
1261 ccatcctgtg tgcccctgat gcgatgcggg ggctgctgca atgacgaggg cctggagtgt
1321 gtgcccactg aggagtccaa catcaccatg cagattatgc ggatcaaacc tcaccaaggc
1381 cagcacatag gagagatgag cttcctacag cacaacaaat gtgaatgcag accaaagaaa
1441 gatagagcaa gacaagaaaa tccctgtggg ccttgctcag agcggagaaa gcatttgttt
1501 gtacaagatc cgcagacgtg taaatgttcc tgcaaaaaca cagactcgcg ttgcaaggcg
1561 aggcagcttg agttaaacga acgtacttgc agatctctca ccaggaaaga ctgatacaga
1621 acgatcgata cagaaaccac gctgccgcca ccacaccatc accatcgaca gaacagtcct
1681 taatccagaa acctgaaatg aaggaagagg agactctgcg cagagcactt tgggtccgga
1741 gggcgagact ccggcggaag cattcccggg cgggtgaccc agcacggtcc ctcttggaat
1801 tggattcgcc attttatttt tcttgctgct aaatcaccga gcccggaaga ttagagagtt
1861 ttatttctgg gattcctgta gacacaccca cccacataca tacatttata tatatatata
1921 ttatatatat ataaaaataa atatctctat tttatatata taaaatatat atattctttt
1981 tttaaattaa cagtgctaat gttattggtg tcttcactgg atgtatttga ctgctgtgga
2041 cttgagttgg gaggggaatg ttcccactca gatcctgaca gggaagagga ggagatgaga
2101 gactctggca tgatcttttt tttgtcccac ttggtggggc cagggtcctc tcccctgccc
2161 aggaatgtgc aaggccaggg catgggggca aatatgaccc agttttggga acaccgacaa
2221 acccagccct ggcgctgagc ctctctaccc caggtcagac ggacagaaag acagatcaca
2281 ggtacaggga tgaggacacc ggctctgacc aggagtttgg ggagcttcag gacattgctg
2341 tgctttgggg attccctcca catgctgcac gcgcatctcg cccccagggg cactgcctgg
2401 aagattcagg agcctgggcg gccttcgctt actctcacct gcttctgagt tgcccaggag
2461 accactggca gatgtcccgg cgaagagaag agacacattg ttggaagaag cagcccatga
2521 cagctcccct tcctgggact cgccctcatc ctcttcctgc tccccttcct ggggtgcagc
2581 ctaaaaggac ctatgtcctc acaccattga aaccactagt tctgtccccc caggagacct
2641 ggttgtgtgt gtgtgagtgg ttgaccttcc tccatcccct ggtccttccc ttcccttccc
2701 gaggcacaga gagacagggc aggatccacg tgcccattgt ggaggcagag aaaagagaaa
2761 gtgttttata tacggtactt atttaatatc cctttttaat tagaaattaa aacagttaat
```

-continued

```
2821 ttaattaaag agtagggttt tttttcagta ttcttggtta atatttaatt tcaactattt
2881 atgagatgta tcttttgctc tctcttgctc tcttatttgt accggttttt gtatataaaa
2941 ttcatgtttc caatctctct ctccctgatc ggtgacagtc actagcttat cttgaacaga
3001 tatttaattt tgctaacact cagctctgcc ctccccgatc ccctggctcc ccagcacaca
3061 ttcctttgaa ataaggtttc aatatacatc tacatactat atatatattt ggcaacttgt
3121 atttgtgtgt atatatatat atatatgttt atgtatatat gtgattctga taaaatagac
3181 attgctattc tgttttttat atgtaaaaac aaaacaagaa aaaatagaga attctacata
3241 ctaaatctct ctcctttttt aattttaata tttgttatca tttatttatt ggtgctactg
3301 tttatccgta ataattgtgg ggaaaagata ttaacatcac gtctttgtct ctagtgcagt
3361 ttttcgagat attccgtagt acatatttat ttttaaacaa cgacaaagaa atacagatat
3421 atcttaaaaa aaaaaaagca ttttgtatta aagaatttaa ttctgatctc aaaaaaaaaa
3481 aaaaaaaa
```

In embodiments, a VEGF gene used in any composition and method described herein is a VEGF-A isoform h having the following nucleic acid sequence:

```
                                                         (SEQ ID NO: 8)
   1 tcgcggaggc ttggggcagc cgggtagctc ggaggtcgtg gcgctggggg ctagcaccag
  61 cgctctgtcg ggaggcgcag cggttaggtg gaccggtcag cggactcacc ggccagggcg
 121 ctcggtgctg gaatttgata ttcattgatc cgggttttat ccctcttctt ttttcttaaa
 181 catttttttt taaaactgta ttgtttctcg ttttaattta tttttgcttg ccattcccca
 241 cttgaatcgg gccgacggct tggggagatt gctctacttc cccaaatcac tgtggatttt
 301 ggaaaccagc agaaagagga aagaggtagc aagagctcca gagagaagtc gaggaagaga
 361 gagacggggt cagagagagc gcgcgggcgt gcgagcagcg aaagcgacag gggcaaagtg
 421 agtgacctgc ttttgggggt gaccgccgga gcgcggcgtg agccctcccc cttgggatcc
 481 cgcagctgac cagtcgcgct gacggacaga cagacagaca ccgcccccag ccccagctac
 541 cacctcctcc ccggccggcg gcggacagtg gacgcggcgg cgagccgcgg gcaggggccg
 601 gagcccgcgc ccggaggcgg ggtggagggg gtcggggctc gcggcgtcgc actgaaactt
 661 ttcgtccaac ttctgggctg ttctcgcttc ggaggagccg tggtccgcgc gggggaagcc
 721 gagccgagcg gagccgcgag aagtgctagc tcgggccggg aggagccgca gccggaggag
 781 ggggaggagg aagaagagaa ggaagaggag agggggccgc agtggcgact cggcgctcgg
 841 aagccgggct catggacggg tgaggcggcg gtgtgcgcag acagtgctcc agccgcgcgc
 901 gctccccagg ccctggcccg ggcctcgggc cggggaggaa gagtagctcg ccgaggcgcc
 961 gaggagagcg ggccgcccca cagcccgagc cggagaggga gcgcgagccg cgccggcccc
1021 ggtcgggcct ccgaaaccat gaactttctg ctgtcttggg tgcattggag ccttgccttg
1081 ctgctctacc tccaccatgc caagtggtcc caggctgcac ccatggcaga aggaggaggg
1141 cagaatcatc acgaagtggt gaagttcatg gatgtctatc agcgcagcta ctgccatcca
1201 atcgagaccc tggtggacat cttccaggag taccctgatg agatcgagta catcttcaag
1261 ccatcctgtg tgcccctgat gcgatgcggg ggctgctgca atgacgaggg cctggagtgt
1321 gtgcccactg aggagtccaa catcaccatg cagattatgc ggatcaaacc tcaccaaggc
1381 cagcacatag gagagatgag cttcctacag cacaacaaat gtgaatgcag atgtgacaag
```

-continued

```
1441 ccgaggcggt gagccgggca ggaggaagga gcctccctca gggtttcggg aaccagatct
1501 ctcaccagga aagactgata cagaacgatc gatacagaaa ccacgctgcc gccaccacac
1561 catcaccatc gacagaacag tccttaatcc agaaacctga aatgaaggaa gaggagactc
1621 tgcgcagagc actttgggtc cggagggcga gactccggcg gaagcattcc cgggcgggtg
1681 acccagcacg gtccctcttg gaattggatt cgccatttta tttttcttgc tgctaaatca
1741 ccgagcccgg aagattagag agttttattt ctgggattcc tgtagacaca cccacccaca
1801 tacatacatt tatatatata tatattatat atatataaaa ataaatatct ctattttata
1861 tatataaaat atatatattc tttttttaaa ttaacagtgc taatgttatt ggtgtcttca
1921 ctggatgtat ttgactgctg tggacttgag ttgggagggg aatgttccca ctcagatcct
1981 gacagggaag aggaggagat gagagactct ggcatgatct tttttttgtc ccacttggtg
2041 gggccagggt cctctcccct gcccaggaat gtgcaaggcc agggcatggg ggcaaatatg
2101 acccagtttt gggaacaccg acaaacccag ccctggcgct gagcctctct accccaggtc
2161 agacggacag aaagacagat cacaggtaca gggatgagga caccggctct gaccaggagt
2221 ttggggagct tcaggacatt gctgtgcttt ggggattccc tccacatgct gcacgcgcat
2281 ctcgccccca ggggcactgc ctggaagatt caggagcctg ggcggccttc gcttactctc
2341 acctgcttct gagttgccca ggagaccact ggcagatgtc ccggcgaaga gaagagacac
2401 attgttggaa gaagcagccc atgacagctc cccttcctgg gactcgccct catcctcttc
2461 ctgctcccct tcctggggtg cagcctaaaa ggacctatgt cctcacacca ttgaaaccac
2521 tagttctgtc cccccaggag acctggttgt gtgtgtgtga gtggttgacc ttcctccatc
2581 ccctggtcct tcccttccct tcccgaggca cagagagaca gggcaggatc cacgtgccca
2641 ttgtggaggc agagaaaaga gaaagtgttt tatatacggt acttatttaa tatccctttt
2701 taattagaaa ttaaaacagt taatttaatt aaagagtagg gtttttttc agtattcttg
2761 gttaatattt aatttcaact atttatgaga tgtatctttt gctctctctt gctctcttat
2821 ttgtaccggt tttgtatat aaaattcatg tttccaatct ctctctccct gatcggtgac
2881 agtcactagc ttatcttgaa cagatattta attttgctaa cactcagctc tgccctcccc
2941 gatcccctgg ctccccagca cacattcctt tgaaataagg tttcaatata catctacata
3001 ctatatatat atttggcaac ttgtatttgt gtgtatatat atatatatat gtttatgtat
3061 atatgtgatt ctgataaaat agacattgct attctgtttt ttatatgtaa aaacaaaaca
3121 agaaaaaata gagaattcta catactaaat ctctctcctt ttttaatttt aatatttgtt
3181 atcatttatt tattggtgct actgtttatc cgtaataatt gtggggaaaa gatattaaca
3241 tcacgtcttt gtctctagtg cagtttttcg agatattccg tagtacatat ttatttttaa
3301 acaacgacaa agaaatacag atatatctta aaaaaaaaaa agcattttgt attaaagaat
3361 ttaattctga tctcaaaaaa aaaaaaaaaa aa
```

In embodiments, a VEGF gene used in any composition and method described herein is a VEGF-A isoform VEGF165 having the following nucleic acid sequence:

(SEQ ID NO: 9)

```
  1 atgaactttc tgctgtcttg ggtgcattgg agccttgcct tgctgctcta cctccaccat
 61 gccaagtggt cccaggctgc acccatggca gaaggaggag ggcagaatca tcacgaagtg
121 gtgaagttca tggatgtcta tcagcgcagc tactgccatc caatcgagac cctggtggac
181 atcttccagg agtaccctga tgagatcgag tacatcttca agccatcctg tgtgcccctg
```

-continued

```
241 atgcgatgcg ggggctgctg caatgacgag ggcctggagt gtgtgcccac tgaggagtcc

301 aacatcacca tgcagattat gcggatcaaa cctcaccaag gccagcacat aggagagatg

361 agcttcctac agcacaacaa atgtgaatgc agaccaaaga aagatagagc aagacaagaa

421 aatccctgtg ggccttgctc agagcggaga aagcatttgt ttgtacaaga tccgcagacg

481 tgtaaatgtt cctgcaaaaa cacagactcg cgttgcaagg cgaggcagct tgagttaaac

541 gaacgtactt gcagatgtga caagccgagg cggtga
```

In embodiments, a VEGF gene or a fragment thereof used in the method described herein has at least 80%, 85%, 90%, 95%, 96%, 97%, 98%, 99% or 100% nucleic acid sequence identity across the whole sequence or a portion of the sequence (e.g. a 50, 100, 150 or 200 continuous nucleic acid portion) compared to a naturally occurring VEGF gene. In embodiments, VEGF gene used herein is substantially identical (e.g., 80%, 85%, 90%, 95%, 96%, 97%, 98%, 99% or 100% identical) to any one of nucleic acid sequences of SEQ ID Nos: 1-9. In embodiments, VEGF gene used herein is a fragment (e.g., 1-100, 1-150, 1-200, 1-250, 1-300, 1-350, 1-400, 1-450, 1-500, 1-550, 1-600, 1-650, 1-700 nucleotides in length) of any one of nucleic acid sequences of SEQ ID Nos: 1-9. In embodiments, VEGF gene used herein is a fragment (e.g., 1-100, 1-150, 1-200, 1-250, 1-300, 1-350, 1-400, 1-450, 1-500, 1-550, 1-600, 1-650, 1-700) of a variant (e.g., 80%, 85%, 90%, 95%, 96%, 97%, 98%, 99% or 100% identical to a naturally occurring VEGF gene) of any one of nucleic acid sequences of SEQ ID Nos: 1-9.

In embodiments, VEGF gene used herein is substantially identical (e.g., 80%, 85%, 90%, 95%, 96%, 97%, 98%, 99% or 100% identical) to nucleic acid sequence of SEQ ID No: 9. In embodiments, VEGF gene used herein is a fragment (e.g., 1-100, 1-150, 1-200, 1-250, 1-300, 1-350, 1-400, 1-450, 1-500) of nucleic acid sequence of SEQ ID No: 9. In embodiments, VEGF gene used herein is a fragment (e.g., 1-100, 1-150, 1-200, 1-250, 1-300, 1-350, 1-400, 1-450, 1-500 nucleotides in length) of a variant (e.g., 80%, 85%, 90%, 95%, 96%, 97%, 98%, 99% or 100% identical to a naturally occurring VEGF gene) of nucleic acid sequence of SEQ ID No: 9.

In embodiments, the nucleic acid described herein forms part of a vector nucleic acid. Typically, the vector is a replication-incompetent viral vector. For example, the replication-incompetent viral vector is a replication-incompetent DNA viral vector (including, but is not limited to, adenoviruses, adeno-associated viruses). For example, the replication-incompetent viral vector is a replication-incompetent RNA viral vector (including, but is not limited to, replication defective retroviruses and lentiviruses). In embodiments, the vector is an adeno-associated viral type-2 (AAV2) vector.

In embodiments, the vector nucleic acid includes sequence includes:

```
                                                    (SEQ ID NO: 11)
CCTGCAGGCAGCTGCGCGCTCGCTCGCTCACTGAGGCCGCCCGGGCAAAGCCCGGGCGTC

GGGCGACCTTTGGTCGCCCGGCCTCAGTGAGCGAGCGAGCGCGCAGAGAGGGAGTGGCCA

ACTCCATCACTAGGGGTTCCTGCGGCCGCACGCGTGGAGCTAGTTATTAATAGTAATCAA

TTACGGGGTCATTAGTTCATAGCCCATATATGGAGTTCCGCGTTACATAACTTACGGTAA

ATGGCCCGCCTGGCTGACCGCCCAACGACCCCCGCCCATTGACGTCAATAATGACGTATG

TTCCCATAGTAACGTCAATAGGGACTTTCCATTGACGTCAATGGGTGGAGTATTTACGGT

AAACTGCCCACTTGGCAGTACATCAAGTGTATCATATGCCAAGTACGCCCCCTATTGACG

TCAATGACGGTAAATGGCCCGCCTGGCATTATGCCCAGTACATGACCTTATGGGACTTTC

CTACTTGGCAGTACATCTACGTATTAGTCATCGCTATTACCATGGTGATGCGGTTTTGGC

AGTACATCAATGGGCGTGGATAGCGGTTTGACTCACGGGGATTTCCAAGTCTCCACCCCA

TTGACGTCAATGGGAGTTTGTTTTGCACCAAAATCAACGGGACTTTCCAAAATGTCGTAA

CAACTCCGCCCCATTGACGCAAATGGGCGGTAGGCGTGTACGGTGGGAGGTCTATATAAG

CAGAGCTCGTTTAGTGAACCGTCAGATCGCCTGGAGACGCCATCCACGCTGTTTTGACCT

CCATAGAAGACACCGGGACCGATCCAGCCTCCGCGGATTCGAATCCCGGCCGGGAACGGT

GCATTGGAACGCGGATTCCCCGTGCCAAGAGTGACGTAAGTACCGCCTATAGAGTCTATA

GGCCCACAAAAAATGCTTTCTTCTTTTAATATACTTTTTTGTTTATCTTATTTCTAATAC

TTTCCCTAATCTCTTTCTTTCAGGGCAATAATGATACAATGTATCATGCCTCTTTGCACC

ATTCTAAAGAATAACAGTGATAATTTCTGGGTTAAGGCAATAGCAATATTTCTGCATATA
```

-continued

AATATTTCTGCATATAAATTGTAACTGATGTAAGAGGTTTCATATTGCTAATAGCAGCTA

CAATCCAGCTACCATTCTGCTTTTATTTTATGGTTGGGATAAGGCTGGATTATTCTGAGT

CCAAGCTAGGCCCTTTTGCTAATCATGTTCATACCTCTTATCTTCCTCCCACAGCTCCTG

GGCAACGTGCTGGTCTGTGTGCTGGCCCATCACTTTGGCAAAGAATTGGGATTCG

AACAT

CGATTGAATTCCCCGGGG ATCCTCTAGAGTCGACCTGCAGA

AAAA GCTGCGGAAT TGTACC C GCGGCCGCCGAAACC ATGAACTTTC TGCTGTCTTG GGTGCATTGG

AGCCTTGCCT TGCTGCTCTA CCTCCACCAT GCCAAGTGGT CCCAGGCTGC ACCCATGGCA

GAAGGAGGAG GGCAGAATCA TCACGAAGTG GTGAAGTTCA TGGATGTCTA TCAGCGCAGC

TACTGCCATC CAATCGAGAC CCTGGTGGAC ATCTTCCAGG AGTACCCTGA TGAGATCGAG

TACATCTTCA AGCCATCCTG TGTGCCCCTG ATGCGATGCG GGGGCTGCTG CAATGACGAG

GGCCTGGAGT GTGTGCCCAC TGAGGAGTCC AACATCACCA TGCAGATTAT GCGGATCAAA

CCTCACCAAG GCCAGCACAT AGGAGAGATG AGCTTCCTAC AGCACAACAA ATGTGAATGC

AGACCAAAGA AAGATAGAGC AAGACAAGAA AATCCCTGTG GGCCTTGCTC AGAGCGGAGA

AAGCATTTGT TTGTACAAGA TCCGCAGACG TGTAAATGTT CCTGCAAAAA CACAGACTCG

CGTTGCAAGG CGAGGCAGCT TGAGTTAAAC GAACGTACTT GCAGATGTGA CAAGCCGAGG

CGGTGA CCGGGCAGGAGGAA GCGGCCGCG GGGATCCAGA CATGATAAGA TACA TTGATG

AGTTTGGACA AACCAC AGCT T GCCTCGAGCAGCGC TGCT

CGAGAGATCTACGGGTGGCATCCCTGTGACCCCTCCCCAGTGCCTCTCCTGGCCCT

GGAAGTTGCCACTCCAGTGCCCACCAGCCTTGTCCTAATAAAATTAAGTTGCATCATTTT

GTCTGACTAGGTGTCCTTCTATAATATTATGGGGTGGAGGGGGGTGGTATGGAGCAAGGG

GCAAGTTGGGAAGACAACCTGTAGGGCCTGCGGGGTCTATTGGGAACCAAGCTGGAGTGC

AGTGGCACAATCTTGGCTCACTGCAATCTCCGCCTCCTGGGTTCAAGCGATTCTCCTGCC

TCAGCCTCCCGAGTTGTTGGGATTCCAGGCATGCATGACCAGGCTCAGCTAATTTTTGTT

TTTTTGGTAGAGACGGGGTTTCACCATATTGGCCAGGCTGGTCTCCAACTCCTAATCTCA

GGTGATCTACCCACCTTGGCCTCCCAAATTGCTGGGATTACAGGCGTGAACCACTGCTCC

CTTCCCTGTCCTTCTGATTTTGTAGGTAACCACGTGCGGACCGAGCGGCCGCAGGAACCC

CTAGTGATGGAGTTGGCCACTCCCTCTCTGCGCGCTCGCTCGCTCACTGAGGCCGGGCGA

CCAAAGGTCGCCCGACGCCCGGGCTTTGCCCGGGCGGCCTCAGTGAGCGAGCGAGCGCGC

AGCTGCCTGCAGGGGCGCCTGATGCGGTATTTTCTCCTTACGCATCTGTGCGGTATTTCA

CACCGCATACGTCAAAGCAACCATAGTACGCGCCCTGTAGCGGCGCATTAAGCGCGGCGG

GTGTGGTGGTTACGCGCAGCGTGACCGCTACACTTGCCAGCGCCCTAGCGCCCGCTCCTT

TCGCTTTCTTCCCTTCCTTTCTCGCCACGTTCGCCGGCTTTCCCCGTCAAGCTCTAAATC

GGGGGCTCCCTTTAGGGTTCCGATTTAGTGCTTTACGGCACCTCGACCCCAAAAAACTTG

ATTTGGGTGATGGTTCACGTAGTGGGCCATCGCCCTGATAGACGGTTTTTCGCCCTTTGA

CGTTGGAGTCCACGTTCTTTAATAGTGGACTCTTGTTCCAAACTGGAACAACACTCAACC

CTATCTCGGGCTATTCTTTTGATTTATAAGGGATTTTGCCGATTTCGGCCTATTGGTTAA

AAAATGAGCTGATTTAACAAAAATTTAACGCGAATTTTAACAAAATATTAACGTTTACAA

TTTTATGGTGCACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCATCCGCTTACA

GACAAGCTGTGACCGTCTCCGGGAGCTGCATGTGTCAGAGGTTTTCACCGTCATCACCGA

-continued

AACGCGCGAGACGAAAGGGCCTCGTGATAC GCCTATTTTTATAGGTTAATGT

GCCC GTGTC TCAAAATCTC TGAT GTTACA TTGCACAAGA TAAAAATATA

TCATCATGAA CAATAAAA CT GTCTGCTTAC ATAAACAGTA ATACAAGGGG

TGTTATGAGC CATATTCAAC GGGAAACGTC GAGGCCGCGA TTAAATTCCA

ACATGGATGC TGATTTATAT GGGTATAAAT GGGCTCGCGA TAATGTCGGG

CAATCAGGTG CGACAATCTA TCGCTTGTAT GGGAAGCCCG ATGCGCCAGA

GTTGTTTCTG AAACATGGCA AAGGTAGCGT TGCCAATGAT GTTACAGATG

AGATGGTCAG ACTAAACTGG CTGACGGAAT TTATGCCTCT TCCGACCATC

AAGCATTTTA TCCGTACTCC TGATGATGCA TGGTTACTCA CCACTGCGAT

CCCCGGAAAA ACAGCATTCC AGGTATTAGA AGAATATCCT GATTCAGGTG

AAAATATTGT TGATGCGCTG GCAGTGTCCC TGCGCCGGTT GCATTCGATT

CCTGTTTGTA ATTGTCCTTT TAACAGCGAT CGCGTATTTC GTCTCGCTCA

GGCGCAATCA CGAATGAATA ACGGTTTGGT TGATGCGAGT GATTTTGATG

ACGAGCGTAA TGGCTGGCCT GTTGAACAAG TCTGGAAAGA AATGCATAAA

CTTTTGCCAT TCTCACCGGA TTCAGTCGTC ACTCATGGTG ATTTCTCACT

TGATAACCTT ATTTTTGACG AGGGGAAATT AATAGGTTGT ATTGATGTTG

GACGAGTCGG AATCGCAGAC CGATACCAGG ATCTTGCCAT CCTATGGAAC

TGCCTCGGTG AGTTTTCTCC TTCATTACAG AAACGGCTTT TTCAAAAATA

TGGTATTGAT AATCCTGATA TGAATAAATT GCAGTTTCAT TTGATGCTCG

ATGAGTTTTT CTAATCAGAA TTGGTTAATT GGTTGTAACA TTATTCAGAT

TG GGCCCC GT TCCACTGAGC GTCAGAC ACCAAAATCCCTTAACGTG AGTTTTCGTTCC

ACTGAGCGTCAGACCCCGTAGAAAAGATCAAAGGATCTTCTTGAGATCCTTTTTTTCTGC

GCGTAATCTGCTGCTTGCAAACAAAAAAACCACCGCTACCAGCGGTGGTTTGTTTGCCGG

ATCAAGAGCTACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCTGTAGCACCGC

CTACATACCTCGCTCTGCTAATCCTGTTACCAGTGGCTGCTGCCAGTGGCGATAAGTCGT

GTCTTACCGGGTTGGACTCAAGACGATAGTTACCGGATAAGGCGCAGCGGTCGGGCTGAA

CGGGGGGTTCGTGCACACAGCCCAGCTTGGAGCGAACGACCTACACCGAACTGAGATACC

TACAGCGTGAGCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGGGGAAACGCCT

GGTATCTTTATAGTCCTGTCGGGTTTCGCCACCTCTGACTTGAGCGTCGATTTTTGTGAT

GCTCGTCAGGGGGGCGGAGCCTATGGAAAAACGCCAGCAACGCGGCCTTTTTACGGTTCC

TGGCCTTTTGCTGGCCTTTTGCTCACATGT
[Underlined indicates the VEGF gene and Bold/underlined incidates the KanR insert]

Further provided are pharmaceutical compositions/formulations that include a composition disclosed herein in combination with at least one pharmaceutically acceptable excipient or carrier.

Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids such as glycine, carbohydrates, chelating agents, sugars, and other standard ingredients known to those skilled in the art (Remington's Pharmaceutical Science 16$^{th}$ edition, Osol, A. Ed. 1980).

A pharmaceutical formulation including a composition as described herein can be administered by a variety of methods known in the art. The route and/or mode of administration may vary depending upon the desired results. In embodiments, administration is intravenous, intramuscular, intraperitoneal, or subcutaneous, or administered proximal to the site of the target. Pharmaceutically acceptable excipients can be suitable for intravenous, intramuscular, subcutaneous, parenteral, spinal or epidermal administration (e.g., by injection or infusion).

Pharmaceutical formulations of the nucleic acid as described herein can be prepared in accordance with methods well known and routinely practiced in the art. See, e.g., *Remington: The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions.

Actual dosage levels of the active ingredients (i.e., the compositions described herein) in the pharmaceutical compositions described herein can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions employed, the route of administration, the time of administration, the rate of excretion of the particular composition (e.g., the nucleic acid described herein) being employed, the duration of the treatment, other drugs, compounds and/or materials used in combination with the particular compositions employed, the age, sex, weight, condition, general health and prior medical history of the patient being treated, and like factors.

A physician or veterinarian can start doses of the nucleic acid (e.g., VEGF gene optionally within a viral vector) of the invention employed in the pharmaceutical formulation at levels lower than that required to achieve the desired therapeutic effect and gradually increase the dosage until the desired effect is achieved. In general, effective doses of the compositions described herein vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with a pharmaceutical formulation of the invention, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

The compositions provided herein can be administered on multiple occasions. Intervals between single dosages can be weekly, monthly or yearly. Intervals can also be irregular as indicated by measuring immune response to the neo-antigen. Alternatively, composition can be administered as a sustained release formulation, in which case less frequent administration is required. Dosage and frequency vary depending on the half-life of the composition in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The invention provides a method for treating an injury of a fibrous connective tissue in a subject in need thereof. In embodiments, the method includes administering to the subject a therapeutically effective amount of any composition described herein or a polynucleotide comprising vascular endothelial growth factor (VEGF) gene or a fragment thereof.

The terms effective amount and effective dosage are used interchangeably. The term effective amount is defined as any amount necessary to produce a desired physiologic response. In this case, for example, a desired physiologic response includes a subject being more (e.g., about 5%, 10%, 15%, 20%, 25%, 30%, 35%, 40%, 45%, 50%, 75%, 100% or more) responsive when administered with a VEGF gene or fragment thereof compared to the response level of the subject without taking the VEGF gene therapy described herein. The amount used in the method reduces one or more symptoms of the conditions to be treated. Exemplary symptoms of tendinopathy include, but are not limited to, pain, stiffness, loss of strength of affected area, tender, red, warm or swollen in the affected area. In embodiments, the amount used in the method increases tendon healing for at least 10%, 15%, 20%, 25%, 30%, 35%, 40%, 45%, 50%, 75%, 100% or more compared to other therapies or compared to the level of tendon healing without any treatment. In embodiments, the amount used in the method increases tendon strength for at least about 10%, 15%, 20%, 25%, 30%, 35%, 40%, 45%, 50%, 75%, 100%, 150%, 200%, 250% or more compared to other therapies or compared to the level of tendon strength without any treatment.

According to the methods provided herein, an injury of a fibrous connective tissue is a tendon injury. In embodiments, the tendon injury is tendinopathy. In embodiments, the tendon injury is paratenonitis, which refers to inflammation of the paratenon, or paratendinous sheet located between the tendon and its sheath. In embodiments, the tendon injury is tendinosis, in which combinations of paratenon inflammation and tendon degeneration are both present. In embodiments, the tendon injury is tendinitis, which refers to degeneration with inflammation of the tendon as well as vascular disruption. In embodiments, the tendon injury is tendon disunion.

EXAMPLES

Example 1—bFGF or VEGF Gene Therapy Corrects Insufficiency in the Intrinsic Healing Capacity of Tendons Tendon injury during limb motion is common. Damaged tendons heal poorly and frequently undergo unpredictable ruptures or impaired motion due to insufficient innate healing capacity. By basic fibroblast growth factor (bFGF) or vascular endothelial growth factor (VEGF) gene therapy via adeno-associated viral type-2 (AAV2) vector to produce supernormal amount of bFGF or VEGF intrinsically in the tendon, we effectively corrected the insufficiency of the tendon healing capacity. This therapeutic approach resulted in substantial amelioration of the low growth factor activity with significant increases in bFGF or VEGF from weeks 4 to 6 in the treated tendons ($p<0.05$ or $p<0.01$), significantly promoted production of type I collagen and other extracellular molecules ($p<0.01$) and accelerated cellular proliferation, and (3) significantly increased tendon strength by 68-91% from week 2 after AAV2-bFGF treatment and by 82-210% from week 3 after AAV2-VEGF compared with that of the controls ($p<0.05$ or $p<0.01$). Moreover, the transgene expression dissipated after healing was complete. These findings show that the gene therapy provides an optimistic solution to the insufficiencies of the intrinsic healing capacity of the tendon and offers an effective therapeutic possibility for patients with tendon disunion.

Tendon injuries constitute one of the most common disorders of the human body, affecting 1 in 2,000 people each year, with the tendon injuries to the hand and wrist occurring in 1 in 2,700 people each year. These tendon injuries can result from trauma, overuse, or age-related degeneration from work, daily life, and sports activities. Injuries to tendons, tendon-bone-junctions, and related tissues (such as ligaments) can occur in numerous areas of the body. People with such injuries constitute a large proportion of the patients treated in emergency rooms, inpatient surgical departments, outpatient clinics, and rehabilitation facilities. Damaged tendons heal poorly; their surgical repair frequently ends in unpredictable rupture or impaired extremity motion due to insufficient healing capacity. The treatment of damaged tendons remains a challenge in medicine because of the insufficiency of the healing capacity of the tendon itself and lack of method to increase the biological healing strength.

Tendons, particularly those covered by an intrasynovial sheath, have very limited vascular supply, lack sufficient cellularity, and have low growth factor activity. These structural or biological features account for the weak healing strength of tendons after injury. So far, treatment options for injured tendons have not proven adequate to correct the insufficiency of intrinsic healing capacity of intrasynovial tendons, despite preliminary findings indicating better healing responses of extrasynovial tendons to some therapies in animal models. We aimed at developing a new therapeutic approach that corrects the fundamental problem underlying intrasynovial tendon healing with introduction of select growth factor genes to the tendon producing supernormal amounts of these factors required during the early tendon healing period.

We tested efficiency of the transfer of a number of growth factor genes in promoting tendon healing in vitro and in vivo and found vascular endothelial growth factor (VEGF) is among the most potent stimulators of tenocytes (tendon fibroblasts) proliferation and type I collagen production. An adeno-associated viral (AAV) vector was the gene delivery vehicle in our study because this virus is non-pathogenic. We hypothesized that transfer of VEGF genes using AAV type 2 (AAV2) vectors would augment productions of growth factors, collagens, and their modulators in the treated tendons, that eventually significantly enhance the healing strength over a critical period of the tendon healing. The study showed that the VEGF gene therapy corrects the insufficiency of the intrinsic healing capacity, leads to quicker and more robust tendon healing after surgery, and may become an efficient biological treatment modality for the patients with injured tendons.

Results

We completely severed chicken flexor tendons, i.e., floxor digitorum profundus (FDP) tendons and injected AAV2 vectors carrying transgenes (bFGF or VEGF genes) or sham AAV2 vectors immediately before repairing the tendon surgically. The vectors were introduced to the tendon through micro-injection to both tendon stumps through cross-sections of the tendon cut. We used non-injected tendons as non-treatment controls.

We injected a single dose of AAV2-bFGF or AAV2-VEGF ($2\times10^9$ viral particles/tendon) into transversely lacerated digital flexor tendons of chickens. The dose of injection was decided according to a pilot study using the same chicken tendon injury and repair model. In the pilot study, we injected $2\times10^7$, $2\times10^8$, $2\times10^9$, and $2\times10^{10}$ viral particles (vp) to each tendon and found an increase in healing strength by 30-40% when the amount of vectors increased from $2\times10^7$ to $2\times10^8$ vp or greater, but no statistical difference was found between tendons injected with $2\times10^8$, $2\times10^9$ or $2\times10^{10}$ vp (8 tendons at each dose, statistical power >0.80).

bFGF or VEGF gene delivery prevents the drop of bFGF or increases VEGF gene expression in healing tendons. We harvested tendons injected with AAV2-bFGF or AAV2-VEGF, or sham AAV2 vector, and the tendons in non-injection controls over a 16-week period at 8 time-points (weeks 1, 2, 3, 4, 6, 8, 12, and 16), covering the early, middle, and late tendon healing stages. Real-time polymerase chain reactions (qPCR) and western blot were performed to analyze expression of transferred bFGF or VEGF genes, respectively.

The bFGF gene delivered to the chickens was of rat origin, while the VEGF was of human origin. By designing primers that specifically amplify rat bFGF segments using qPCR, we were able to assess the changes in the expression levels of the exogenous bFGF gene from post-surgical weeks 1 to 16 (FIG. 1A). The expression of bFGF transgene was detected at week 1, and gradually increased from weeks 2 to 8, then dropped from weeks 8 to 12. The bFGF transgene expression was statistically greater at weeks 4, 6, and 8 than that at 1, 2, and 12 ($p<0.05$ or $p<0.001$). Expression of the bFGF transgene became undetectable at week 16. At 1 to 4 weeks, the expression of the endogenous chicken bFGF was increased significantly in the tendon treated with AAV2-bFGF compared with that in those treated with sham vectors or in non-injection controls ($p<0.05$ or $p<0.01$). In the non-injection control tendons, the expression of the endogenous bFGF decreased significantly at weeks 1 to 5 after injury compared with healthy tendons ($p<0.05$ or $p<0.01$).

Figure 1B:
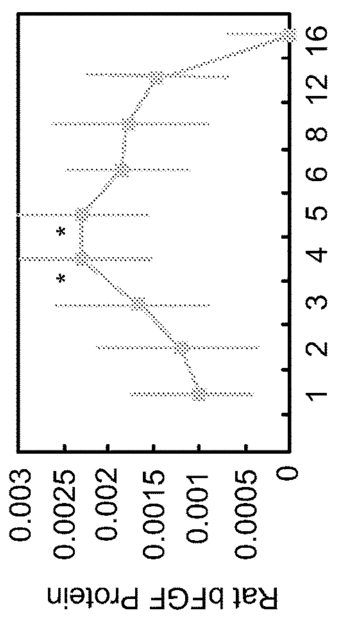
FIG. 1B is a line graph showing bFGF protein levels. *indicates the data significantly greater than that at weeks 1, 2, 12, 16 ($p<0.01$ or $p<0.01$).
Figure 1C:
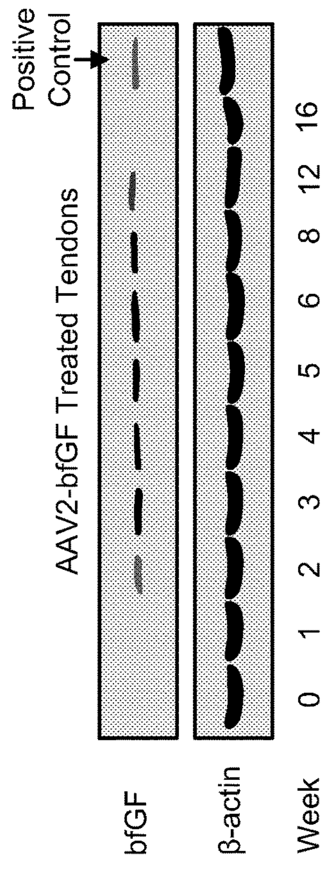
FIG. 1C is a representative picture of western blot using mouse-anti-rat bFGF antibody. Rat bFGF was increased from weeks 2 to 4, peaked at weeks 4 and 5, and declined at weeks 6 to 12. The bFGF was not detectable at week 16.
Figure 1D:
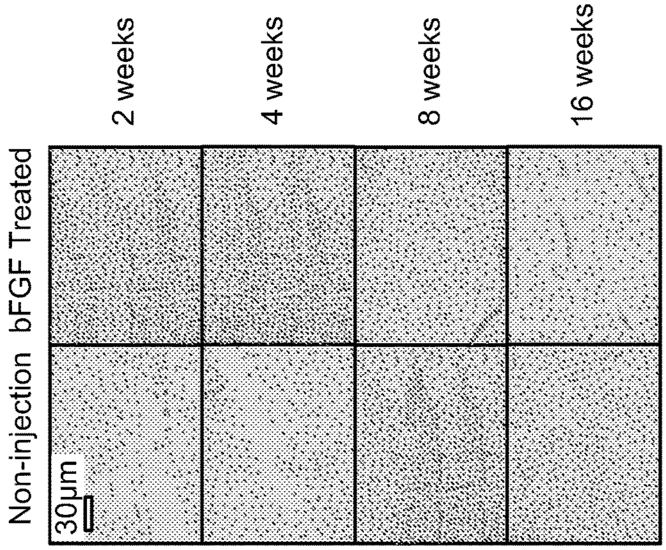
FIG. 1D is a series of pictures of immunohistochemistry analyses showing the changes of the bFGF (chicken and rat origins) in the AAV2-bFGF injected and non-injection control tendons up to week 16. The bFGF was increased at weeks 2 and 4 in the AAV2-bFGF injected tendon.

Western blot analysis using mouse-anti-rat bFGF antibody showed similar increases in the transgene in weeks 2 and 3, a peak from weeks 4 to 8, and no detectable exogenous bFGF at week 16 (FIGS. 1*b,c*). Immunohistochemical staining verified an increase in the total amount of bFGF of the AAV2-bFGF treated tendons (FIG. 1D).

Figure 1F:
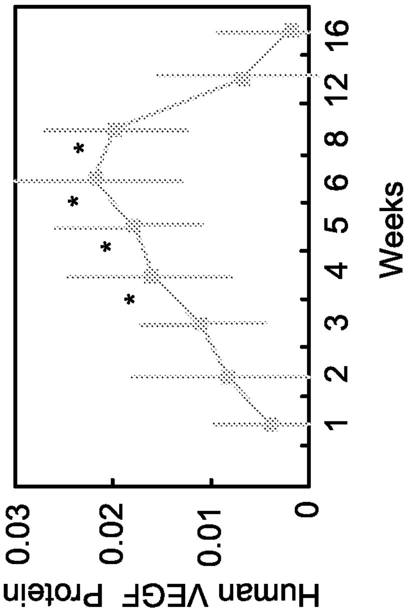
FIG. 1F is a line graph of Western blot analysis showing gradual increase in the expression of human VEGF from weeks 1 to 6. The VEGF peaked at week 6 and dropped thereafter. *indicates the data significantly greater than that at week 1, 12, or 16 ($p<0.01$ or $p<0.001$).
Figure 1E:
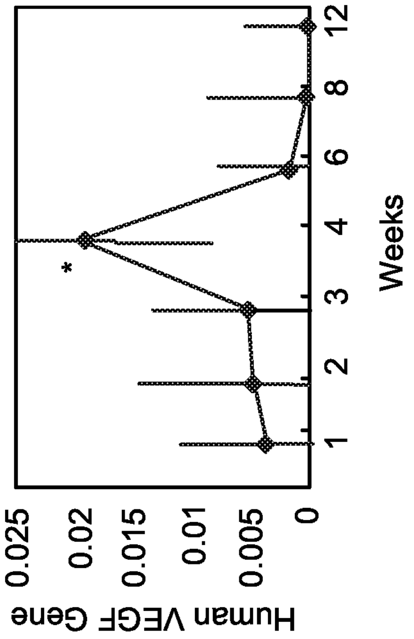
FIG. 1E is a line graph showing Transgene (human VEGF) expression in the AAV2-VEGF injected tendon. Transgene expression peaked at week 4. The expression was minimal at week 6, 8, and 12. *indicates the data significantly greater than that at other time-points ($p<0.05$ or $p<0.001$).

Similarly, VEGF transgene of human origin was detectable at weeks 1 through 8 and peaked at week 4, and the VEGF transgene expression was statistically the greatest at week 4 ($p<0.05$)(FIG. 1E). At weeks 2, 3, and 4, the expression of the endogenous VEGF in the tendon treated with AAV2-VEGF was increased significantly compared with that in the tendons injected with sham vectors or in non-injection controls ($p<0.01$). From weeks 2 to 12, the human VEGF was detected in the tendon by western blot using mouse-anti-human antibody, with peak in weeks 4 to 8 (FIGS. 1F,G). Production of the exogenous VEGF was not detectable at week 16 (FIG. 11G).

Figure 2A:
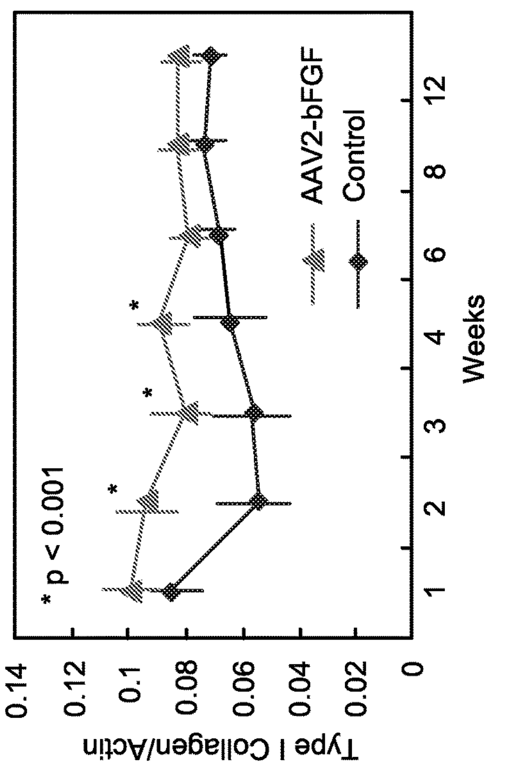
FIG. 2A is a line graph showing changes in expression of Type I collagen after AAV2-bFGF injection to the tendons. Type I collagen were significantly increased at weeks 2, 3, and 4 in the AAV2-bFGF injected tendon compared with the non-injection controls ($p<0.001$).
Figure 2B:
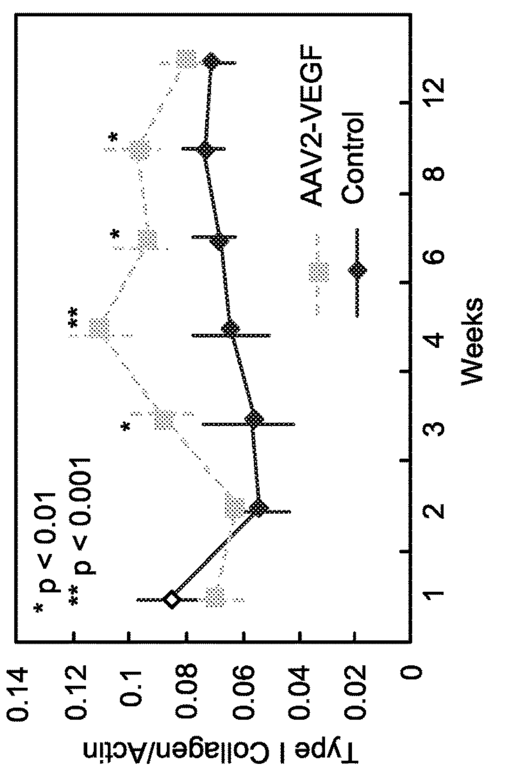
FIG. 2B is a line graph showing Type I collagen was significantly increased at weeks 4, 6, and 8 in the AAV2-VEGF injected tendon ($p<0.01$, or $p<0.001$).
Figure 2C:
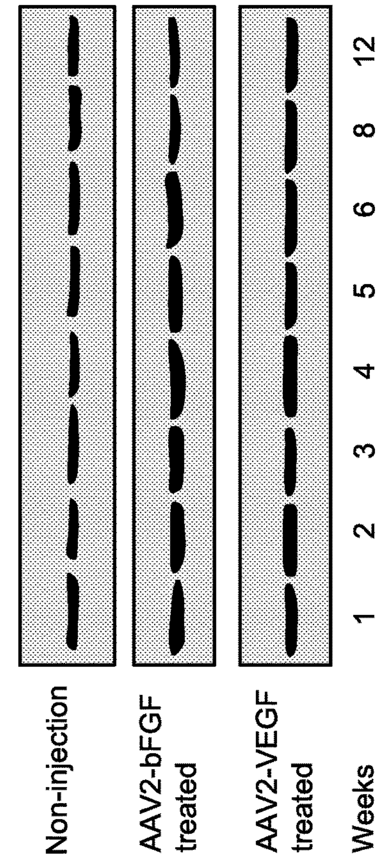
FIG. 2C is a photograph of gel pictures showing the changes in protein levels of type I collagen. Note an earlier increase (weeks 2 to 5) of the collagen I after AAV2-bFGF injection, but a greater and more persistent increase (up to week 8) after AAV2-VEGF injection.
Figure 2D:
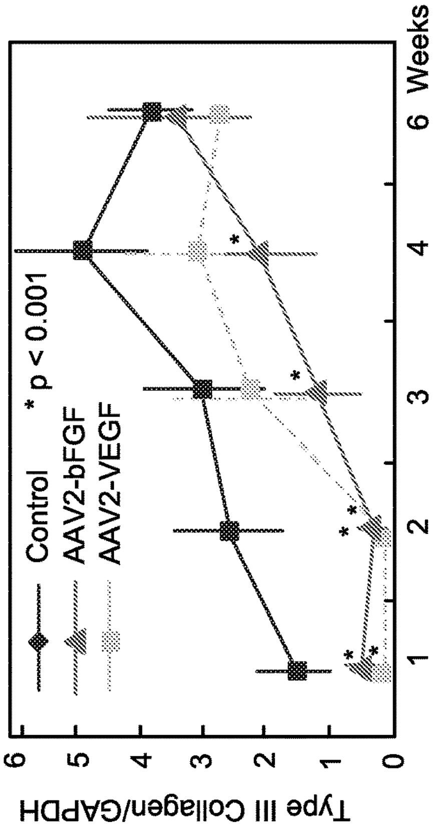
FIG. 2D is a line graph showing changes in type III collagen gene expression of the AAV2-bFGF and AAV2-VEGF injected tendons compared with non-injection controls ($p<0.001$, 1 to 4 weeks after AAV2-bFGF treatment, and 1 and 2 weeks after AAV2-VEGF treatment).

We used a set of primers to amplify a segment of the bFGF gene identical in chicken and rat bFGF genes. We found that levels of compound expression of both endogenous and the transferred bFGF genes increased in the early and middle healing periods (weeks 2 to 8) and the chicken bFGF gene was upregulated in this period in the AAV2-bFGF injected tendons. These increases were in contrast to the non-injection controls, which demonstrated down-regulation of their bFGF gene expression after injury, with the levels remaining low until week 8. From weeks 2 to 8, we also found significant increases in the expression of VEGF genes in the AAV2-VEGF injected tendon using primers amplifying a segment of gene common to both chicken and human VEGF genes.

bFGF and VEGF gene delivery produces an early increase in type I collagen production and modulates type III collagen production and other extracellular matrix gene expression. The main determinant of a successful tendon repair is the early gain of mechanical strength, which depends on robust synthesis of collagens and other extracellular matrix components to bridge the repair site. Type I collagen is particularly important for the gain of healing strength. Presence of the type III collagen early in repaired tendon is less favorable as it does not contribute much to the tensile strength of an intact or healing tendon. A primary goal of augmenting tendon strength should be to increase type I collagen and decrease type III collagen. Western blot analysis showed significant increases in expression of type I collagen in the AAV2-bFGF or AAV2-VEGF treated tendons (FIG. 2A-C), with significant increases at weeks 2, 3, and 4 in AAV2-bFGF treated tendons (FIG. 2A) and at weeks 3, 4, 6, and 8 in AAV2-VEGF treated tendons (FIG. 2B)($p<0.01$ or $p<0.001$). The amount of type I collagen was not increased significantly at week 1 or 12 after either therapy. After either therapy, type III collagen gene expression was dramatically down-regulated in the early weeks after surgery, i.e., week 1 and 2 ($p<0.05$ or $p<0.01$). In addition, down-regulation of type III collagen persisted at week 3 and 4 after AAV2-bFGF treatment (FIG. 2D). Expression of the type I and III collagen genes was very low in normal tendons, being 0.22 and 0.07 relative to the glyceraldehyde-3-phosphate dehydrogenase (GAPDH) gene, respectively. Both genes had significantly lower levels of expression in normal tendons than that in the surgically repaired tendons ($p<0.001$).

Figure 2E:
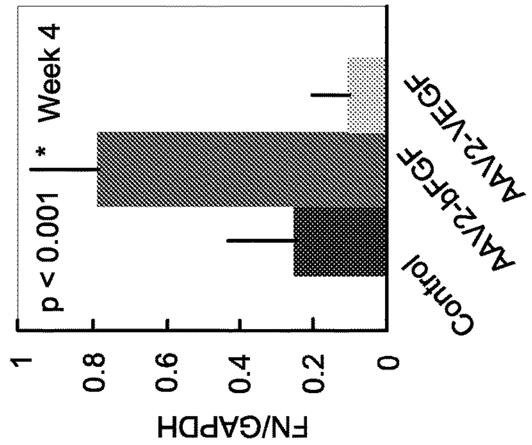
Figure 2F:
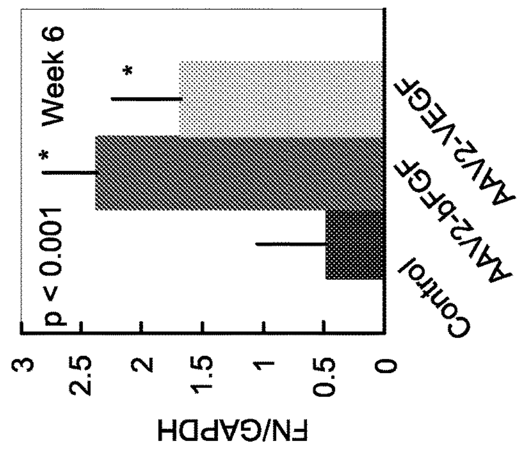
Figure 2G:
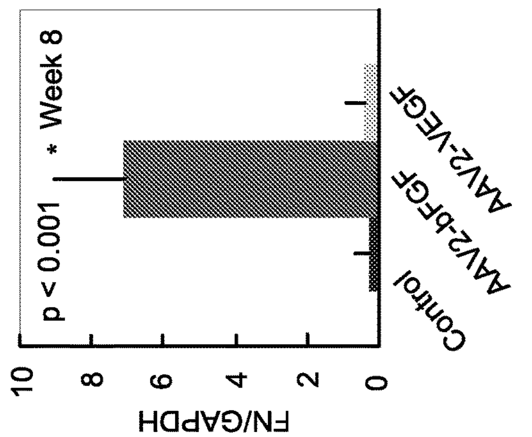
Figure 2H:
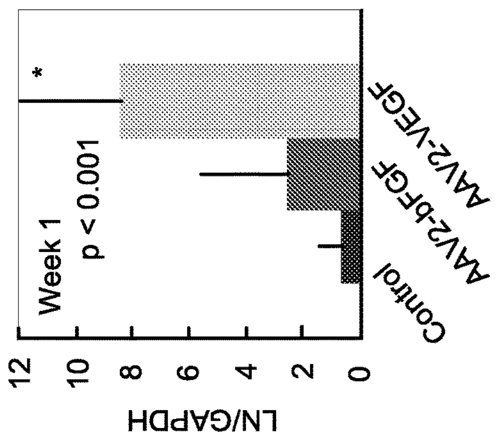
Figure 2I:
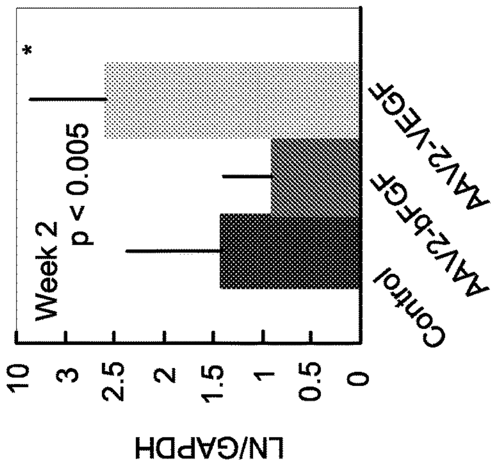

We used qPCR to examine expression of aggrecan (AGC), decorin (DCN), fibronectin (FN), laminin (LN), and fibromodulin (FMOD) genes at postoperative weeks 1, 2, 3, 4, 5, 6, and 8. We identified that increases in gene expression of FN at weeks 4, 6, and 8 after AAV2-bFGF treatment (FIG. 2E-G) and at week 6 after AAV2-VEGF treatment (FIG. 2F); similar increases were found of LN at weeks 1 and 2 after AAV2-VEGF treatment (FIG. 2H,I). Expression of AGC, DCN, and FMOD genes was not significantly changed by the gene therapy.

bFGF and VEGF gene delivery modulates metabolism of the tendon to favor healing. The metabolism of the extracellular matrix affects collagen production and degradation. Therefore, we determined gene expression and protein production of several principle regulators of metabolism. We assessed the expression of matrix metalloproteinases (MMPs) (MMP1, 2, 3, and 13) and tissue inhibitors of metalloproteinases (TIMPs) (TIMP2 and 3) using qPCR and western blot.

Figure 3B:
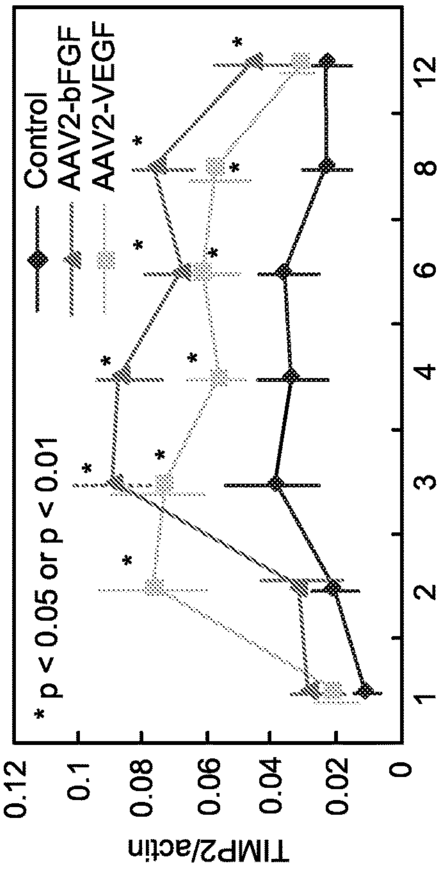
FIG. 3A and FIG. 3B are line graphs showing changes in regulators MMPs and TIMPs of metabolism in the AAV2-bFGF and AAV2-VEGF treated tendons. Significant changes in the expression of the MMP1 and TIMP2 were found in the tendons after either AAV2-bFGF or AAV2-VEGF treatment (n=6, in each group at each time point), typically from weeks 2 to 8 (*$p<0.05$ or $p<0.01$, compared with non-injection controls).
Figure 3A:
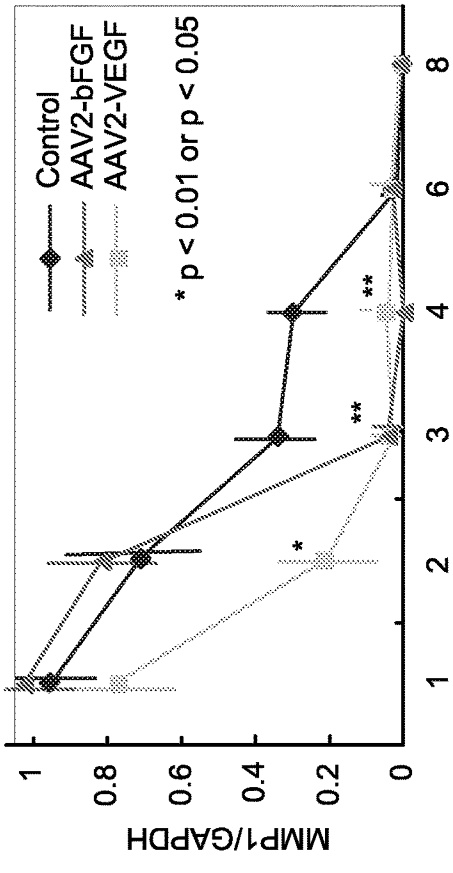
Figure 3C:
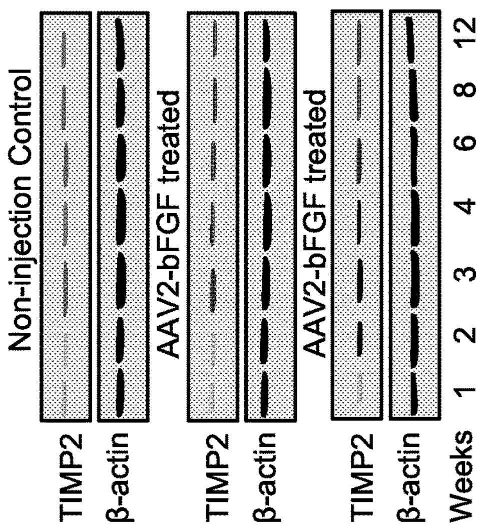
FIG. 3C is a photograph of western blot gel pictures showing that the TIMP2 was activated after the therapy from weeks 2 to 8 to inhibit collagen degradation.
Figure 3E:
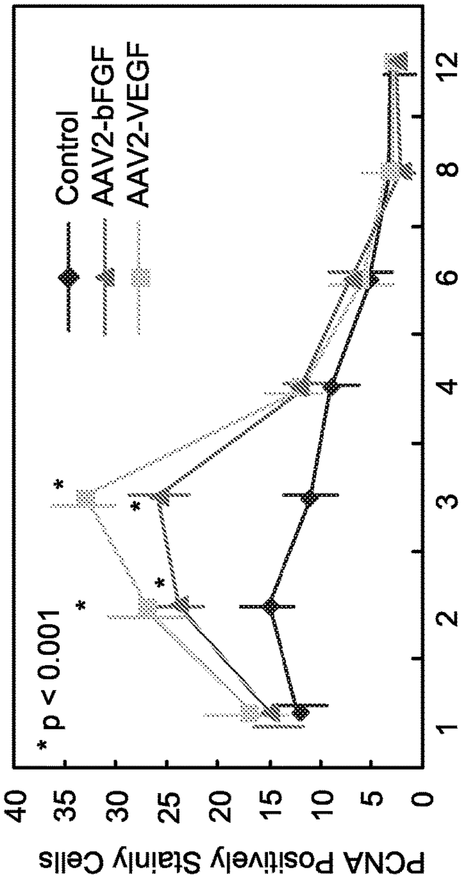
FIG. 3E is a line graph showing data from 6 fields of each of 6 tendon samples per group under 200× magnification. *indicates data of significant difference from the non-injection controls at weeks 2 and 3.
Figure 3D:
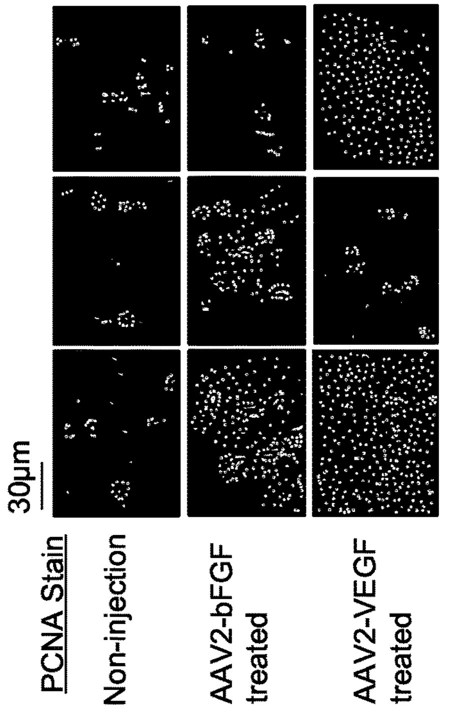
FIG. 3D is a photograph of PCNA staining showing significant increases in the positively-stained cells after injection of AAV2-bFGF or AAV2-VEGF at weeks 2 and 3 (200× magnification).
Figure 3F:
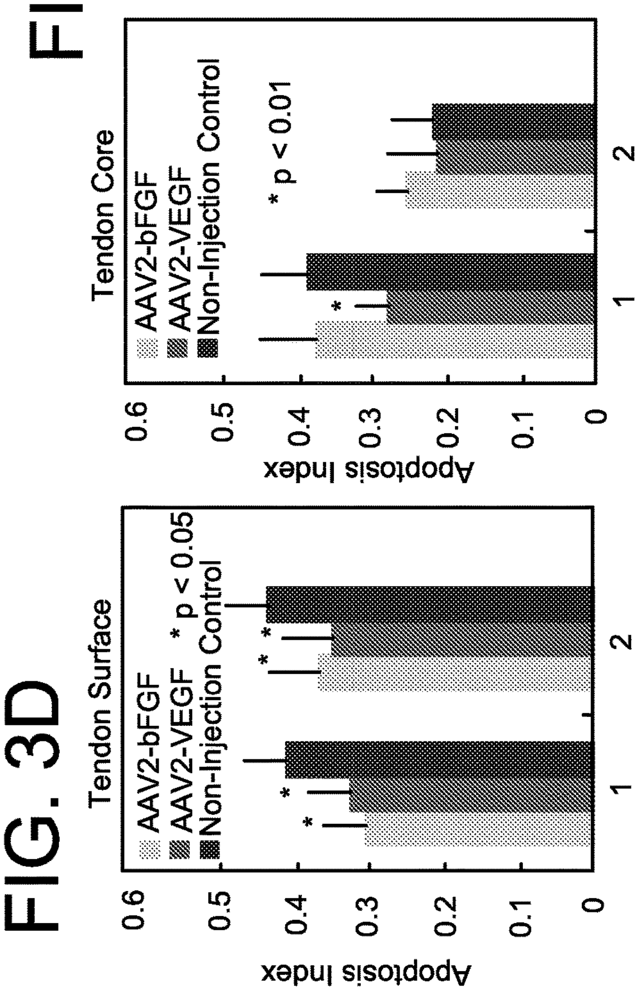
FIG. 3F is a bar graph showing apoptosis index, in tendon surface and core, of the AAV2-bFGF or AAV2-VEGF injected tendons and non-injection controls at weeks 1 and 2 (n=6, each group at each time point, *$p<0.05$ or $p<0.01$). No significant difference was found in the number of the PCNA positively stained cells and apoptosis index in these groups at weeks 4, 6, 8, and 12 (data not shown). *indicates the data of significant difference from the non-injection controls. The data of sham vector controls (not shown) were not significantly different from the non-injection controls. The bar in each group of the three bars, from left to right, represents AAV2-bFGF, AAV2-VEGF and non-injection control, respectively.
Figure 4:
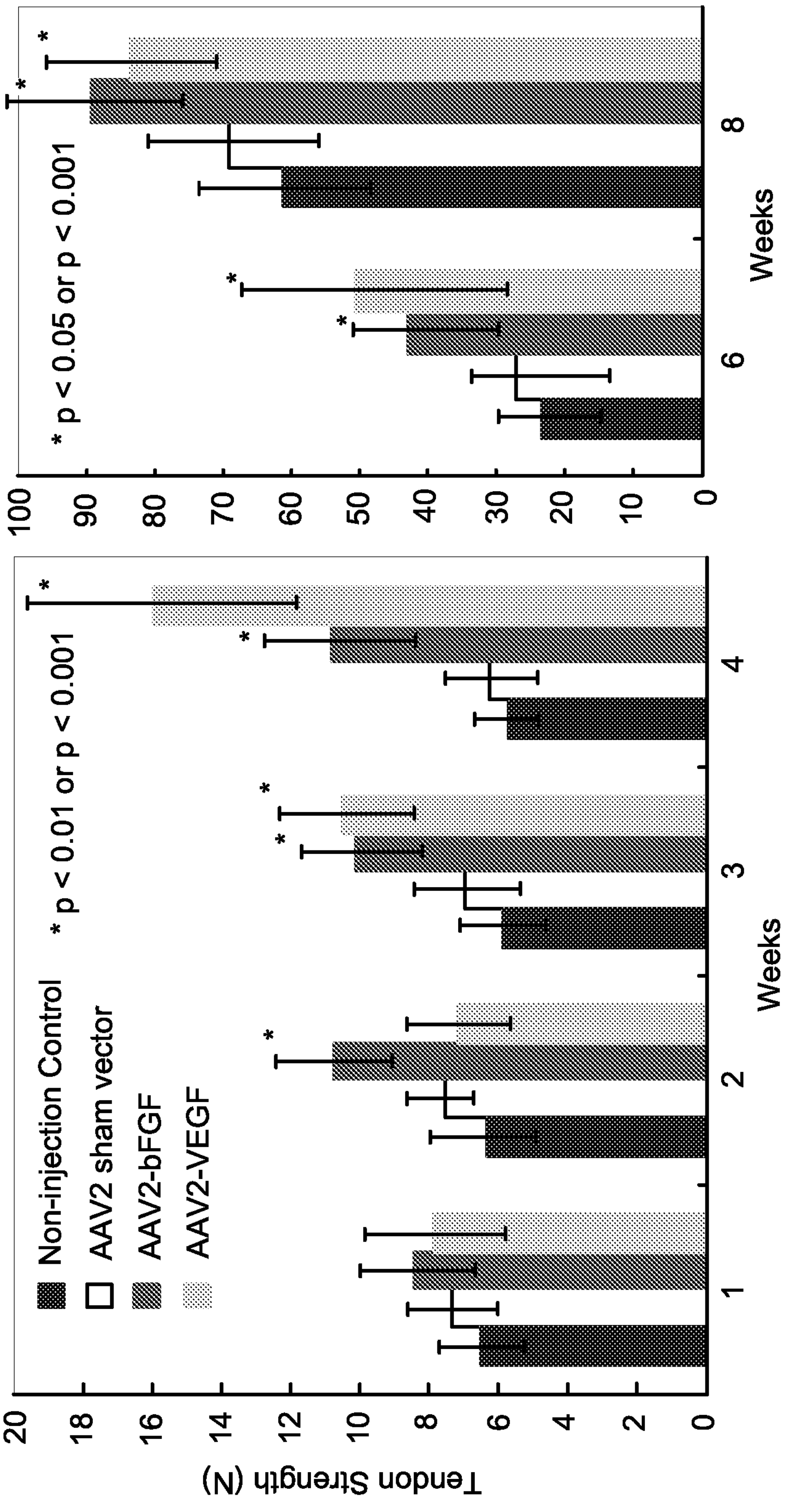

We found significant down-regulation of the MMP1 gene at weeks 3 and 4 in AAV2-bFGF treated tendons, and at weeks 2, 3, and 4 in the AAV2-VEGF treated tendons as compared with non-treated controls ($p<0.01$) (FIG. 3A). Expression of the MMP1 gene was $0.9\pm0.2$ (relative to GAPDH) in normal tendons, which was not significantly different from that in the injured tendon at weeks 1 and 2. We found significant down-regulation of the MMP3 gene at week 4 in AAV2-bFGF treated tendons ($p<0.01$), and from weeks 1 to 4 in AAV2-VEGF treated tendons ($p<0.05$ or $p<0.01$). In contrast, TIMP2 gene expression was up-regulated at weeks 3 to 12 after AAV2-bFGF treatment, and at weeks 2 to 8 after AAV2-VEGF treatment (FIG. 3B,C). Expression of the TIMP2 gene was $0.01\pm0.01$ (relative to GAPDH) in normal tendons, which was not significantly different from in the injured tendon at week 1. TIMP3 gene expression was up-regulated only transiently at weeks 1 and 2 after AAV2-bFGF treatment and at week 4 after AAV2-VEGF treatment.

bFGF or VEGF gene delivery increases proliferation and prohibits apoptosis of tendon fibroblasts. We quantified the proliferation of tenocytes using proliferating cellular nuclear antigen (PCNA) staining. PCNA positive cells were found to be increased significantly at weeks 2 and 3 after either AAV2-bFGF or AAV2-VEGF treatment (FIGS. 3D and 3E). We also examined apoptotic cells of the tendon surface and core regions. The apoptosis index (AI) dropped significantly at weeks 1 and 2 after AAV2-bFGF or AAV2-VEGF treatment on the tendon surface and at week 1 after AAV2-VEGF treatment in the core (FIG. 3F).

bFGF or VEGF gene delivery enhances the healing strength in the critical healing period. Using an Instron tensile testing machine (Model 4411, Instron Inc., Norwood, MA.), we measured the healing strength of the tendons injected with AAV2-bFGF or AAV2-VEGF at postoperative day 0, and at weeks 1, 2, 3, 4, 6, and 8. The healing strength is the most important mechanical parameter of actual effects of interventions on tendon healing. The gain in the strength is the ultimate goal of therapy. From weeks 1 to 4, the non-injection or sham vector control tendons typically exhibited "no-gain" in strength. By contrast, earlier increases in strength were recorded after either AAV2-bFGF or AAV2-VEGF treatment. Notably, healing strength after AAV2-bFGF was significantly increased at weeks 2, 3, 4, 6, and 8 compared with non-injection or sham vector injection controls (FIG. 4). After AAV2-VEGF injection, the strength of the tendons was significantly increased starting at week 3 and continually up to week 8. The increases in strength were dramatic—an increase by 68-91% in the AAV2-bFGF treated tendon, and an even greater increase in the AAV2-VEGF treated tendon—by 82-210%. In comparing the effectiveness of AAV2-bFGF with that of AAV2-VEGF, we found earlier significant effects after AAV2-bFGF treatment; however, the degree of increased strength of AAV2-VEGF injected tendons was greater than that of AAV2-bFGF injection at week 4 and 6 (FIG. 4). Injection of sham vectors did not significantly change strength compared to tendons in non-treatment controls ($p>0.05$, statistical power $>0.80$). At the end of week 8, the strengths of the tendons treated with either AAV2-bFGF or AAV2-VEGF were not statistically different from those of healthy tendons ($p>0.05$, statistical power $>0.80$). Twelve healthy FDP tendons of the chickens were tested; the ultimate strengths were $91\pm14$ N.

Figure 5A:
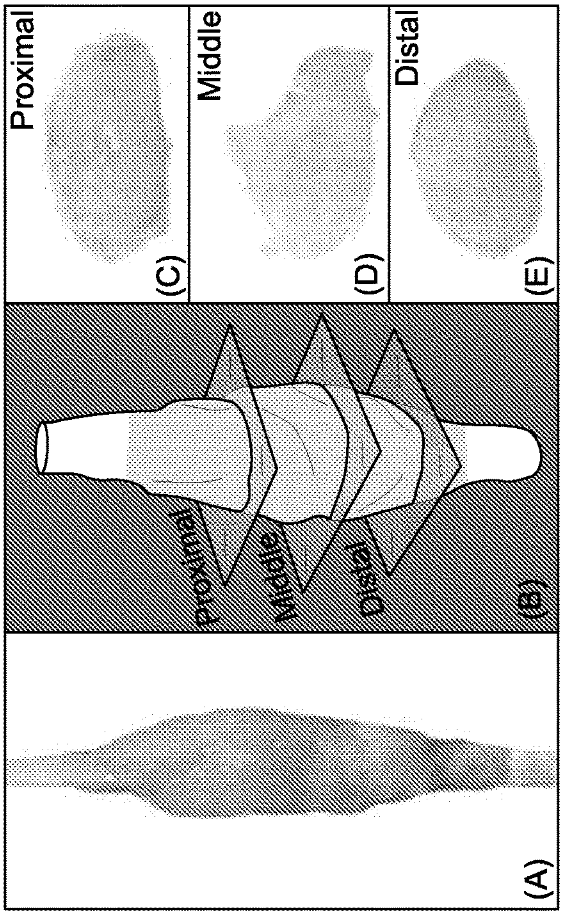
FIG. 5A is a photograph showing effects of AAV2-bFGF and AAV2-VEGF injection to the tendon on adhesion formation and amplitude of tendon movement. A three-dimensional analysis method for quantification of adhesions around the tendon was used. The tendon was sectioned through 3 cross-sectional levels (0.5 cm apart, with the middle section at the site of tendon repair) and was stained histologically. The area of adhesions and the ratio of adhesions to the healing tendons were computed to obtain adhesion scores.
Figure 5B:
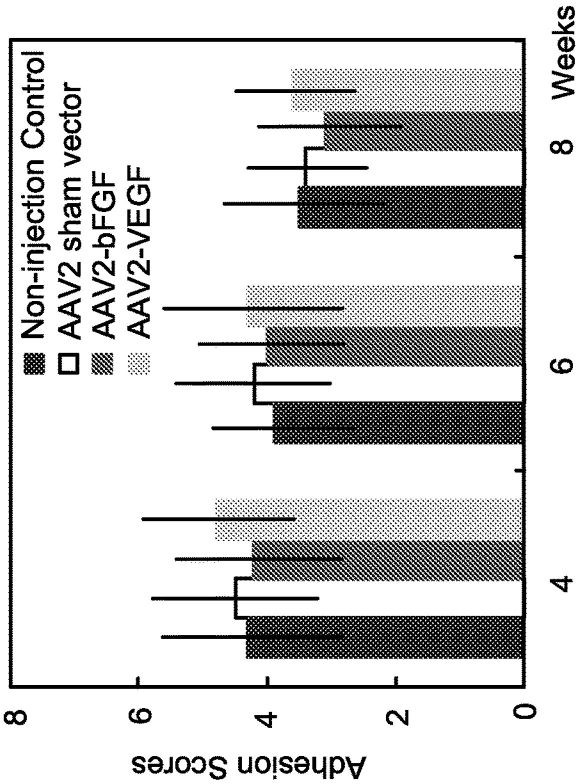
FIG. 5B is a bar graph showing adhesion scores (n=8, each group at each time point). No significant difference was found in the scores and area of adhesions (not shown). The bar in each group of the four bars, from left to right, represents non-injection control, AAV2 sham vector, AAV2-bFGF, and AAV2-VEGF respectively.
Figure 5D:
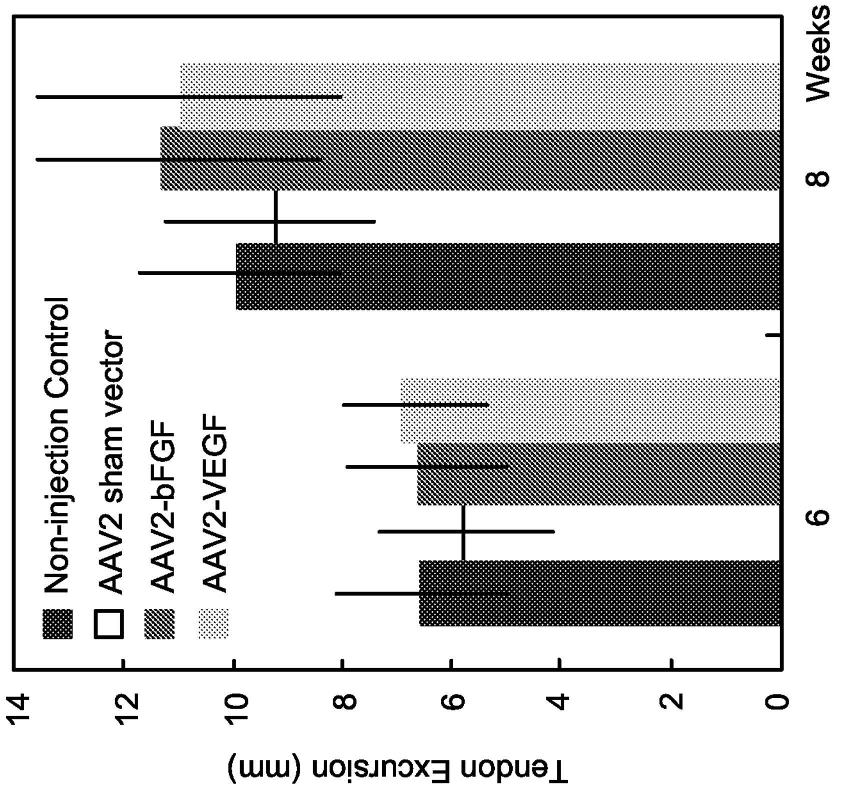
FIG. 5D is a bar graph showing tendon excursions under 10 N load to the repaired FDP tendon (n=12, each group at each time point). No significant differences were found in the work of flexion and tendon movement at week 6 and 8 ($p>0.05$, statistical power >0.85). The bar in each group of the four bars, from left to right, represents non-injection control, AAV2 sham vector, AAV2-bFGF, and AAV2-VEGF respectively.
Figure 5C:
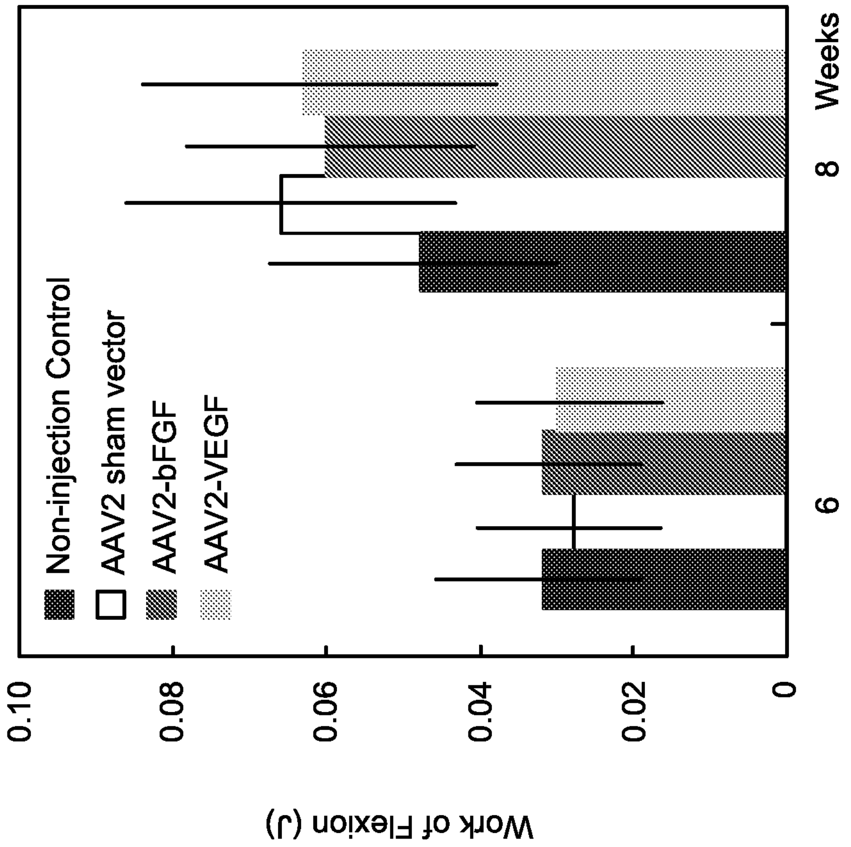
FIG. 5C is a bar graph showing work of flexion of the toes (n=12, each group at each time point). The bar in each group of the four bars, from left to right, represents non-injection control, AAV2 sham vector, AAV2-bFGF, and AAV2-VEGF respectively.
Figure 5F:
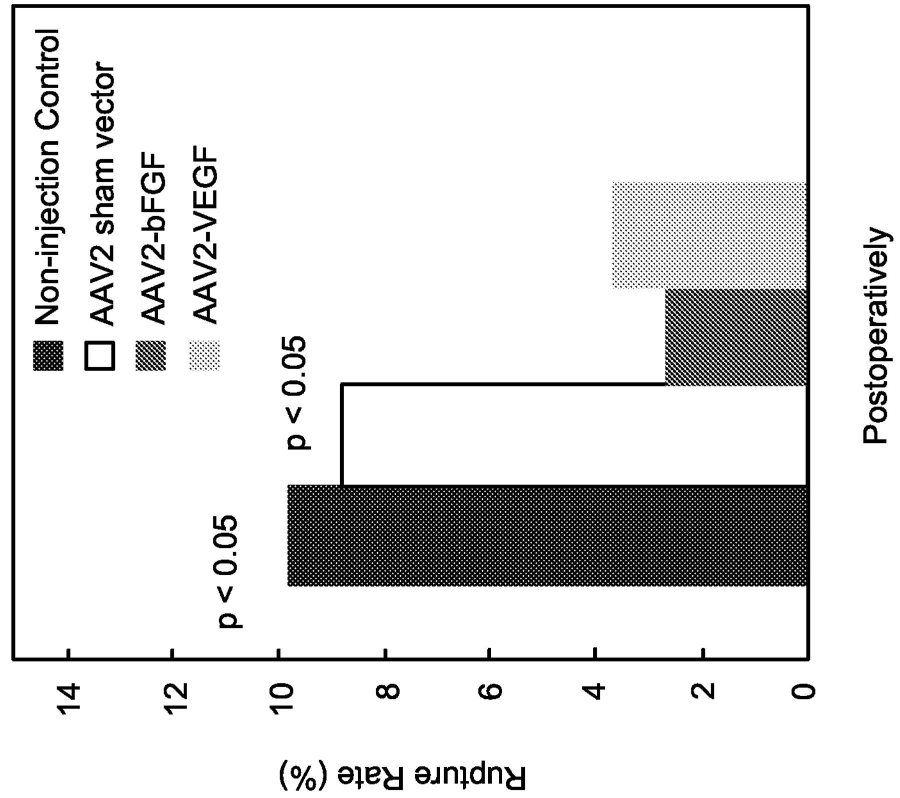
FIG. 5F is a bar graph showing overall rate of tendon ruptures recorded during dissection in the samples for mechanical test at weeks 4, 5, 6, and 8 (48 toes at each group) after surgery. Significant differences in the rupture rate were noted between the AAV2-bFGF or AAV2-VEGF injection, sham vector and non-injection groups. P values shown are comparison of the non-injection and sham vector groups with the AAV2-bFGF or AAV2-VEGF injection groups. The bars of the figure, from left to right, represent non-injection control, AAV2 sham vector, AAV2-bFGF, and AAV2-VEGF respectively.
Figure 5E:
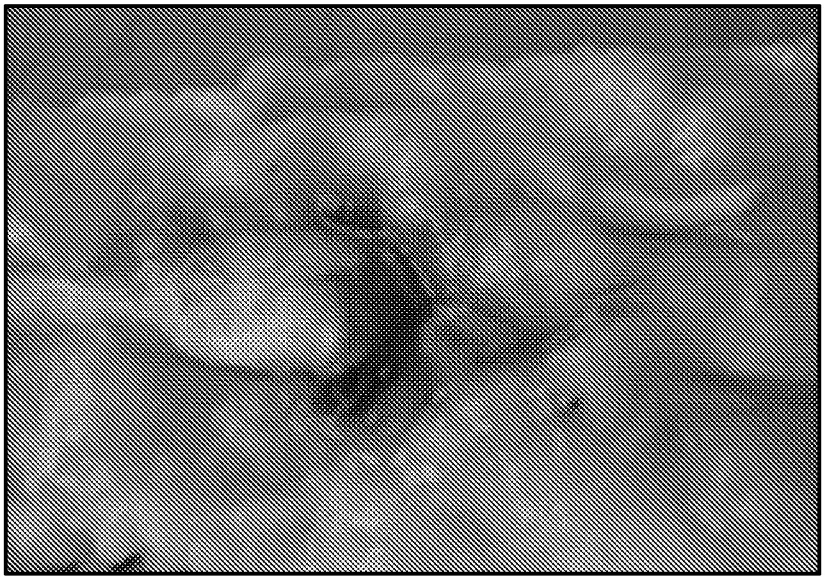
FIG. 5E is a picture showing a typical tendon rupture.
Figure 6D:
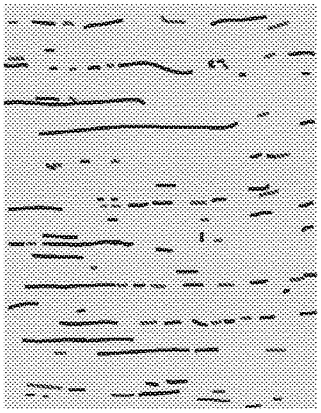
FIGS. 6A-6D are immunohistochemistry staining showing sections of healing tendons and uninjured tendons.
Figure 6C:
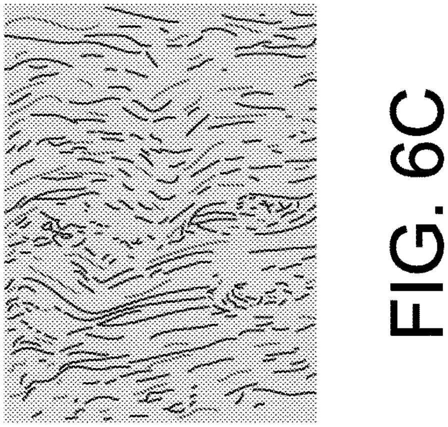
Figure 6B:
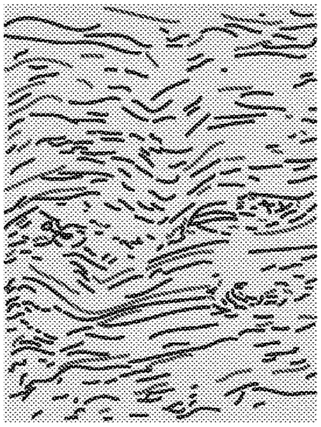
Figure 6A:
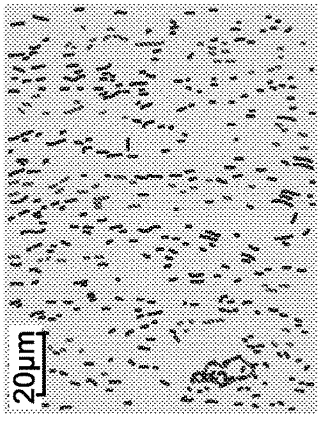
Figure 7:
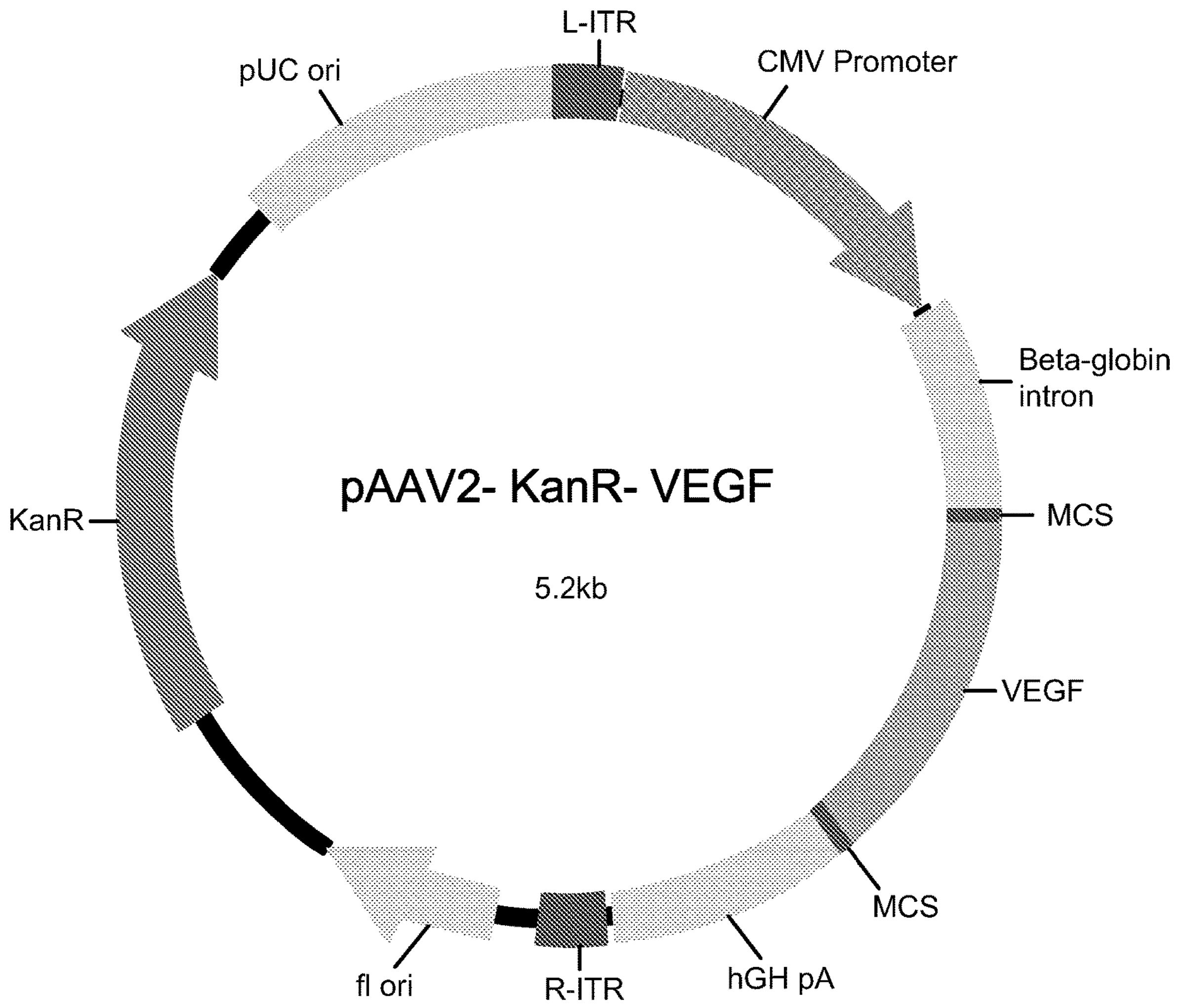

No significant increases in amount of adhesions and in work needed to flex the repaired toes were not found in the treatment groups ($p>0.05$, statistical power $>0.85$) (FIG. 5A-D). The overall rupture rate of repaired tendons was significantly greater in both control groups than in treatment groups ($p<0.01$) (FIG. 5E,F).

Figure 1G:
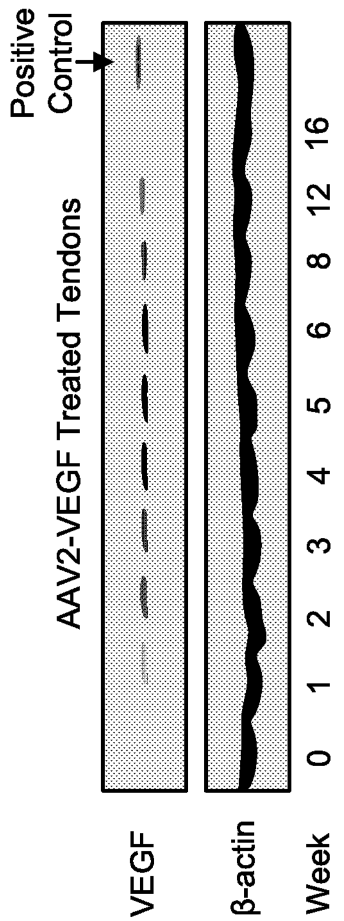
FIG. 1G is a picture of Western Blot showing the changes in human VEGF. The VEGF was not present at week 16. The sample number (n) was 6 for analysis of gene expression and 4 for western blot analysis at each time point in each group.

Production of supranormal amounts of bFGF or VEGF ceases after healing is complete. We measured rat bFGF or human VEGF in the tendon upto 16 weeks (FIG. 1C, 1G); at that point, tendon healing is complete. Both gene expression and amount of bFGF or VEGF protein present in the treated tendons decreased from weeks 12 to 16 to minimal or undetectable levels (FIG. 1A-C,E,F). At week 16, levels of bFGF and VEGF in the treated tendons returned to the levels in non-injection controls (FIG. 1D).

Tendon structures in histology. At week 8 and later, we observed that the histological sections show better structural remodeling with more regularly aligned collagens in the treated tendons compared with sham vectors and in non-injection controls. However, the structures were still not normal even at week 12, which indicates that structural remodeling took more than 8 or 12 weeks. At week 6, the cellularity in the treatment tendons is still more prominent than that in the non-injection controls, and the collagens appeared to be more robust in the treatment groups (FIG. 6A-D).

In this study, delivery of either bFGE or VEGF genes through AAV2 vectors improved the tendon strength in the early and middle healing stages. Notably, this gain of strength is achieved without the cost of increase in associated adhesion formation or resistance to tendon gliding. This therapy offers a highly efficient way of improving tendon strength. The impact of this therapeutic approach is impressive in our animal model, producing an increase in strength by 68 to 210%, which is likely ample to prevent tendon gapping or disunion of the tendons. This study illustrates a way through which intrinsic healing capacity is enhanced and the "no-gain" period of tendon strength recovery in the initial a few weeks after repair can be converted to a steady gain in the period when the tendon frequently disrupts.

No increase was found in resistance to tendon motion or severity of adhesion in the tendon treated with AAV2-bFGF or AAV2-VEGF as compared with non-treatment and sham vector controls. Notably, expression of type III collagen was down-regulated from weeks 1 to 4 after AAV2-bFGF treatment and at week 1 to 2 after AAV2-VEGF treatment (FIG. 2D); thereafter the type III collagen expression increased to the level identical to that of the non-injection controls. The increase in type III collagen at week 6 would not increase the amount of adhesions, because adhesions form around the tendon form during the first weeks of the healing tendon. In the later healing, adhesions do not increase but rather remodel to allow greater tendon gliding. Down-regulating type III collagen in the first a few weeks after surgery lead to deposition of a greater amount of mature collagen (type I collagen), favoring earlier gain in the strength.

Our findings regarding changes in the extracellular matrix (and its regulators) provide additional mechanistic explanation for gain in the strength of the treated tendons. With AAV2-bFGF and AAV2-VEGF treatment, MMPs were down-regulated and TIMPs were up-regulated; both of these changes act to slow down degradation of extracellular matrix. In addition, the increases in proliferation rate of tendon fibroblasts were paired with inhibition of cell apoptosis. The mechanism of these therapies, therefore, is likely an initial increase in tendon cell proliferation paired with inhibition of cellular apoptosis, followed by supernormal production of type I collagen with inhibition of type III collagen, and an overall slow-down of collagen degradation as a result of changes in activities of MMPs and TTMPs. Our findings suggest that these molecular events effectively transform a lengthy inactive early-to-middle healing period to a biologically robust healing period, leading to impressive gain of strength.

This preclinical animal experiment demonstrated great efficacy for treating tendon injury. The micro-injection of AAV vectors to the tendons is simple, yet effective. The AAV vectors have been used in a number of animal studies and clinical trials, and thus far, have been safe. We verified that these vectors were not expressed in vital organs (i.e., brain, heart, lung, liver, ovary, etc.). Although our data indicate similar treatment efficacy profiles, we noted slightly different effects between AAV2-bFGF and AAV2-VEGF. Our mechanical tests showed that neither therapy potentiates adhesion formation around healing tendons. All these findings make both studied therapies appropriate candidates for clinical trials. This study showed that both therapeutic approaches are appropriate for clinical trials and hold great promise of correcting weak healing potential of the intrasynovial tendon to combat different problems associated with tendon repair in the clinical arena.

Methods

Chicken tendon injury, surgical repair model and group division. The animal experimentation was conducted in accordance with the approved guidelines of Nantong University and National Experimental Animal Regulation. This study was approved by the Experimental Animal Care Committee of Nantong University.

Animals. Adult white Leghorn chickens were used as experimental models, because the flexor tendons in chicken toes are similar to those in human digits and are often used for investigation of digital flexor tendon surgery. Among 263 chickens were used for this study, 12 chickens were used for obtaining data of strengths in healthy tendons and 53 chickens for testing strength of the tendons immediately after surgical repair, or obtaining molecular and histological data in healthy tendons or tendon with only surgical repair. 198 chickens (396 long toes of both feet) were used for mechanical tests and/or harvesting tendon samples for analysis of gene expression, western blot analysis of proteins, or histological examination.

Surgical Procedures and Groups. The long toes of chickens were randomly assigned to 4 experimental arms according to differing treatments administered at surgery. The chickens were anesthetized by intramuscular injection with ketamine (50 mg/kg of body weight). The toes were operated under sterile conditions and tourniquet control using elastic bandages. A zigzag incision was made in the plantar skin between the proximal interphalan-geal (PIP) and distal interphalangeal (DIP) joints, which is equivalent to zone 2 in the human hand. Through a 1.0-cm long longitudinal incision through the tendon sheath, a transverse cut of the FDP tendon was made with a sharp scalpel at the level about 1.0 cm distal to the PIP joint with the toe in extension. The long toes were divided as follows:

Group 1. Non-treatment control. Tendons did not receive any injection. Group 2. Sham-vector treatment control: $2\times10^9$ vp of AAV2 sham vector diluted in 20 tl of physiological saline were injected into each tendon. Group 3. AAV2-bFGF injection group: $2\times10^9$ vp of AAV2-bFGF in 20 tl of physiological saline were injected into each tendon. Group 4. AAV2-VEGF injection group: $2\times10^9$ vp of AAV2-VEGF in 20 tl of physiological saline were injected.

The cut tendon was repaired with the modified Kessler method with 5-0 sutures (Ethilon; Ethicon, Somerville, New Jersey). The incised sheath was left open and the skin was closed with interrupted sutures. The operated toes were immobilized in a dressing wrap with adhesive tape in a semiflexed position after surgery.

A micro-injection needle was used for vector injection through the lacerated tendon cross-sectional surface at the depth of 0.5 cm at four sites (2 sites in either tendon stump). $5\times10^8$ particles of AAV2-bFGF vector were injected to each of four sites in the stumps of the cut tendon ends before repair, yielding a total injected dose of $2\times10^9$ in each tendon.

The operated toes were divided into subgroups according to the timing of harvest at postoperative day 0, and weeks 1, 2, 3, 4, 5, 6, 8, 12, and 16.

Gene Transfer Units—AAV2-bFGF and AAV2-VEGF—Vector Construction and Production. Single-stranded AAV2 vectors were used. The AAV2-bFGF vector plasmid was constructed as we described in previous publications. The bFGF gene is of rat origin (Gene bank accession no. X07285). The AAV2-VEGF vector plasmid pAAV2-VEGF was constructed by inserting human VEGF gene (Gene bank accession no. AF486837) encoding human VEGF 165 isoform into pAAV-MCS (Stratagene, La Jolla, Calif) The AAV2 sham vector plasmid was purchased from Stratagene. AAV2-bFGF, AAV2-VEGF and sham vector were subsequently produced and purified in Vector BioLabs (Philadelphia, Penn.).

Real-time PCR. Total RNA was isolated and was reversely transcripted to complementary DNA (cDNA). Expression of genes was analyzed by real-time quantitative polymerase chain reactions (qPCR) using the Eppendorf Mastercycler ep realplex (2S; Eppendorf, Hamburg, Germany). Expression of the transcriptions was normalized to the GAPDH gene to standardize comparison.

Immunohistochemistry and immunofluorescence. After harvest, the tendons underwent fixation with 4% paraformaldehyde, paraffin-embedding, rehydration, and longitudinal sectioning into 4t m thick sections. The immunohistochemistry was performed to detect rat bFGF in sections. The specimens were stained overnight with mouse anti-rat bFGF (05-118, Millipore Corp., Billerica, Mass.), mouse anti-chicken PCNA antibody (ab29, Abcam, Cambridge, Mass.) at 1:3000 dilution in a humid chamber at 4 °C. The immunofluorescence was performed to examine tenocyte proliferation. For the sections with PCNA staining, the localizations of the PCNA protein were then visualized by incubating with fluorescein isothiocyanate-conjugated goat anti-mouse immunoglobulin G (ICL, Inc, Newberg, Oregon) at 1:200 dilution.

In situ TUNEL Assay. Detection of cell death in the histological tissue section was done by TUNEL assay kit (Roche, Mannheim, Germany) according to the manufacturer's protocol. Paraffin-embedded tissues were sectioned and incubated with TUNEL reaction mixture for 1 hour at 37 °C in a humidified chamber. Converter-Peroxidase (POD) solution was applied and the slides were incubated. The slides were incubated at ambient temperature after addition of the chromogenic substrate 3,3-diaminobenzidine (DAB), and were counterstained with Mayer's hematoxylin.

Western blot. The tendon samples were homogenized. Protein content was normalized and the samples were subjected to SDS-polyacrylamide gel electrophoresis and transferred onto a polyvinylidene difluoride membrane filter (Millipore Corp., Billerica, Mass.). The filters were incubated in phosphate-buffered saline containing 0.5% Tween 20 and 5% nonfat milk and then incubated with primary antibody overnight at 4 °C. After incubation with conjugated affinity-purified secondary antibody labeled with IRDye 800, blots were washed and immunoreactive proteins were scanned on an Odyssey imager (LI-COR, Inc., Lincoln, NE). Optical density on the membrane was measured and the relative differences between an internal control (ß-actin) and treated samples were calculated. Mouse anti-rat bFGF (Milipore Corp., Billerica, Mass.), mouse anti-human VEGF (Santa Cruz, Dallas, Texas), mouse anti-chicken MMP2 and TIMP2 (Abcam, Cambridge, Mass.) and mouse anti-chicken type I collagen and type III collagen (Acris, San Diego, Calif.) were used respectively as primary antibodies to detect different proteins.

Quantification scoring of adhesion tissue of the tendons. An established grading method was used for grading adhesions macroscopically. With use of software (Reconstruct, Version 1.1.0.0; John C. Fiala, Boston, MA) for three-dimensional (3-D) reconstruction and alignment of serially sectioned samples of the tendons, we could verify the extent of adhesions recorded in the samples. We reconstructed the adhesions with tendons over a length of 1 cm. We applied the same 3-D reconstruction methodology to align sections stained with in situ TUNEL assay to examine the differences between apoptotic cells in the tendon surface and core.

Biomechanical test of the healing strength. We harvested the FDP tendon through its entire length for the test of tendon strength in an Instron tensile testing machine (model 4411; Instron Inc., Norwood, Mass.). The distal phalanx attached with the terminal FDP tendon was mounted in the lower clamp of the machine. The proximal tendon end was mounted in the upper clamp. The length of the tendon was 8 cm between the two clamps with the repair site was maintained at the middle. The tendon was distracted linearly at a constant speed of 25 mm/min. The load on the tendons was continuously measured until ultimate failure, which was indicated by a sharp decline in load displacement shown on the monitor and abrupt disruption at the repair site. The forces were measured to the nearest 0.1N.

Biomechanical test of resistance to the tendon: work of flexion and gliding excursion. The toes for quantifying resistance to toe motion were harvested through amputation at the knee joint and were mounted on a platform attached to the lower clamp of the testing machine (Instron). The proximal tendon was connected to the upper clamp. Both tendon gliding and work of toe flexion indicate resistance to digital motion, as mechanical measures of severity of adhesion formation. With this setup, we measured FDP tendon excursion under a fixed load, and the work of toe flexion, i.e., the energy required to flex the toe over a fixed for 70-degree from full extension. In testing the excursion, all toe joints were unrestricted, and tendon excursion was tested during the first run and work of flexion at the second run.

Quantification and Statistics. Data are expressed as mean±SD. In performing western blot analysis, we measured the density of target and control bands with a computer-assisted imaging analysis system. We counted the number of PCNA positively stained cells under fluorescence microscope. Ultimate tendon strength and gliding excursion were obtained from direct readout of the monitor. The load-displacement graph was recorded by the testing machine and energy required for digital flexion is work of flexion. Differences in gene expression, protein amount, and number of positively stained cells after PCNA or TUNEL staining, adhesion scores, tendon strengths, work of flexion, and tendon excursions were analyzed with two-way repeated measure of analysis of variance. A Tukey's HSD test with Holm-Bonferroni correction was used as a post hoc test to detect significance between each pair of data comparisons. The criterion for statistical significance was $P<0.05$.

What is claimed is:

1. A method of treating an injury of a fibrous connective tissue in a subject in need thereof, wherein the subject is a mammal, the method consisting of administering to said subject a therapeutically effective amount of a polynucleotide consisting essentially of a pUC origin of replication, an AAV left inverted terminal repeat sequence, a CMV promoter, a beta globin intron, a first multiple cloning site, a sequence encoding vascular endothelial growth factor (VEGF), a second multiple cloning site, a human growth hormone polyadenylation signal, an AAV right inverted terminal repeat sequence, an f1 origin of replication, and a sequence encoding a gene product for kanamycin resistance;

wherein said polynucleotide is formulated as a solution, a gel, a paste, a powder, or a suspension;

wherein said polynucleotide is locally administered directly into or onto said fibrous connective tissue;

wherein said fibrous connective tissue is a ligament or a tendon;

wherein the cells in said fibrous connective tissue take up the polynucleotide and express the encoded VEGF or fragment thereof;

such that the encoded VEGF or fragment thereof is delivered locally to said fibrous connective tissue.

2. The method of claim 1, wherein said sequence encoding a gene product for kanamycin resistance consists essentially of the sequence of SEQ ID NO: 10.

3. The method of claim 2, wherein said polynucleotide consists essentially of the sequence of SEQ ID NO: 11.

4. The method of claim 1, wherein said polynucleotide sequence encoding VEGF consists essentially of a nucleic acid sequence of any one of SEQ ID NOs: 1-9.

5. The method of claim 1, wherein said polynucleotide sequence encoding VEGF consists essentially of the nucleic acid sequence of SEQ ID NO: 9.

6. The method of claim 1, wherein the polynucleotide is administered via a micro-injection needle.

7. The method of claim 1, wherein said administration is into cut ends of said fibrous connective tissue.

8. The method of claim 1, wherein said administration is directly orthogonal to the injury of said fibrous connective tissue.

9. The method of claim 1, wherein said administration is at an angle to the injury of said fibrous connective tissue.

* * * * *

SEQUENCE LISTING

<160> NUMBER OF SEQ ID NOS: 11

<210> SEQ ID NO 1
<211> LENGTH: 3677
<212> TYPE: DNA
<213> ORGANISM: Homo sapiens

<400> SEQUENCE: 1

```
tcgcggaggc ttggggcagc cgggtagctc ggaggtcgtg gcgctggggg ctagcaccag     60

cgctctgtcg ggaggcgcag cggttaggtg gaccggtcag cggactcacc ggccagggcg    120

ctcggtgctg gaatttgata ttcattgatc cgggttttat ccctcttctt ttttcttaaa    180

catttttttt taaaactgta ttgtttctcg ttttaattta tttttgcttg ccattcccca    240

cttgaatcgg gccgacggct tggggagatt gctctacttc cccaaatcac tgtggatttt    300

ggaaaccagc agaaagagga aagaggtagc aagagctcca gagagaagtc gaggaagaga    360

gagacggggt cagagagagc gcgcgggcgt gcgagcagcg aaagcgacag gggcaaagtg    420

agtgacctgc ttttgggggt gaccgccgga gcgcggcgtg agccctcccc cttgggatcc    480

cgcagctgac cagtcgcgct gacggacaga cagacagaca ccgcccccag ccccagctac    540

cacctcctcc ccggccggcg gcggacagtg gacgcggcgg cgagccgcgg gcaggggccg    600

gagcccgcgc ccggaggcgg ggtggagggg gtcggggctc gcggcgtcgc actgaaactt    660

ttcgtccaac ttctgggctg ttctcgcttc ggaggagccg tggtccgcgc gggggaagcc    720

gagccgagcg gagccgcgag aagtgctagc tcgggccggg aggagccgca gccggaggag    780

ggggaggagg aagaagagaa ggaagaggag agggggccgc agtggcgact cggcgctcgg    840

aagccgggct catggacggg tgaggcggcg gtgtgcgcag acagtgctcc agccgcgcgc    900

gctccccagg ccctggcccg ggcctcgggc cggggaggaa gagtagctcg ccgaggcgcc    960

gaggagagcg ggccgcccca cagcccgagc cggagaggga gcgcgagccg cgccggcccc   1020

ggtcgggcct ccgaaaccat gaactttctg ctgtcttggg tgcattggag ccttgccttg   1080

ctgctctacc tccaccatgc caagtggtcc caggctgcac ccatggcaga aggaggaggg   1140

cagaatcatc acgaagtggt gaagttcatg gatgtctatc agcgcagcta ctgccatcca   1200

atcgagaccc tggtggacat cttccaggag taccctgatg agatcgagta catcttcaag   1260

ccatcctgtg tgcccctgat gcgatgcggg ggctgctgca atgacgaggg cctggagtgt   1320

gtgcccactg aggagtccaa catcaccatg cagattatgc ggatcaaacc tcaccaaggc   1380

cagcacatag gagagatgag cttcctacag cacaacaaat gtgaatgcag accaaagaaa   1440

gatagagcaa gacaagaaaa aaaatcagtt cgaggaaagg gaaaggggca aaaacgaaag   1500

cgcaagaaat cccggtataa gtcctggagc gtgtacgttg gtgcccgctg ctgtctaatg   1560

ccctggagcc tccctggccc ccatccctgt gggccttgct cagagcggag aaagcatttg   1620

tttgtacaag atccgcagac gtgtaaatgt tcctgcaaaa acacagactc gcgttgcaag   1680

gcgaggcagc ttgagttaaa cgaacgtact tgcagatgtg acaagccgag gcggtgagcc   1740

gggcaggagg aaggagcctc cctcagggtt tcgggaacca gatctctcac caggaaagac   1800

tgatacagaa cgatcgatac agaaaccacg ctgccgccac cacaccatca ccatcgacag   1860

aacagtcctt aatccagaaa cctgaaatga aggaagagga gactctgcgc agagcacttt   1920

gggtccggag ggcgagactc cggcggaagc attcccgggc gggtgaccca gcacggtccc   1980

tcttggaatt ggattcgcca ttttattttt cttgctgcta aatcaccgag cccggaagat   2040

tagagagttt tatttctggg attcctgtag acacacccac ccacatacat acatttatat   2100
```

```
atatatatat tatatatata taaaaataaa tatctctatt ttatatatat aaaatatata   2160

tattcttttt ttaaattaac agtgctaatg ttattggtgt cttcactgga tgtatttgac   2220

tgctgtggac ttgagttggg aggggaatgt tcccactcag atcctgacag ggaagaggag   2280

gagatgagag actctggcat gatctttttt ttgtcccact tggtggggcc agggtcctct   2340

cccctgccca ggaatgtgca aggccagggc atgggggcaa atatgaccca gttttgggaa   2400

caccgacaaa cccagccctg gcgctgagcc tctctacccc aggtcagacg gacagaaaga   2460

cagatcacag gtacagggat gaggacaccg gctctgacca ggagtttggg gagcttcagg   2520

acattgctgt gctttgggga ttccctccac atgctgcacg cgcatctcgc ccccaggggc   2580

actgcctgga agattcagga gcctgggcgg ccttcgctta ctctcacctg cttctgagtt   2640

gcccaggaga ccactggcag atgtcccggc gaagagaaga gacacattgt tggaagaagc   2700

agcccatgac agctcccctt cctgggactc gccctcatcc tcttcctgct ccccttcctg   2760

gggtgcagcc taaaaggacc tatgtcctca caccattgaa accactagtt ctgtcccccc   2820

aggagacctg gttgtgtgtg tgtgagtggt tgaccttcct ccatcccctg gtccttccct   2880

tcccttcccg aggcacagag agacagggca ggatccacgt gcccattgtg gaggcagaga   2940

aaagagaaag tgttttatat acggtactta tttaatatcc ctttttaatt agaaattaaa   3000

acagttaatt taattaaaga gtagggtttt ttttcagtat tcttggttaa tatttaattt   3060

caactattta tgagatgtat cttttgctct ctcttgctct cttatttgta ccggtttttg   3120

tatataaaat tcatgtttcc aatctctctc tccctgatcg gtgacagtca ctagcttatc   3180

ttgaacagat atttaatttt gctaacactc agctctgccc tccccgatcc cctggctccc   3240

cagcacacat tcctttgaaa taaggtttca atatacatct acatactata tatatatttg   3300

gcaacttgta tttgtgtgta tatatatata tatatgttta tgtatatatg tgattctgat   3360

aaaatagaca ttgctattct gtttttttata tgtaaaaaca aaacaagaaa aaatagagaa   3420

ttctacatac taaatctctc tcctttttta attttaatat ttgttatcat ttatttattg   3480

gtgctactgt ttatccgtaa taattgtggg gaaaagatat taacatcacg tctttgtctc   3540

tagtgcagtt tttcgagata ttccgtagta catatttatt tttaaacaac gacaaagaaa   3600

tacagatata tcttaaaaaa aaaaaagcat tttgtattaa agaatttaat tctgatctca   3660

aaaaaaaaaa aaaaaaa                                                  3677
```

<210> SEQ ID NO 2
<211> LENGTH: 3626
<212> TYPE: DNA
<213> ORGANISM: Homo sapiens

<400> SEQUENCE: 2

```
tcgcggaggc ttggggcagc cgggtagctc ggaggtcgtg gcgctggggg ctagcaccag     60

cgctctgtcg ggaggcgcag cggttaggtg gaccggtcag cggactcacc ggccagggcg    120

ctcggtgctg gaatttgata ttcattgatc cgggttttat ccctcttctt ttttcttaaa    180

catttttttt taaaactgta ttgtttctcg ttttaattta tttttgcttg ccattcccca    240

cttgaatcgg gccgacggct tggggagatt gctctacttc cccaaatcac tgtggatttt    300

ggaaaccagc agaaagagga aagaggtagc aagagctcca gagagaagtc gaggaagaga    360

gagacggggt cagagagagc gcgcgggcgt gcgagcagcg aaagcgacag gggcaaagtg    420

agtgacctgc ttttgggggt gaccgccgga gcgcggcgtg agccctcccc cttgggatcc    480
```

-continued

```
cgcagctgac cagtcgcgct gacggacaga cagacagaca ccgcccccag ccccagctac    540

cacctcctcc ccggccggcg gcggacagtg gacgcggcgg cgagccgcgg gcaggggccg    600

gagcccgcgc ccggaggcgg ggtggagggg gtcggggctc gcggcgtcgc actgaaactt    660

ttcgtccaac ttctgggctg ttctcgcttc ggaggagccg tggtccgcgc gggggaagcc    720

gagccgagcg gagccgcgag aagtgctagc tcgggccggg aggagccgca gccggaggag    780

ggggaggagg aagaagagaa ggaagaggag agggggccgc agtggcgact cggcgctcgg    840

aagccgggct catggacggg tgaggcggcg gtgtgcgcag acagtgctcc agccgcgcgc    900

gctccccagg ccctggcccg ggcctcgggc cggggaggaa gagtagctcg ccgaggcgcc    960

gaggagagcg ggccgcccca cagcccgagc cggagaggga gcgcgagccg cgccggcccc   1020

ggtcgggcct ccgaaaccat gaactttctg ctgtcttggg tgcattggag ccttgccttg   1080

ctgctctacc tccaccatgc caagtggtcc caggctgcac ccatggcaga aggaggaggg   1140

cagaatcatc acgaagtggt gaagttcatg gatgtctatc agcgcagcta ctgccatcca   1200

atcgagaccc tggtggacat cttccaggag taccctgatg agatcgagta catcttcaag   1260

ccatcctgtg tgcccctgat gcgatgcggg ggctgctgca atgacgaggg cctggagtgt   1320

gtgcccactg aggagtccaa catcaccatg cagattatgc ggatcaaacc tcaccaaggc   1380

cagcacatag gagagatgag cttcctacag cacaacaaat gtgaatgcag accaaagaaa   1440

gatagagcaa gacaagaaaa aaaatcagtt cgaggaaagg gaaaggggca aaaacgaaag   1500

cgcaagaaat cccggtataa gtcctggagc gttccctgtg ggccttgctc agagcggaga   1560

aagcatttgt ttgtacaaga tccgcagacg tgtaaatgtt cctgcaaaaa cacagactcg   1620

cgttgcaagg cgaggcagct tgagttaaac gaacgtactt gcagatgtga caagccgagg   1680

cggtgagccg ggcaggagga aggagcctcc ctcagggttt cgggaaccag atctctcacc   1740

aggaaagact gatacagaac gatcgataca gaaaccacgc tgccgccacc acaccatcac   1800

catcgacaga acagtcctta atccagaaac ctgaaatgaa ggaagaggag actctgcgca   1860

gagcactttg ggtccggagg gcgagactcc ggcggaagca ttcccgggcg ggtgacccag   1920

cacggtccct cttggaattg gattcgccat ttttattttc ttgctgctaa atcaccgagc   1980

ccggaagatt agagagtttt atttctggga ttcctgtaga cacacccacc cacatacata   2040

catttatata tatatatatt atatatatat aaaaataaat atctctattt tatatatata   2100

aaatatatat attctttttt taaattaaca gtgctaatgt tattggtgtc ttcactggat   2160

gtatttgact gctgtggact tgagttggga ggggaatgtt cccactcaga tcctgacagg   2220

gaagaggagg agatgagaga ctctggcatg atcttttttt tgtcccactt ggtggggcca   2280

gggtcctctc ccctgcccag gaatgtgcaa ggccagggca tgggggcaaa tatgacccag   2340

ttttgggaac accgacaaac ccagccctgg cgctgagcct ctctacccca ggtcagacgg   2400

acagaaagac agatcacagg tacagggatg aggacaccgg ctctgaccag gagtttgggg   2460

agcttcagga cattgctgtg ctttggggat tccctccaca tgctgcacgc gcatctcgcc   2520

cccaggggca ctgcctggaa gattcaggag cctgggcggc cttcgcttac tctcacctgc   2580

ttctgagttg cccaggagac cactggcaga tgtcccggcg aagagaagag acacattgtt   2640

ggaagaagca gcccatgaca gctccccttc ctgggactcg ccctcatcct cttcctgctc   2700

cccttcctgg ggtgcagcct aaaaggacct atgtcctcac accattgaaa ccactagttc   2760

tgtcccccca ggagacctgg ttgtgtgtgt gtgagtggtt gaccttcctc catcccctgg   2820

tccttccctt cccttcccga ggcacagaga gacagggcag gatccacgtg cccattgtgg   2880
```

aggcagagaa aagagaaagt gttttatata cggtacttat ttaatatccc tttttaatta 2940
gaaattaaaa cagttaattt aattaaagag tagggttttt tttcagtatt cttggttaat 3000
atttaatttc aactatttat gagatgtatc ttttgctctc tcttgctctc ttatttgtac 3060
cggtttttgt atataaaatt catgtttcca atctctctct ccctgatcgg tgacagtcac 3120
tagcttatct tgaacagata tttaattttg ctaacactca gctctgccct ccccgatccc 3180
ctggctcccc agcacacatt cctttgaaat aaggtttcaa tatacatcta catactatat 3240
atatatttgg caacttgtat ttgtgtgtat atatatatat atatgtttat gtatatatgt 3300
gattctgata aaatagacat tgctattctg ttttttatat gtaaaaacaa aacaagaaaa 3360
aatagagaat tctacatact aaatctctct cctttttttaa ttttaatatt tgttatcatt 3420
tatttattgg tgctactgtt tatccgtaat aattgtgggg aaaagatatt aacatcacgt 3480
ctttgtctct agtgcagttt ttcgagatat tccgtagtac atatttattt ttaaacaacg 3540
acaaagaaat acagatatat cttaaaaaaa aaaaagcatt ttgtattaaa gaatttaatt 3600
ctgatctcaa aaaaaaaaaa aaaaaa 3626

<210> SEQ ID NO 3
<211> LENGTH: 3608
<212> TYPE: DNA
<213> ORGANISM: Homo sapiens

<400> SEQUENCE: 3
tcgcggaggc ttggggcagc cgggtagctc ggaggtcgtg gcgctggggg ctagcaccag 60
cgctctgtcg ggaggcgcag cggttaggtg gaccggtcag cggactcacc ggccagggcg 120
ctcggtgctg gaatttgata ttcattgatc cgggttttat ccctcttctt ttttcttaaa 180
cattttttttt taaaactgta ttgtttctcg ttttaattta tttttgcttg ccattcccca 240
cttgaatcgg gccgacggct tggggagatt gctctacttc cccaaatcac tgtggatttt 300
ggaaaccagc agaaagagga aagaggtagc aagagctcca gagagaagtc gaggaagaga 360
gagacggggt cagagagagc gcgcgggcgt gcgagcagcg aaagcgacag gggcaaagtg 420
agtgacctgc ttttgggggt gaccgccgga gcgcggcgtg agccctcccc cttgggatcc 480
cgcagctgac cagtcgcgct gacggacaga cagacagaca ccgcccccag ccccagctac 540
cacctcctcc ccggccggcg gcggacagtg gacgcggcgg cgagccgcgg gcaggggccg 600
gagcccgcgc ccggaggcgg ggtggagggg gtcggggctc gcggcgtcgc actgaaactt 660
ttcgtccaac ttctgggctg ttctcgcttc ggaggagccg tggtccgcgc gggggaagcc 720
gagccgagcg gagccgcgag aagtgctagc tcgggccggg aggagccgca gccggaggag 780
ggggaggagg aagaagagaa ggaagaggag agggggccgc agtggcgact cggcgctcgg 840
aagccgggct catggacggg tgaggcggcg gtgtgcgcag acagtgctcc agccgcgcgc 900
gctccccagg ccctggcccg ggcctcgggc cggggaggaa gagtagctcg ccgaggcgcc 960
gaggagagcg ggccgcccca cagcccgagc cggagaggga gcgcgagccg cgccggcccc 1020
ggtcgggcct ccgaaaccat gaactttctg ctgtcttggg tgcattggag ccttgccttg 1080
ctgctctacc tccaccatgc caagtggtcc caggctgcac ccatggcaga aggaggaggg 1140
cagaatcatc acgaagtggt gaagttcatg gatgtctatc agcgcagcta ctgccatcca 1200
atcgagaccc tggtggacat cttccaggag taccctgatg agatcgagta catcttcaag 1260
ccatcctgtg tgcccctgat gcgatgcggg ggctgctgca atgacgaggg cctggagtgt 1320

```
gtgcccactg aggagtccaa catcaccatg cagattatgc ggatcaaacc tcaccaaggc   1380
cagcacatag gagagatgag cttcctacag cacaacaaat gtgaatgcag accaaagaaa   1440
gatagagcaa gacaagaaaa aaaatcagtt cgaggaaagg gaaaggggca aaaacgaaag   1500
cgcaagaaat cccgtccctg tgggccttgc tcagagcgga gaaagcattt gtttgtacaa   1560
gatccgcaga cgtgtaaatg ttcctgcaaa aacacagact cgcgttgcaa ggcgaggcag   1620
cttgagttaa acgaacgtac ttgcagatgt gacaagccga ggcggtgagc cgggcaggag   1680
gaaggagcct ccctcagggt ttcgggaacc agatctctca ccaggaaaga ctgatacaga   1740
acgatcgata cagaaaccac gctgccgcca ccacaccatc accatcgaca gaacagtcct   1800
taatccagaa acctgaaatg aaggaagagg agactctgcg cagagcactt tgggtccgga   1860
gggcgagact ccggcggaag cattcccggg cgggtgaccc agcacggtcc ctcttggaat   1920
tggattcgcc attttatttt tcttgctgct aaatcaccga gcccggaaga ttagagagtt   1980
ttatttctgg gattcctgta gacacaccca cccacataca tacatttata tatatatata   2040
ttatatatat ataaaaataa atatctctat tttatatata taaaatatat atattctttt   2100
tttaaattaa cagtgctaat gttattggtg tcttcactgg atgtatttga ctgctgtgga   2160
cttgagttgg gaggggaatg ttcccactca gatcctgaca gggaagagga ggagatgaga   2220
gactctggca tgatcttttt tttgtcccac ttggtggggc cagggtcctc tcccctgccc   2280
aggaatgtgc aaggccaggg catgggggca aatatgaccc agttttggga acaccgacaa   2340
acccagccct ggcgctgagc ctctctaccc caggtcagac ggacagaaag acagatcaca   2400
ggtacaggga tgaggacacc ggctctgacc aggagtttgg ggagcttcag gacattgctg   2460
tgctttgggg attccctcca catgctgcac gcgcatctcg cccccagggg cactgcctgg   2520
aagattcagg agcctgggcg gccttcgctt actctcacct gcttctgagt tgcccaggag   2580
accactggca gatgtcccgg cgaagagaag agacacattg ttggaagaag cagcccatga   2640
cagctcccct tcctgggact cgccctcatc ctcttcctgc tccccttcct ggggtgcagc   2700
ctaaaaggac ctatgtcctc acaccattga aaccactagt tctgtccccc caggagacct   2760
ggttgtgtgt gtgtgagtgg ttgaccttcc tccatcccct ggtccttccc ttcccttccc   2820
gaggcacaga gagacagggc aggatccacg tgcccattgt ggaggcagag aaaagagaaa   2880
gtgttttata tacggtactt atttaatatc cctttttaat tagaaattaa aacagttaat   2940
ttaattaaag agtagggttt tttttcagta ttcttggtta atatttaatt tcaactattt   3000
atgagatgta tcttttgctc tctcttgctc tcttatttgt accggttttt gtatataaaa   3060
ttcatgtttc caatctctct ctccctgatc ggtgacagtc actagcttat cttgaacaga   3120
tatttaattt tgctaacact cagctctgcc ctccccgatc ccctggctcc ccagcacaca   3180
ttcctttgaa ataaggtttc aatatacatc tacatactat atatatattt ggcaacttgt   3240
atttgtgtgt atatatatat atatatgttt atgtatatat gtgattctga taaaatagac   3300
attgctattc tgttttttat atgtaaaaac aaaacaagaa aaaatagaga attctacata   3360
ctaaatctct ctcctttttt aattttaata tttgttatca tttatttatt ggtgctactg   3420
tttatccgta ataattgtgg ggaaaagata ttaacatcac gtctttgtct ctagtgcagt   3480
ttttcgagat attccgtagt acatatttat ttttaaacaa cgacaaagaa atacagatat   3540
atcttaaaaa aaaaaaagca ttttgtatta aagaatttaa ttctgatctc aaaaaaaaaa   3600
aaaaaaaa                                                            3608
```

<210> SEQ ID NO 4
<211> LENGTH: 3554
<212> TYPE: DNA
<213> ORGANISM: Homo sapiens

<400> SEQUENCE: 4
tcgcggaggc ttggggcagc cgggtagctc ggaggtcgtg gcgctggggg ctagcaccag 60
cgctctgtcg ggaggcgcag cggttaggtg gaccggtcag cggactcacc ggccagggcg 120
ctcggtgctg gaatttgata ttcattgatc cgggttttat ccctcttctt ttttcttaaa 180
catttttttt taaaactgta ttgtttctcg ttttaattta tttttgcttg ccattcccca 240
cttgaatcgg gccgacggct tggggagatt gctctacttc cccaaatcac tgtggatttt 300
ggaaaccagc agaaagagga aagaggtagc aagagctcca gagagaagtc gaggaagaga 360
gagacggggt cagagagagc gcgcgggcgt gcgagcagcg aaagcgacag gggcaaagtg 420
agtgacctgc ttttgggggt gaccgccgga gcgcggcgtg agccctcccc cttgggatcc 480
cgcagctgac cagtcgcgct gacggacaga cagacagaca ccgcccccag ccccagctac 540
cacctcctcc ccggccggcg gcggacagtg gacgcggcgg cgagccgcgg gcaggggccg 600
gagcccgcgc ccggaggcgg ggtggagggg gtcggggctc gcggcgtcgc actgaaactt 660
ttcgtccaac ttctgggctg ttctcgcttc ggaggagccg tggtccgcgc gggggaagcc 720
gagccgagcg gagccgcgag aagtgctagc tcgggccggg aggagccgca gccggaggag 780
ggggaggagg aagaagagaa ggaagaggag agggggccgc agtggcgact cggcgctcgg 840
aagccgggct catggacggg tgaggcggcg gtgtgcgcag acagtgctcc agccgcgcgc 900
gctccccagg ccctggcccg ggcctcgggc cggggaggaa gagtagctcg ccgaggcgcc 960
gaggagagcg ggccgcccca cagcccgagc cggagaggga gcgcgagccg cgccggcccc 1020
ggtcgggcct ccgaaaccat gaactttctg ctgtcttggg tgcattggag ccttgccttg 1080
ctgctctacc tccaccatgc caagtggtcc caggctgcac ccatggcaga aggaggaggg 1140
cagaatcatc acgaagtggt gaagttcatg gatgtctatc agcgcagcta ctgccatcca 1200
atcgagaccc tggtggacat cttccaggag taccctgatg agatcgagta catcttcaag 1260
ccatcctgtg tgcccctgat gcgatgcggg ggctgctgca atgacgaggg cctggagtgt 1320
gtgcccactg aggagtccaa catcaccatg cagattatgc ggatcaaacc tcaccaaggc 1380
cagcacatag gagagatgag cttcctacag cacaacaaat gtgaatgcag accaaagaaa 1440
gatagagcaa gacaagaaaa tccctgtggg ccttgctcag agcggagaaa gcatttgttt 1500
gtacaagatc cgcagacgtg taaatgttcc tgcaaaaaca cagactcgcg ttgcaaggcg 1560
aggcagcttg agttaaacga acgtacttgc agatgtgaca agccgaggcg gtgagccggg 1620
caggaggaag gagcctccct cagggtttcg ggaaccagat ctctcaccag gaaagactga 1680
tacagaacga tcgatacaga aaccacgctg ccgccaccac accatcacca tcgacagaac 1740
agtccttaat ccagaaacct gaaatgaagg aagaggagac tctgcgcaga gcactttggg 1800
tccggagggc gagactccgg cggaagcatt cccgggcggg tgacccagca cggtccctct 1860
tggaattgga ttcgccattt tatttttctt gctgctaaat caccgagccc ggaagattag 1920
agagttttat ttctgggatt cctgtagaca cacccaccca catacataca tttatatata 1980
tatatattat atatatataa aaataaatat ctctatttta tatatataaa atatatatat 2040
tcttttttta aattaacagt gctaatgtta ttggtgtctt cactggatgt atttgactgc 2100
tgtggacttg agttgggagg ggaatgttcc cactcagatc ctgacaggga agaggaggag 2160
atgagagact ctggcatgat cttttttttg tcccacttgg tggggccagg gtcctctccc 2220
ctgcccagga atgtgcaagg ccagggcatg ggggcaaata tgacccagtt ttgggaacac 2280
cgacaaaccc agccctggcg ctgagcctct ctaccccagg tcagacggac agaaagacag 2340
atcacaggta cagggatgag gacaccggct ctgaccagga gtttggggag cttcaggaca 2400
ttgctgtgct ttggggattc cctccacatg ctgcacgcgc atctcgcccc caggggcact 2460
gcctggaaga ttcaggagcc tggcggcct tcgcttactc tcacctgctt ctgagttgcc 2520
caggagacca ctggcagatg tcccggcgaa gagaagagac acattgttgg aagaagcagc 2580
ccatgacagc tccccttcct gggactcgcc ctcatcctct tcctgctccc cttcctgggg 2640
tgcagcctaa aaggacctat gtcctcacac cattgaaacc actagttctg tccccccagg 2700
agacctggtt gtgtgtgtgt gagtggttga ccttcctcca tcccctggtc cttcccttcc 2760
cttcccgagg cacagagaga cagggcagga tccacgtgcc cattgtggag gcagagaaaa 2820
gagaaagtgt tttatatacg gtacttattt aatatccctt tttaattaga aattaaaaca 2880
gttaatttaa ttaaagagta gggttttttt tcagtattct tggttaatat ttaatttcaa 2940
ctatttatga gatgtatctt ttgctctctc ttgctctctt atttgtaccg gtttttgtat 3000
ataaaattca tgtttccaat ctctctctcc ctgatcggtg acagtcacta gcttatcttg 3060
aacagatatt taattttgct aacactcagc tctgccctcc ccgatcccct ggctccccag 3120
cacacattcc tttgaaataa ggtttcaata tacatctaca tactatatat atatttggca 3180
acttgtattt gtgtgtatat atatatatat atgtttatgt atatatgtga ttctgataaa 3240
atagacattg ctattctgtt ttttatatgt aaaaacaaaa caagaaaaaa tagagaattc 3300
tacatactaa atctctctcc ttttttaatt ttaatatttg ttatcattta tttattggtg 3360
ctactgttta tccgtaataa ttgtggggaa aagatattaa catcacgtct ttgtctctag 3420
tgcagttttt cgagatattc cgtagtacat atttattttt aaacaacgac aaagaaatac 3480
agatatatct taaaaaaaaa aaagcatttt gtattaaaga atttaattct gatctcaaaa 3540
aaaaaaaaaa aaaa 3554

<210> SEQ ID NO 5
<211> LENGTH: 3519
<212> TYPE: DNA
<213> ORGANISM: Homo sapiens

<400> SEQUENCE: 5
tcgcggaggc ttggggcagc cgggtagctc ggaggtcgtg gcgctggggg ctagcaccag 60
cgctctgtcg ggaggcgcag cggttaggtg gaccggtcag cggactcacc ggccagggcg 120
ctcggtgctg gaatttgata ttcattgatc cgggttttat ccctcttctt ttttcttaaa 180
catttttttt taaaactgta ttgtttctcg ttttaattta tttttgcttg ccattcccca 240
cttgaatcgg gccgacggct tggggagatt gctctacttc cccaaatcac tgtggatttt 300
ggaaaccagc agaaagagga aagaggtagc aagagctcca gagagaagtc gaggaagaga 360
gagacggggt cagagagagc gcgcgggcgt gcgagcagcg aaagcgacag gggcaaagtg 420
agtgacctgc ttttgggggt gaccgccgga gcgcggcgtg agccctcccc cttgggatcc 480
cgcagctgac cagtcgcgct gacggacaga cagacagaca ccgcccccag ccccagctac 540
cacctcctcc ccggccggcg gcggacagtg gacgcggcgg cgagccgcgg gcaggggccg 600
gagcccgcgc ccggaggcgg ggtggagggg gtcggggctc gcggcgtcgc actgaaactt 660
ttcgtccaac ttctgggctg ttctcgcttc ggaggagccg tggtccgcgc gggggaagcc 720

```
gagccgagcg gagccgcgag aagtgctagc tcgggccggg aggagccgca gccggaggag    780
ggggaggagg aagaagagaa ggaagaggag agggggccgc agtggcgact cggcgctcgg    840
aagccgggct catggacggg tgaggcggcg gtgtgcgcag acagtgctcc agccgcgcgc    900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc   1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag gagagatgag cttcctacag cacaacaaat gtgaatgcag accaaagaaa   1440
gatagagcaa gacaagaaaa tccctgtggg ccttgctcag agcggagaaa gcatttgttt   1500
gtacaagatc cgcagacgtg taaatgttcc tgcaaaaaca cagactcgcg ttgcaagatg   1560
tgacaagccg aggcggtgag ccgggcagga ggaaggagcc tccctcaggg tttcgggaac   1620
cagatctctc accaggaaag actgatacag aacgatcgat acagaaacca cgctgccgcc   1680
accacaccat caccatcgac agaacagtcc ttaatccaga aacctgaaat gaaggaagag   1740
gagactctgc gcagagcact ttgggtccgg agggcgagac tccggcggaa gcattcccgg   1800
gcgggtgacc cagcacggtc cctcttggaa ttggattcgc cattttattt ttcttgctgc   1860
taaatcaccg agcccggaag attagagagt tttatttctg ggattcctgt agacacaccc   1920
acccacatac atacatttat atatatatat attatatata tataaaaata aatatctcta   1980
ttttatatat ataaaatata tatattcttt ttttaaatta acagtgctaa tgttattggt   2040
gtcttcactg gatgtatttg actgctgtgg acttgagttg ggaggggaat gttcccactc   2100
agatcctgac agggaagagg aggagatgag agactctggc atgatctttt ttttgtccca   2160
cttggtgggg ccagggtcct ctcccctgcc caggaatgtg caaggccagg gcatgggggc   2220
aaatatgacc cagttttggg aacaccgaca aacccagccc tggcgctgag cctctctacc   2280
ccaggtcaga cggacagaaa gacagatcac aggtacaggg atgaggacac cggctctgac   2340
caggagtttg gggagcttca ggacattgct gtgctttggg gattccctcc acatgctgca   2400
cgcgcatctc gcccccaggg gcactgcctg gaagattcag gagcctgggc ggccttcgct   2460
tactctcacc tgcttctgag ttgcccagga gaccactggc agatgtcccg gcgaagagaa   2520
gagacacatt gttggaagaa gcagcccatg acagctcccc ttcctgggac tcgccctcat   2580
cctcttcctg ctccccttcc tggggtgcag cctaaaagga cctatgtcct cacaccattg   2640
aaaccactag ttctgtcccc ccaggagacc tggttgtgtg tgtgtgagtg gttgaccttc   2700
ctccatcccc tggtccttcc cttcccttcc cgaggcacag agagacaggg caggatccac   2760
gtgcccattg tggaggcaga gaaaagagaa agtgttttat atacggtact tatttaatat   2820
ccctttttaa ttagaaatta aaacagttaa tttaattaaa gagtagggtt ttttttcagt   2880
attcttggtt aatatttaat ttcaactatt tatgagatgt atcttttgct ctctcttgct   2940
ctcttatttg taccggtttt tgtatataaa attcatgttt ccaatctctc tctccctgat   3000
cggtgacagt cactagctta tcttgaacag atatttaatt ttgctaacac tcagctctgc   3060
```

```
cctccccgat cccctggctc cccagcacac attcctttga aataaggttt caatatacat   3120

ctacatacta tatatatatt tggcaacttg tatttgtgtg tatatatata tatatatgtt   3180

tatgtatata tgtgattctg ataaaataga cattgctatt ctgtttttta tatgtaaaaa   3240

caaaacaaga aaaaatagag aattctacat actaaatctc tctccttttt taattttaat   3300

atttgttatc atttatttat tggtgctact gtttatccgt aataattgtg gggaaaagat   3360

attaacatca cgtctttgtc tctagtgcag tttttcgaga tattccgtag tacatattta   3420

tttttaaaca acgacaaaga aatacagata tatcttaaaa aaaaaaaagc attttgtatt   3480

aaagaattta attctgatct caaaaaaaaa aaaaaaaaa                          3519
```

<210> SEQ ID NO 6
<211> LENGTH: 3422
<212> TYPE: DNA
<213> ORGANISM: Homo sapiens

<400> SEQUENCE: 6

```
tcgcggaggc ttggggcagc cgggtagctc ggaggtcgtg gcgctggggg ctagcaccag     60

cgctctgtcg ggaggcgcag cggttaggtg gaccggtcag cggactcacc ggccagggcg    120

ctcggtgctg gaatttgata ttcattgatc cgggttttat ccctcttctt ttttcttaaa    180

catttttttt taaaactgta ttgtttctcg ttttaattta tttttgcttg ccattcccca    240

cttgaatcgg gccgacggct tggggagatt gctctacttc cccaaatcac tgtggatttt    300

ggaaaccagc agaaagagga aagaggtagc aagagctcca gagagaagtc gaggaagaga    360

gagacggggt cagagagagc gcgcgggcgt gcgagcagcg aaagcgacag gggcaaagtg    420

agtgacctgc ttttgggggt gaccgccgga gcgcggcgtg agccctcccc cttgggatcc    480

cgcagctgac cagtcgcgct gacggacaga cagacagaca ccgcccccag ccccagctac    540

cacctcctcc ccggccggcg gcggacagtg gacgcggcgg cgagccgcgg gcaggggccg    600

gagcccgcgc ccggaggcgg ggtggagggg gtcggggctc gcggcgtcgc actgaaactt    660

ttcgtccaac ttctgggctg ttctcgcttc ggaggagccg tggtccgcgc gggggaagcc    720

gagccgagcg gagccgcgag aagtgctagc tcgggccggg aggagccgca gccggaggag    780

ggggaggagg aagaagagaa ggaagaggag agggggccgc agtggcgact cggcgctcgg    840

aagccgggct catggacggg tgaggcggcg gtgtgcgcag acagtgctcc agccgcgcgc    900

gctccccagg ccctggcccg ggcctcgggc cggggaggaa gagtagctcg ccgaggcgcc    960

gaggagagcg ggccgcccca cagcccgagc cggagaggga gcgcgagccg cgccggcccc   1020

ggtcgggcct ccgaaaccat gaactttctg ctgtcttggg tgcattggag ccttgccttg   1080

ctgctctacc tccaccatgc caagtggtcc caggctgcac ccatggcaga aggaggaggg   1140

cagaatcatc acgaagtggt gaagttcatg gatgtctatc agcgcagcta ctgccatcca   1200

atcgagaccc tggtggacat cttccaggag taccctgatg agatcgagta catcttcaag   1260

ccatcctgtg tgcccctgat gcgatgcggg ggctgctgca atgacgaggg cctggagtgt   1320

gtgcccactg aggagtccaa catcaccatg cagattatgc ggatcaaacc tcaccaaggc   1380

cagcacatag gagagatgag cttcctacag cacaacaaat gtgaatgcag accaaagaaa   1440

gatagagcaa gacaagaaaa atgtgacaag ccgaggcggt gagccgggca ggaggaagga   1500

gcctccctca gggtttcggg aaccagatct ctcaccagga aagactgata cagaacgatc   1560

gatacagaaa ccacgctgcc gccaccacac catcaccatc gacagaacag tccttaatcc   1620

agaaacctga aatgaaggaa gaggagactc tgcgcagagc actttgggtc cggagggcga   1680
```

gactccggcg gaagcattcc cgggcgggtg acccagcacg gtccctcttg gaattggatt 1740
cgccatttta tttttcttgc tgctaaatca ccgagcccgg aagattagag agttttattt 1800
ctgggattcc tgtagacaca cccacccaca tacatacatt tatatatata tatattatat 1860
atatataaaa ataaatatct ctattttata tatataaaat atatatattc tttttttaaa 1920
ttaacagtgc taatgttatt ggtgtcttca ctggatgtat ttgactgctg tggacttgag 1980
ttgggagggg aatgttccca ctcagatcct gacagggaag aggaggagat gagagactct 2040
ggcatgatct ttttttgtc ccacttggtg gggccagggt cctctcccct gcccaggaat 2100
gtgcaaggcc agggcatggg ggcaaatatg acccagtttt gggaacaccg acaaacccag 2160
ccctggcgct gagcctctct accccaggtc agacggacag aaagacagat cacaggtaca 2220
gggatgagga caccggctct gaccaggagt ttggggagct tcaggacatt gctgtgcttt 2280
ggggattccc tccacatgct gcacgcgcat ctcgccccca ggggcactgc ctggaagatt 2340
caggagcctg ggcggccttc gcttactctc acctgcttct gagttgccca ggagaccact 2400
ggcagatgtc ccggcgaaga gaagagacac attgttggaa gaagcagccc atgacagctc 2460
cccttcctgg gactcgccct catcctcttc ctgctcccct tcctggggtg cagcctaaaa 2520
ggacctatgt cctcacacca ttgaaaccac tagttctgtc cccccaggag acctggttgt 2580
gtgtgtgtga gtggttgacc ttcctccatc ccctggtcct tcccttccct tcccgaggca 2640
cagagagaca gggcaggatc cacgtgccca ttgtggaggc agagaaaaga gaaagtgttt 2700
tatatacggt acttatttaa tatccctttt taattagaaa ttaaaacagt taatttaatt 2760
aaagagtagg gtttttttc agtattcttg gttaatattt aatttcaact atttatgaga 2820
tgtatctttt gctctctctt gctctcttat ttgtaccggt ttttgtatat aaaattcatg 2880
tttccaatct ctctctccct gatcggtgac agtcactagc ttatcttgaa cagatattta 2940
attttgctaa cactcagctc tgccctcccc gatcccctgg ctccccagca cacattcctt 3000
tgaaataagg tttcaatata catctacata ctatatatat atttggcaac ttgtatttgt 3060
gtgtatatat atatatatat gtttatgtat atatgtgatt ctgataaaat agacattgct 3120
attctgtttt ttatatgtaa aaacaaaaca agaaaaaata gagaattcta catactaaat 3180
ctctctcctt ttttaatttt aatatttgtt atcatttatt tattggtgct actgtttatc 3240
cgtaataatt gtggggaaaa gatattaaca tcacgtcttt gtctctagtg cagtttttcg 3300
agatattccg tagtacatat ttatttttaa acaacgacaa agaaatacag atatatctta 3360
aaaaaaaaaa agcattttgt attaaagaat ttaattctga tctcaaaaaa aaaaaaaaaa 3420
aa 3422

<210> SEQ ID NO 7
<211> LENGTH: 3488
<212> TYPE: DNA
<213> ORGANISM: Homo sapiens

<400> SEQUENCE: 7
tcgcggaggc ttggggcagc cgggtagctc ggaggtcgtg gcgctggggg ctagcaccag 60
cgctctgtcg ggaggcgcag cggttaggtg gaccggtcag cggactcacc ggccagggcg 120
ctcggtgctg gaatttgata ttcattgatc cgggttttat ccctcttctt ttttcttaaa 180
catttttttt taaaactgta ttgtttctcg ttttaattta tttttgcttg ccattcccca 240
cttgaatcgg gccgacggct tggggagatt gctctacttc cccaaatcac tgtggatttt 300

```
ggaaaccagc agaaagagga aagaggtagc aagagctcca gagagaagtc gaggaagaga    360
gagacggggt cagagagagc gcgcgggcgt gcgagcagcg aaagcgacag gggcaaagtg    420
agtgacctgc ttttgggggt gaccgccgga gcgcggcgtg agccctcccc cttgggatcc    480
cgcagctgac cagtcgcgct gacggacaga cagacagaca ccgcccccag ccccagctac    540
cacctcctcc ccggccggcg gcggacagtg gacgcggcgg cgagccgcgg gcaggggccg    600
gagcccgcgc ccggaggcgg ggtggagggg gtcggggctc gcggcgtcgc actgaaactt    660
ttcgtccaac ttctgggctg ttctcgcttc ggaggagccg tggtccgcgc gggggaagcc    720
gagccgagcg gagccgcgag aagtgctagc tcgggccggg aggagccgca gccggaggag    780
ggggaggagg aagaagagaa ggaagaggag agggggccgc agtggcgact cggcgctcgg    840
aagccgggct catggacggg tgaggcggcg gtgtgcgcag acagtgctcc agccgcgcgc    900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc   1020
ggtcgggcct ccgaaaccat gaactttctg ctgtcttggg tgcattggag ccttgccttg   1080
ctgctctacc tccaccatgc caagtggtcc caggctgcac ccatggcaga aggaggaggg   1140
cagaatcatc acgaagtggt gaagttcatg gatgtctatc agcgcagcta ctgccatcca   1200
atcgagaccc tggtggacat cttccaggag taccctgatg agatcgagta catcttcaag   1260
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag gagagatgag cttcctacag cacaacaaat gtgaatgcag accaaagaaa   1440
gatagagcaa gacaagaaaa tccctgtggg ccttgctcag agcggagaaa gcatttgttt   1500
gtacaagatc cgcagacgtg taaatgttcc tgcaaaaaca cagactcgcg ttgcaaggcg   1560
aggcagcttg agttaaacga acgtacttgc agatctctca ccaggaaaga ctgatacaga   1620
acgatcgata cagaaaccac gctgccgcca ccacaccatc accatcgaca gaacagtcct   1680
taatccagaa acctgaaatg aaggaagagg agactctgcg cagagcactt tgggtccgga   1740
gggcgagact ccggcggaag cattcccggg cgggtgaccc agcacggtcc ctcttggaat   1800
tggattcgcc attttatttt tcttgctgct aaatcaccga gcccggaaga ttagagagtt   1860
ttatttctgg gattcctgta gacacaccca cccacataca tacatttata tatatatata   1920
ttatatatat ataaaaataa atatctctat tttatatata taaaatatat atattctttt   1980
tttaaattaa cagtgctaat gttattggtg tcttcactgg atgtatttga ctgctgtgga   2040
cttgagttgg gaggggaatg ttcccactca gatcctgaca gggaagagga ggagatgaga   2100
gactctggca tgatcttttt tttgtcccac ttggtggggc cagggtcctc tcccctgccc   2160
aggaatgtgc aaggccaggg catgggggca aatatgaccc agttttggga acaccgacaa   2220
acccagccct ggcgctgagc ctctctaccc caggtcagac ggacagaaag acagatcaca   2280
ggtacaggga tgaggacacc ggctctgacc aggagtttgg ggagcttcag gacattgctg   2340
tgctttgggg attccctcca catgctgcac gcgcatctcg cccccagggg cactgcctgg   2400
aagattcagg agcctgggcg gccttcgctt actctcacct gcttctgagt tgcccaggag   2460
accactggca gatgtcccgg cgaagagaag agacacattg ttggaagaag cagcccatga   2520
cagctcccct tcctgggact cgccctcatc ctcttcctgc tccccttcct ggggtgcagc   2580
ctaaaaggac ctatgtcctc acaccattga aaccactagt tctgtccccc caggagacct   2640
ggttgtgtgt gtgtgagtgg ttgaccttcc tccatcccct ggtccttccc ttcccttccc   2700
```

gaggcacaga gagacagggc aggatccacg tgcccattgt ggaggcagag aaaagagaaa 2760
gtgttttata tacggtactt atttaatatc cctttttaat tagaaattaa aacagttaat 2820
ttaattaaag agtagggttt tttttcagta ttcttggtta atatttaatt tcaactattt 2880
atgagatgta tcttttgctc tctcttgctc tcttatttgt accggttttt gtatataaaa 2940
ttcatgtttc caatctctct ctccctgatc ggtgacagtc actagcttat cttgaacaga 3000
tatttaattt tgctaacact cagctctgcc ctccccgatc ccctggctcc ccagcacaca 3060
ttcctttgaa ataaggtttc aatatacatc tacatactat atatatattt ggcaacttgt 3120
atttgtgtgt atatatatat atatatgttt atgtatatat gtgattctga taaaatagac 3180
attgctattc tgttttttat atgtaaaaac aaaacaagaa aaaatagaga attctacata 3240
ctaaatctct ctcctttttt aattttaata tttgttatca tttatttatt ggtgctactg 3300
tttatccgta ataattgtgg ggaaaagata ttaacatcac gtctttgtct ctagtgcagt 3360
ttttcgagat attccgtagt acatatttat ttttaaacaa cgacaaagaa atacagatat 3420
atcttaaaaa aaaaaaagca ttttgtatta aagaatttaa ttctgatctc aaaaaaaaaa 3480
aaaaaaaa 3488

<210> SEQ ID NO 8
<211> LENGTH: 3392
<212> TYPE: DNA
<213> ORGANISM: Homo sapiens

<400> SEQUENCE: 8
tcgcggaggc ttggggcagc cgggtagctc ggaggtcgtg gcgctggggg ctagcaccag 60
cgctctgtcg ggaggcgcag cggttaggtg gaccggtcag cggactcacc ggccagggcg 120
ctcggtgctg gaatttgata ttcattgatc cgggttttat ccctcttctt ttttcttaaa 180
catttttttt taaaactgta ttgtttctcg ttttaattta tttttgcttg ccattcccca 240
cttgaatcgg gccgacggct tggggagatt gctctacttc cccaaatcac tgtggatttt 300
ggaaaccagc agaaagagga aagaggtagc aagagctcca gagagaagtc gaggaagaga 360
gagacggggt cagagagagc gcgcgggcgt gcgagcagcg aaagcgacag gggcaaagtg 420
agtgacctgc ttttgggggt gaccgccgga gcgcggcgtg agccctcccc cttgggatcc 480
cgcagctgac cagtcgcgct gacggacaga cagacagaca ccgcccccag ccccagctac 540
cacctcctcc ccggccggcg gcggacagtg gacgcggcgg cgagccgcgg gcaggggccg 600
gagcccgcgc ccggaggcgg ggtggagggg gtcggggctc gcggcgtcgc actgaaactt 660
ttcgtccaac ttctgggctg ttctcgcttc ggaggagccg tggtccgcgc gggggaagcc 720
gagccgagcg gagccgcgag aagtgctagc tcgggccggg aggagccgca gccggaggag 780
ggggaggagg aagaagagaa ggaagaggag agggggccgc agtggcgact cggcgctcgg 840
aagccgggct catggacggg tgaggcggcg gtgtgcgcag acagtgctcc agccgcgcgc 900
gctccccagg ccctggcccg ggcctcgggc cggggaggaa gagtagctcg ccgaggcgcc 960
gaggagagcg ggccgcccca cagcccgagc cggagaggga gcgcgagccg cgccggcccc 1020
ggtcgggcct ccgaaaccat gaactttctg ctgtcttggg tgcattggag ccttgccttg 1080
ctgctctacc tccaccatgc caagtggtcc caggctgcac ccatggcaga aggaggaggg 1140
cagaatcatc acgaagtggt gaagttcatg gatgtctatc agcgcagcta ctgccatcca 1200
atcgagaccc tggtggacat cttccaggag taccctgatg agatcgagta catcttcaag 1260

```
ccatcctgtg tgcccctgat gcgatgcggg ggctgctgca atgacgaggg cctggagtgt   1320
gtgcccactg aggagtccaa catcaccatg cagattatgc ggatcaaacc tcaccaaggc   1380
cagcacatag gagagatgag cttcctacag cacaacaaat gtgaatgcag atgtgacaag   1440
ccgaggcggt gagccgggca ggaggaagga gcctccctca gggtttcggg aaccagatct   1500
ctcaccagga aagactgata cagaacgatc gatacagaaa ccacgctgcc gccaccacac   1560
catcaccatc gacagaacag tccttaatcc agaaacctga aatgaaggaa gaggagactc   1620
tgcgcagagc actttgggtc cggagggcga gactccggcg gaagcattcc cgggcgggtg   1680
acccagcacg gtccctcttg gaattggatt cgccatttta tttttcttgc tgctaaatca   1740
ccgagcccgg aagattagag agttttattt ctgggattcc tgtagacaca cccacccaca   1800
tacatacatt tatatatata tatattatat atatataaaa ataaatatct ctattttata   1860
tatataaaat atatatattc tttttttaaa ttaacagtgc taatgttatt ggtgtcttca   1920
ctggatgtat ttgactgctg tggacttgag ttgggagggg aatgttccca ctcagatcct   1980
gacagggaag aggaggagat gagagactct ggcatgatct tttttttgtc ccacttggtg   2040
gggccagggt cctctcccct gcccaggaat gtgcaaggcc agggcatggg ggcaaatatg   2100
acccagtttt gggaacaccg acaaacccag ccctggcgct gagcctctct accccaggtc   2160
agacggacag aaagacagat cacaggtaca gggatgagga caccggctct gaccaggagt   2220
ttggggagct tcaggacatt gctgtgcttt ggggattccc tccacatgct gcacgcgcat   2280
ctcgcccccca ggggcactgc ctggaagatt caggagcctg ggcggccttc gcttactctc   2340
acctgcttct gagttgccca ggagaccact ggcagatgtc ccggcgaaga gaagagacac   2400
attgttggaa gaagcagccc atgacagctc cccttcctgg gactcgccct catcctcttc   2460
ctgctcccct tcctggggtg cagcctaaaa ggacctatgt cctcacacca ttgaaaccac   2520
tagttctgtc cccccaggag acctggttgt gtgtgtgtga gtggttgacc ttcctccatc   2580
ccctggtcct tcccttccct tcccgaggca cagagagaca gggcaggatc cacgtgccca   2640
ttgtggaggc agagaaaaga gaaagtgttt tatatacggt acttatttaa tatccctttt   2700
taattagaaa ttaaaacagt taatttaatt aaagagtagg gttttttttc agtattcttg   2760
gttaatattt aatttcaact atttatgaga tgtatctttt gctctctctt gctctcttat   2820
ttgtaccggt ttttgtatat aaaattcatg tttccaatct ctctctccct gatcggtgac   2880
agtcactagc ttatcttgaa cagatattta attttgctaa cactcagctc tgccctcccc   2940
gatcccctgg ctccccagca cacattcctt tgaaataagg tttcaatata catctacata   3000
ctatatatat atttggcaac ttgtatttgt gtgtatatat atatatatat gtttatgtat   3060
atatgtgatt ctgataaaat agacattgct attctgtttt ttatatgtaa aaacaaaaca   3120
agaaaaaata gagaattcta catactaaat ctctctcctt ttttaatttt aatatttgtt   3180
atcatttatt tattggtgct actgtttatc cgtaataatt gtggggaaaa gatattaaca   3240
tcacgtcttt gtctctagtg cagtttttcg agatattccg tagtacatat ttatttttaa   3300
acaacgacaa agaaatacag atatatctta aaaaaaaaaa agcattttgt attaaagaat   3360
ttaattctga tctcaaaaaa aaaaaaaaaa aa                                 3392
```

<210> SEQ ID NO 9
<211> LENGTH: 576
<212> TYPE: DNA
<213> ORGANISM: Homo sapiens

<400> SEQUENCE: 9

```
atgaactttc tgctgtcttg ggtgcattgg agccttgcct tgctgctcta cctccaccat     60

gccaagtggt cccaggctgc acccatggca gaaggaggag ggcagaatca tcacgaagtg    120

gtgaagttca tggatgtcta tcagcgcagc tactgccatc caatcgagac cctggtggac    180

atcttccagg agtaccctga tgagatcgag tacatcttca agccatcctg tgtgcccctg    240

atgcgatgcg gggctgctg caatgacgag ggcctggagt gtgtgcccac tgaggagtcc     300

aacatcacca tgcagattat gcggatcaaa cctcaccaag gccagcacat aggagagatg    360

agcttcctac agcacaacaa atgtgaatgc agaccaaaga aagatagagc aagacaagaa    420

aatccctgtg ggccttgctc agagcggaga aagcatttgt ttgtacaaga tccgcagacg    480

tgtaaatgtt cctgcaaaaa cacagactcg cgttgcaagg cgaggcagct tgagttaaac    540

gaacgtactt gcagatgtga caagccgagg cggtga                              576


<210> SEQ ID NO 10
<211> LENGTH: 890
<212> TYPE: DNA
<213> ORGANISM: Homo sapiens

<400> SEQUENCE: 10

gttacattgc acaagataaa aatatatcat catgaacaat aaaactgtct gcttacataa     60

acagtaatac aaggggtgtt atgagccata ttcaacggga aacgtcgagg ccgcgattaa    120

attccaacat ggatgctgat ttatatgggt ataaatgggc tcgcgataat gtcgggcaat    180

caggtgcgac aatctatcgc ttgtatggga agcccgatgc gccagagttg tttctgaaac    240

atggcaaagg tagcgttgcc aatgatgtta cagatgagat ggtcagacta aactggctga    300

cggaatttat gcctcttccg accatcaagc attttatccg tactcctgat gatgcatggt    360

tactcaccac tgcgatcccc ggaaaaacag cattccaggt attagaagaa tatcctgatt    420

caggtgaaaa tattgttgat gcgctggcag tgtccctgcg ccggttgcat tcgattcctg    480

tttgtaattg tccttttaac agcgatcgcg tatttcgtct cgctcaggcg caatcacgaa    540

tgaataacgg tttggttgat gcgagtgatt ttgatgacga gcgtaatggc tggcctgttg    600

aacaagtctg gaaagaaatg cataaacttt tgccattctc accggattca gtcgtcactc    660

atggtgattt ctcacttgat aaccttattt ttgacgaggg gaaattaata ggttgtattg    720

atgttggacg agtcggaatc gcagaccgat accaggatct tgccatccta tggaactgcc    780

tcggtgagtt ttctccttca ttacagaaac ggctttttca aaaatatggt attgataatc    840

ctgatatgaa taaattgcag tttcatttga tgctcgatga gtttttctaa               890


<210> SEQ ID NO 11
<211> LENGTH: 5190
<212> TYPE: DNA
<213> ORGANISM: Artificial Sequence
<220> FEATURE:
<223> OTHER INFORMATION: vector is an adeno-associated viral type-2
      (AAV2) vector

<400> SEQUENCE: 11

cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtggagc tagttattaa tagtaatcaa    180

ttacggggtc attagttcat agcccatata tggagttccg cgttacataa cttacggtaa    240

atggcccgcc tggctgaccg cccaacgacc cccgcccatt gacgtcaata atgacgtatg    300
```

-continued

```
ttcccatagt aacgtcaata gggactttcc attgacgtca atgggtggag tatttacggt    360
aaactgccca cttggcagta catcaagtgt atcatatgcc aagtacgccc cctattgacg    420
tcaatgacgg taaatggccc gcctggcatt atgcccagta catgacctta tgggactttc    480
ctacttggca gtacatctac gtattagtca tcgctattac catggtgatg cggttttggc    540
agtacatcaa tgggcgtgga tagcggtttg actcacgggg atttccaagt ctccacccca    600
ttgacgtcaa tgggagtttg ttttgcacca aaatcaacgg gactttccaa aatgtcgtaa    660
caactccgcc ccattgacgc aaatgggcgg taggcgtgta cggtgggagg tctatataag    720
cagagctcgt ttagtgaacc gtcagatcgc ctggagacgc catccacgct gttttgacct    780
ccatagaaga caccgggacc gatccagcct ccgcggattc gaatcccggc cgggaacggt    840
gcattggaac gcggattccc cgtgccaaga gtgacgtaag taccgcctat agagtctata    900
ggcccacaaa aaatgctttc ttcttttaat atactttttt gtttatctta tttctaatac    960
tttccctaat ctctttcttt cagggcaata atgatacaat gtatcatgcc tctttgcacc   1020
attctaaaga ataacagtga taatttctgg gttaaggcaa tagcaatatt tctgcatata   1080
aatatttctg catataaatt gtaactgatg taagaggttt catattgcta atagcagcta   1140
caatccagct accattctgc ttttatttta tggttgggat aaggctggat tattctgagt   1200
ccaagctagg cccttttgct aatcatgttc atacctctta tcttcctccc acagctcctg   1260
ggcaacgtgc tggtctgtgt gctggcccat cactttggca aagaattggg attcgaacat   1320
cgattgaatt ccccggggat cctctagagt cgacctgcag aaaaagctgc ggaattgtac   1380
ccgcggccgc cgaaaccatg aactttctgc tgtcttgggt gcattggagc cttgccttgc   1440
tgctctacct ccaccatgcc aagtggtccc aggctgcacc catggcagaa ggaggagggc   1500
agaatcatca cgaagtggtg aagttcatgg atgtctatca gcgcagctac tgccatccaa   1560
tcgagaccct ggtggacatc ttccaggagt accctgatga gatcgagtac atcttcaagc   1620
catcctgtgt gcccctgatg cgatgcgggg gctgctgcaa tgacgagggc ctggagtgtg   1680
tgcccactga ggagtccaac atcaccatgc agattatgcg gatcaaacct caccaaggcc   1740
agcacatagg agagatgagc ttcctacagc acaacaaatg tgaatgcaga ccaaagaaag   1800
atagagcaag acaagaaaat ccctgtgggc cttgctcaga gcggagaaag catttgtttg   1860
tacaagatcc gcagacgtgt aaatgttcct gcaaaaacac agactcgcgt tgcaaggcga   1920
ggcagcttga gttaaacgaa cgtacttgca gatgtgacaa gccgaggcgg tgaccgggca   1980
ggaggaagcg gccgcgggga tccagacatg ataagataca ttgatgagtt tggacaaacc   2040
acagcttgcc tcgagcagcg ctgctcgaga gatctacggg tggcatccct gtgacccctc   2100
cccagtgcct ctcctggccc tggaagttgc cactccagtg cccaccagcc ttgtcctaat   2160
aaaattaagt tgcatcattt tgtctgacta ggtgtccttc tataatatta tggggtggag   2220
gggggtggta tggagcaagg ggcaagttgg gaagacaacc tgtagggcct gcggggtcta   2280
ttgggaacca agctggagtg cagtggcaca atcttggctc actgcaatct ccgcctcctg   2340
ggttcaagcg attctcctgc ctcagcctcc cgagttgttg ggattccagg catgcatgac   2400
caggctcagc taatttttgt tttttggta gagacggggt ttcaccatat tggccaggct   2460
ggtctccaac tcctaatctc aggtgatcta cccaccttgg cctcccaaat tgctgggatt   2520
acaggcgtga accactgctc ccttccctgt ccttctgatt ttgtaggtaa ccacgtgcgg   2580
accgagcggc cgcaggaacc cctagtgatg gagttggcca ctccctctct gcgcgctcgc   2640
```

```
tcgctcactg aggccgggcg accaaaggtc gcccgacgcc cgggctttgc ccgggcggcc   2700
tcagtgagcg agcgagcgcg cagctgcctg caggggcgcc tgatgcggta ttttctcctt   2760
acgcatctgt gcggtatttc acaccgcata cgtcaaagca accatagtac gcgccctgta   2820
gcggcgcatt aagcgcggcg ggtgtggtgg ttacgcgcag cgtgaccgct acacttgcca   2880
gcgccctagc gcccgctcct ttcgctttct tcccttcctt tctcgccacg ttcgccggct   2940
ttccccgtca agctctaaat cgggggctcc ctttagggtt ccgatttagt gctttacggc   3000
acctcgaccc caaaaaactt gatttgggtg atggttcacg tagtgggcca tcgccctgat   3060
agacggtttt tcgccctttg acgttggagt ccacgttctt taatagtgga ctcttgttcc   3120
aaactggaac aacactcaac cctatctcgg gctattcttt tgatttataa gggattttgc   3180
cgatttcggc ctattggtta aaaaatgagc tgatttaaca aaaatttaac gcgaatttta   3240
acaaaatatt aacgtttaca attttatggt gcactctcag tacaatctgc tctgatgccg   3300
catagttaag ccagccccga cacccgccaa cacccgctga cgcgccctga cgggcttgtc   3360
tgctcccggc atccgcttac agacaagctg tgaccgtctc cgggagctgc atgtgtcaga   3420
ggttttcacc gtcatcaccg aaacgcgcga gacgaaaggg cctcgtgata cgcctatttt   3480
tataggttaa tgtgcccgtg tctcaaaatc tctgatgtta cattgcacaa gataaaaata   3540
tatcatcatg aacaataaaa ctgtctgctt acataaacag taatacaagg ggtgttatga   3600
gccatattca acgggaaacg tcgaggccgc gattaaattc caacatggat gctgatttat   3660
atgggtataa atgggctcgc gataatgtcg ggcaatcagg tgcgacaatc tatcgcttgt   3720
atgggaagcc cgatgcgcca gagttgtttc tgaaacatgg caaaggtagc gttgccaatg   3780
atgttacaga tgagatggtc agactaaact ggctgacgga atttatgcct cttccgacca   3840
tcaagcattt tatccgtact cctgatgatg catggttact caccactgcg atccccggaa   3900
aaacagcatt ccaggtatta gaagaatatc ctgattcagg tgaaaatatt gttgatgcgc   3960
tggcagtgtc cctgcgccgg ttgcattcga ttcctgtttg taattgtcct tttaacagcg   4020
atcgcgtatt tcgtctcgct caggcgcaat cacgaatgaa taacggtttg gttgatgcga   4080
gtgattttga tgacgagcgt aatggctggc ctgttgaaca agtctggaaa gaaatgcata   4140
aacttttgcc attctcaccg gattcagtcg tcactcatgg tgatttctca cttgataacc   4200
ttatttttga cgaggggaaa ttaataggtt gtattgatgt tggacgagtc ggaatcgcag   4260
accgatacca ggatcttgcc atcctatgga actgcctcgg tgagttttct ccttcattac   4320
agaaacggct ttttcaaaaa tatggtattg ataatcctga tatgaataaa ttgcagtttc   4380
atttgatgct cgatgagttt ttctaatcag aattggttaa ttggttgtaa cattattcag   4440
attgggcccc gttccactga gcgtcagaca ccaaaatccc ttaacgtgag ttttcgttcc   4500
actgagcgtc agaccccgta gaaaagatca aaggatcttc ttgagatcct ttttttctgc   4560
gcgtaatctg ctgcttgcaa acaaaaaaac caccgctacc agcggtggtt tgtttgccgg   4620
atcaagagct accaactctt tttccgaagg taactggctt cagcagagcg cagataccaa   4680
atactgtcct tctagtgtag ccgtagttag gccaccactt caagaactct gtagcaccgc   4740
ctacatacct cgctctgcta atcctgttac cagtggctgc tgccagtggc gataagtcgt   4800
gtcttaccgg gttggactca agacgatagt taccggataa ggcgcagcgg tcgggctgaa   4860
cggggggttc gtgcacacag cccagcttgg agcgaacgac ctacaccgaa ctgagatacc   4920
tacagcgtga gctatgagaa agcgccacgc ttcccgaagg gagaaaggcg gacaggtatc   4980
cggtaagcgg cagggtcgga acaggagagc gcacgaggga gcttccaggg ggaaacgcct   5040
```

-continued

```
ggtatcttta tagtcctgtc gggtttcgcc acctctgact tgagcgtcga tttttgtgat   5100
gctcgtcagg ggggcggagc ctatggaaaa acgccagcaa cgcggccttt ttacggttcc   5160
tggccttttg ctggcctttt gctcacatgt                                    5190
```